(12) United States Patent
Bringmann et al.

(10) Patent No.: US 6,331,630 B1
(45) Date of Patent: Dec. 18, 2001

(54) DIMERIC ARYLISOQUINOLINE ALKALOIDS AND DERIVATIVES THEREOF

(75) Inventors: Gerhard Bringmann, Würzburg (DE); Michael R. Boyd, Ijamsville, MD (US); Matthias Wenzel, Wesseling (DE)

(73) Assignee: The United States of America as represented by the Department of Health and Human Services, Rockville, MD (US)

( * ) Notice: Subject to any disclaimer, the term of this patent is extended or adjusted under 35 U.S.C. 154(b) by 0 days.

(21) Appl. No.: 09/527,002

(22) Filed: Mar. 16, 2000

Related U.S. Application Data

(60) Division of application No. 09/001,801, filed on Dec. 31, 1997, now Pat. No. 6,140,339, which is a continuation-in-part of application No. 08/843,582, filed on Apr. 16, 1997, which is a division of application No. 08/195,547, filed on Feb. 14, 1994, now Pat. No. 5,639,761, said application No. 09/001,801, is a continuation-in-part of application No.08/ 674,359, filed on Jul. 1, 1996, now Pat. No. 5,789,594, which is a division of application No. 08/279,339, filed on Jul. 22, 1994, now Pat. No. 5,571,919, which is a continuation-in-part of application No. 08/674,362, filed on Jul. 1, 1996, now Pat. No. 5,763,613, which is a division of application No. 08/279,291, filed on Jul. 22, 1994, now Pat. No. 5,552,550, which is a continuation-in-part of application No. 08/721,084, filed on Sep. 24, 1996, now Pat. No. 5,786,482, which is a division of application No. 08/363, 684, filed on Dec. 23, 1994, now Pat. No. 5,578,729, which is a continuation of application No. 08/305,211, filed on Sep. 13, 1994, now abandoned, and a continuation-in-part of application No. 08/279,291, filed on Jul. 22, 1994, and a continuation-in-part of application No. 08/279,339, filed on Jul. 22, 1994, now Pat. No. 5,571,919.

(51) Int. Cl.[7] .................. C07D 401/10; C07D 401/04; A61K 31/4725; A61P 33/06

(52) U.S. Cl. ........................................ 546/140; 514/308

(58) Field of Search .............................. 546/140; 514/308

(56) References Cited

U.S. PATENT DOCUMENTS

| | | |
|---|---|---|
| 3,751,419 | 8/1973 | Ziegler . |
| 4,096,190 | 6/1978 | Rutledge . |
| 5,001,115 | 3/1991 | Sloan . |
| 5,025,020 | 6/1991 | VanDyke . |
| 5,260,315 | 11/1993 | Bringmann et al. . |
| 5,409,938 | 4/1995 | Boyd et al. . |
| 5,455,251 | 10/1995 | Boyd et al. . |
| 5,552,550 | 9/1996 | Bringmann et al. . |
| 5,571,919 | 11/1996 | Bringmann et al. . |
| 5,578,729 | 11/1996 | Bringmann et al. . |
| 5,639,761 | 6/1997 | Francois et al. . |
| 5,654,432 | 8/1997 | Boyd et al. . |

FOREIGN PATENT DOCUMENTS

| | | |
|---|---|---|
| 4117080 | 11/1992 | (DE) . |
| WO 92/18125 | 10/1992 | (WO) . |
| WO 94/24108 | 10/1994 | (WO) . |
| WO 95/21616 | 8/1995 | (WO) . |
| WO 95/21826 | 8/1995 | (WO) . |
| WO 96/03381 | 2/1996 | (WO) . |
| WO 96/03382 | 2/1996 | (WO) . |
| WO 96/15111 | 3/1996 | (WO) . |
| WO 99/33811 | 7/1999 | (WO) . |

OTHER PUBLICATIONS

Anonymous, "Natural Product Agents in Development by the United States National Cancer Institute (NCI)," *J. Natural Products*, 55 (7), 1018–1019 (1992).

Baptistella et al., "1, 8–Diazabicyclo[5.4.0]undec–7–ene as a Mild Deprotective Agent for Acetyl Groups," *Synthesis*, 436–438 (1989).

Benfield et al., "Studies of Fungal and Plant Laccases," *Phytochemistry*, 3, 79–88 (1964).

Berthelot et al., "Bromation Regioselective en Serie Aromatique. I: Monobromation en Position para de Phenols et d'amines Aromatiques par le Tribromure de Tetrabutylammonium," *Can. J. Chem.*, 67, 2061–2066 (1989).

Bobbitt, et al., "Electrochemistry of Natural Products. III. A Stereoselective, Stereospecific Phenol Coupling Reaction," *J. Am. Chem. Soc.*, 93, 3551–3552 (1971).

Boyd et al., "Novel Alkaloids from the Tropical Plant *Ancistrocladus abbreviatus* Inhibit Cell Killing by HIV–1 and HIV–2," *J. Medicinal Chemistry*, 34(12), 3402–3405 (1991).

Boyd et al., "Anti–HIV Michellamines from *Ancistrocladus korupensis*," *J. Medicinal Chemistry*, 37(12), 1740–1745 (1994).

Boyd et al., *Chemical Abstracts*, 117 (11), Abstract No. 104239k, p. 98, Sep. 14, 1992.

Bringmann et al., "Acetogenic Isoquinoline Alkaloids. Part 108. Dioncophylline D and 8–0–Methyldioncophylline D, 7,8'–Coupled Naphthylisoquinoline Alkaloids from Triphyophyllum Pelatum," *Chem. Abstracts* 35630K 376 (1999).

Bringmann et al., "A facile degradation procedure for determination of absolute configuration in 1, 3–dimethyltetra– and dihydroisoquinolines," *Phytochemistry*, 30, 2067–2070 (1991).

(List continued on next page.)

Primary Examiner—Evelyn Mei Huang
(74) Attorney, Agent, or Firm—Leydig, Voit & Mayer, Ltd.

(57) ABSTRACT

The present invention provides new naphthylisoquinoline derivatives. In particular, the present invention furthermore provides novel dimeric arylisoquinoline alkaloids comprised of coupled first and second arylisoquinoline monomers. Monomeric and dimeric compounds of the present invention have medically useful properties, such as antimicrobial properties, more specifically such as antimalarial and antiviral properties. Monomeric compounds of the present invention are also useful as building blocks or intermediates for synthesis of novel dimeric arylisoquinoline alkaloids. Monomeric and dimeric compounds of the present invention may be obtained in substantially pure form by total synthesis, partial synthesis, or derivatization from known synthetic or naturally occurring compounds, and by isolation and purification from plants of the Dioncophyllaceae and Ancistrocladaceae families.

11 Claims, 27 Drawing Sheets

OTHER PUBLICATIONS

Bringmann et al., "Feeding deterrency and growth retarding activity of the naphthylisoquinoline alkaloid dioncophylline A against spodoptera littoralis," *Phytochemistry*, 31, 3821–3825 (1992).

Bringmann et al., "The determination of the absolute configuration of N–methylated 1, 3–dimethyltetrahydroisoquinolines by oxidative degradation," *Planta Med.*, 59 (supp.) A619–A620 (1993).

Bringmann et al., "The naphthyl isoquinoline alkaloids," in *The Alkaloids*, 29 (Brossi, ed.), Chapter 3, 141–184 (Academic Press, New York, 1986).

Bringmann et al., "(±)-Dioncophyllacine A, A Naphthylisoquinoline Alkaloid with a 4–Methoxy Substituent from the Leaves of *Triphyophyllum peltatum*," *Phytochemistry*, 31(11), 4015–4108 (1992).

Bringmann et al., "A New Atropisomeric Dioncophylline A Derivative from *Triphyophyllum peltatum*," *Planta Med.*, 59 (Suppl.), A621–622 (1993).

Bringmann et al., "Ancistroheyine A, the First 7,8'–Coupled Naphthylisoquinoline Alkaloid from Ancistrocladus Heyneaus," *Chem. Abstracts* 126: 72581h, 342 (1997).

Bringmann et al., "Ancistrobrevine B, The First Naphthylisoquinoline Alkaloid with a 5,8'–Coupling Site, and Related Compounds from *Ancistrocladus abbreviatus*," *Phytochemistry*, 31(11), 4011–4014 (1992).

Bringmann et al., "Ancistrobrevine D: An Unusual Alkaloid from *Ancistrocladus abbreviatus*," *Planta Med.*, 58 (Suppl. 1), A703–704 (1992).

Bringmann et al., "Atrop–diastereomer Separation by Racemate Resolution Techniques: N–Methyl–Dioncophylline A and its 7–Epimer from *Ancistrocladus abbreviatus*," *Phytochemistry*, 30(4), 1307–1310 (1991).

Bringmann et al., "Chiral Economy with Respect to Rotational Isomerism: Rational Synthesis of Hamatine and (Optionally) Ancistrocladine from Joint Helical Precursors," *Heterocycles*, 28(1), 137–142 (1989).

Bringmann et al., "Dioncopeltine A and Dioncolactone A: Alkaloids from *Triphyophyllum peltatum*," *Phytochemistry*, 30(5), 1691–1696 (1991).

Bringmann et al., "Dioncophylline B, A Naphthylisoquinoline Alkaloid with A New Coupling Type from *Triphyophyllum peltatum*," *Phytochemistry*, 30(11), 3845–3847 (1991).

Bringmann et al., "Dioncophylline C from the Roots of *Triphyophyllum peltatum*, the First 5,1'–Coupled Dioncophyllaceae Alkaloid," *Phytochemistry*, 31(11), 4019–4024 (1992).

Bringmann et al., "Dioncophyllinol D, The First 4–Hydroxylated Naphthylisoquinoline Alkaloid, from the leaves of *Triphyophllum Peltatum*," *Heterocylces 47* (2), 985–990 (1998).

Bringmann et al., "First Total Synthesis of (−)–Dioncophylline A ('Triphyophylline') and of Selected Stereoisomers: Complete (Revised) Stereostructure," *Tetrahedron Letters*, 31 (5), 643–646 (1990).

Bringmann et al., "First total synthesis of Korupensamines A and B," *Heterocycles*, 39(2), 503–508 (1994).

Bringmann et al., "On the Biosynthesis of Acetogenic Tetrahydroisoquinoline Alkaloids: First In Vivo Feeding Experiments," *Planta Med.*, 57 (Suppl. 2), A98 (1991).

Bringmann et al., "On the Structure of the Dioncophyllaceae Alkaloids Dioncophylline A ('Triphyophylline') and 'O–Methyl–Triphyophylline,'" *Tetrahedron Letters*, 31(5), 639–642 (1990).

Bringmann et al., "Regioselective and Atropoisomeric–Selective Aryl Coupling to Give Naphthyl Isoquinoline Alkaloids: The First Total Synthesis of (−)–Ancistrocladine," *Angew. Chem. Int. Ed. Engl.*, 25(10), 913–915 (1986).

Bringmann et al., "The Absolute Configuration of Michellamine B, A 'Dimeric,' Anti–HIV–Active Naphthylisoquinoline Alkaloid," *Angew. Chem. Int. Ed. Engl.*, 32(8), 1190–1191 (1993).

Bringmann et al., "Ancistroheynine A, The First 7,8'–Coupled Naphthylisoquinoline Alkaloid from *Ancistrocladus Heyneanus*," *Phytochemistry*, 43(6), 1405–1410 (1996).

Bringmann et al., "Atropdiastereoselective Ring Opening of Bridged,'Axial–prostereogenic' Biaryls: Directed Synthesis of (+)–Ancistrocladisine," *Agnew. Chem. Int. Ed. Engl.*, 28 (12), 1671–1673 (1989).

Bringmann et al., "Biomimetic Oxidative Dimerization of Korupensamine A: Completion of the First Total Synthesis of Michellamines A, B, and C," *Tetrahedron*, 50(32), 9643–9648 (1994).

Bringmann et al., "Biomimetische Synthesen beider Molekulhalften der Ancistrocladus– und der Triphyophyllum–Alkaloide aus gemeinsamen Vorstufen," *Liebigs Ann. Chem.*, 2126–2134 (1985).

Bringmann et al., "Circular Dichroism of Michellamines: Independent Assignment of Axial Chirality by Calculated and Experimental CD Spectra," *Tetrahedron*, vol. 50, No. 26, 7807–7814 (Jun. 1994).

Bringmann et al., "Determination of Configuration at the Biaryl Axes of Naphthylisoquinoline Alkaloids by Long–Range NOE Effects," *Magnetic Resonance in Chemistry*, 35, 297–301 (1997).

Bringmann et al., "Dioncoline A and its atropisomer: Inverse hybrid type ancistrocladaceae/dioncophylliceae alkaloids from *ancistrocladus abbreviatus*," *Planta Med.*, 58 (supp. 1), A702–A703 (1992).

Bringmann et al., "Improved Methods for Dehydration and Hydroxy/Halogen Exchange Using Novel Combinations of Triphenylphosphine and Halogenated Ethanes," *Synthesis*, 139–141 (1983).

Bringmann et al., "Isoancistrocladine from *Ancistrocladus Heyneanus*: The First Naturally Occurring N–Unsubstituted CIS–Configurated Naphthyltetrahydroisoquinoline Alkoid," *Phytochemistry*, 35(1), 259–261 (1994).

Bringmann et al., "Isolation, Structure Elucidation, and Total Synthesis of Ancistrocline, an Alkaloid of *ancistrocladus tectorius*," *Planta Med.*, 58, (Suppl. 1), A704 (1992).

Bringmann et al., "Isoquinolines and Naphthalenes from β–Polyketones: Model Reactions for an Extraordinary Alkaloid Biosynthesis," *Angew. Chem. Int. Ed. Engl.*, 21(3), 200–201 (1982).

Bringmann et al., "The Cultivation of Tropical Lianas of the Genus Ancistrocladus," *Planta Med.*, 59 (supp.), A623–624 (1993).

Bringmann et al., "The Enantioselective Synthesis of Optically Active, Benzene Nucleus–Substituted 1–Phenylethylamines from the Corresponding Acetophenones," *Liebigs Ann. Chem.*, 795–805 (1990).

Bringmann et al., "The Synthesis of All Possible Isomeric 6, 8–Dioxygenated 1, 3–Dimethyl–1, 2, 3, 4–tetrahydroisoquinoline Methyl Ethers—Useful Chiral Building Blocks for Naphthylisoquinoline Alkaloids," *Liebigs Ann. Chem.*, 877–888 (1993).

Bringmann et al., "A Simple, Chiral–Pool–Independent Synthesis of Enantiomerically Pure Alanine–Derived α–Amino Aldehyde Acetals," *Communications*, 608–610 (1989).

Bringmann, et al., "Stereocontrolled Ring Opening of Axially Prostereogenic Biaryl Lactones with Hydrogen Nucleophiles: Directed Synthesis of a Dioncophylline A Precursor and (Optionally) its Atropdiastereomer," *Synthesis*, 825–827 (1991).

Bundgarrd, H., "Design of prodrugs," in *Elsevier*, 1–3, 10, 35–36 (Amsterdam, 1985).

Casey et al., "Interconversion of λ–Silyl α, β–Unsaturated Carbonyl Compounds and Siloxybutadienes by 1, 5–Shifts of Silicon Between Carbon and Oxygen," *J. Org. Chem.*, 46, 2089–2092 (1981).

Chapman et al., "Synthesis of Triflates of 2, 4–Dinitrophenol and N–Hydroxysduccinimide," *Synthesis*, 591–592 (1971).

Chen et al., "Isolation and identification of the alkaloids from *ancistrocladus tectorius*," *Yao Hsueh Hsueh Pao* (China) (i.e., *Acta Pharmaceutica Silica*), 16, 519–523 (1981).

Chenera et al., "Total Synthesis of ({)–Calanolide A, A Non–Nucleoside Inhibitor of HIV–1 Reverse Transcriptase," *J. Org. Chem.*, 58, 5605–5606 (1993).

Desjardin et al., "Qunatitative assessment of antimalarial activity in vitro by a semiautomated microdilution technique," *Antimicrobial Agents Chemother.*, 16, 710–718 (1979).

Dewar et al., "AMI: A New General Purpose Quantum Mechanical Molecular Model," *J. Am. Chem. Soc.*, 107, 3902–3909 (1985).

Ekong et al., "Comparison of the in vitro activities of quassinoids with activity against *plasmodium falciparum*. anisomycin and some other inhibitors of eukaryotic protein synthesis," *Biochem. Pharmacol.*, 40, 297–301 (1990).

Farina et al., "Polycyclic Hydroxyguinones—VIII," *Tetrahedron*, 38 (10), 1531–1537 (1982).

Flaig et al., "Reaktionen Mit Oxodierenden Enzymen Aus Mikroorganismen," *Planta Med.*, 9, 123–139 (1961).

Fleischhauer et al., "Messung und Berechnung der CD–Spektren der Biaryl–Alkaloids Ancistrocladein un Dioncophyllein A," *Z. Naturforsch*, 48b, 140–148 (1993).

Foucher et al., *Plantes Med. Pytother.*, 9, 87–98 (1975).

François et al., "Activity of Extracts and Naphthylisoquinoline Alkaloids from *Triphyophyllum peltatum, Ancistrocladus abbreviatus* and *A. barteri* against *Plasmodium falciparum* In Vitro," *Phytochemistry*, 35(6), 1461–1464 (1994).

Govindachari et al., *Tetrahedron*, 27, 1013–1026 (1971).

Govindrachari et al., *Indian J. Chem.*, 13(7), 641–643 (1975).

Grimm et al., "Deleterious effects of naphthylisoquinoline alkaloids on survival and growth of *spodoptera littoralis*," *Planta Med.*, 58, (supp. 1), A630 (1992).

Guinaudeau et al., "Bisbenzylisoquinoline alkaloids from *cyclea barbata*," *J. Nat. Prod.*, 56, 1989–1992 (1993).

Gulakowski et al., "A Semiautomatic Multiparameter Approach for Anti–HIV Drug Screening," *J. Virological Methods*, 33, 87–100 (1991).

Gustafson et al., "AIDS–Antiviral Sulfolipids from Cyanobacteria (Blue–Green Algae)," *J. National Cancer Insitute*, 81 (16) (Aug. 16, 1989).

Hallock et al., "Korupensamines A–D, Novel Antimalarial Alkaloids from *Ancistrocladus korupensis*," *J. Org. Chem.*, 59, 6349–6355 (1994).

Hallock et al., "Preparative Separation of Naphthyltetrahydroisoquinoline Alkaloids from *Ancistrocladus korupensis* by Centrifugal Partition Chromatography," *J. Chromatograph.*, 688, 1–2 (1994).

Hallock et al., "Yaoundamines A and B, New Antimalarial Naphthylisoquinoline Alkaloids from *Ancistrocladus korupensis*," *Tetrahedron*, 53(24), 8121–8128 (1997).

Handford et al., "Syntheses of Eleutherolic Acid," *J. Chem. Soc.*, 3896–3897 (1963).

Harel et al., "Purification and Multiplicity of Catechol Oxidase from Apple Chloroplasts," *Phytochemistry*, 4, 783–790 (1965).

Hodgson et al., "The Action of Fuming Nitric Acid on the 4–Halogeno–2: 6–dibromo–phenols and –anisoles. Anomalous Behaviour of Fluorine Derivatives," *J. Chem. Soc.*, 1085–1087 (1930).

Holland, in *Organic Synthesis with Oxidative Enzymes*, Chapter 8, Miscellaneous Oxidative Bioconversions, "1. Oxidative Coupling of Phenols and the Formation of Quinones," VCH, Weinheim, 341–351, 380–381 (1992).

Hoye et al., "Total Synthesis of Michellamines A–C: Important Anti–HIV Agents," *Tetrahedron Letters*, 35 (47), 8747–8750 (1994).

Ismail et al., "Synthesis of Benzothiazoles. α–Amino–(4–hydroxy–6–benzothiazolyl) Propionic Acid," *J. Org. Chem.*, 45, 2243–2246 (1980).

Jurczak et al., "Optically Active N–Protected α–Amino Aldehydes in Organic Synthesis," *Chem. Rev.*, 89, 149–164 (1989).

Kelly et al., "Convergent Total Synthesis of the Michellamines," *Tetrahedron Letters*, 35(41), 7621–7624 (1994).

Laatsch, "Isodiospyrin und Elliptinon.—Synthese 6, 6'–dimerer Bijuglone durch Phenoloxidation," *Liebigs Ann. Chem.*, 319–339 (1984).

Laatsch, "Synthese von Biramentaceon, Mamegakinon und Rotundichinon," *Liebigs Ann. Chem.*, 1321–1347 (1980).

Likhitwitayawuid et al., "Cyctotoxic and antimalarial bisbenzylisoquinoline alkaloids from *stephania erecta*," *J. Nat. Prod.*, 56, 30–38 (1993).

Lin et al., "Cytotoxic and antimalarial bisbenzylisoquinoline alkaloids from *cyclea barbata*," *J. Nat. Prod.*, 56, 22–29 (1993).

Lipshutz et al., "Cyanocuprate–Mediated Intramolecular Biaryl Couplings Applied to an Ellagitannin. Synthesis of (+)–O–Permethyltellimagrandin II," *Tetrahedron*, 35 (31), 5567–5570 (1994).

Manfredi et al., "Novel Alkaloids from the Tropical Plant *Ancistrocladus Abbreviatus* Inhibit Cell Killing by HIV–1 and HIV–2," *J. Medicinal Chemistry*, 34 (12), 3402–3405 (1991).

McMahon et al., "Diarylsulfones, a New Class of Nonnucleoside Antiviral Inhibitors of Human Immunodeficiency Virus Type I Reverse Transcriptase," *Antimicrobial Agents and Chemotherapy*, 37 (4), 754–760 (1993).

Merck Index, Ninth Edition, 276, 1047–1048 (1976).

Nicholl, in *An Introduction to Genetic Engineering*, Cambridge Univ. Press, Cambridge, pp. 1–5 & 127–130 (1994).

Noyori et al., "Rational Designing of Efficient Chiral Reducing Agents. Highly Enantioselective Reduction of Aromatic Ketones by Binaphthol–Modified Lithium Aluminum Hydride Reagents," *J. Am. Chem. Soc.*, 106, 6709–6716 (1984).

O'Neill et al., "Plants as sources of antimalarial drugs, Part I, In vitro test method for the evaluation of crude extracts from plants," *Plant Med.*, 51, 394–399 (1985).

Old et al., in *Principles of Gene Manipulation*, Blackwell Scientific Publishers, London, pp. 3–13 & 108–221 (1992).

Owton et al., "tert–Butyl–3–Carboxyethyl–3–Phosphonodiethylpropionate. A Novel Reagent for Stobbe–like Condensations," *Synthetic Communications*, 23 (15), 2119–2125 (1993).

Pavanand et al., "Antimalarial activity of *tiliacora triandradields* against *plasmodium falciparum* in vitro," *Phytother. Res.*, 3, 215–217 (1989).

Pearson et al., "The Ortho Bromination of Phenols," *J. Org. Chem.*, 32, 2358–2360 (1967).

Rizzacasa et al., "Synthetic Approaches to the Alkaloids of the Ancistrocladacceae: Dehydroancistrocladisine," *J. Chem. Soc.*, 301–302 (1989).

Rizzacasa et al., "The Synthesis of Stypandrol, A Toxic Binaphthalenetetrol Isolated from *Stypandra imbricata*: New Synthesis of Dianellidin and Stypandrone," *Aust. J. Chem.*, 41, 1087–1097 (1988).

Robb et al., On the Heterogeneity of the Tyrosinase of Broad Bean (Vicia Faba L.), *Phytochemistry*, 4, 731–740 (1965).

Ruangrungsi et al., "Traditional Medicinal Plants of Thailand, V. Ancistrotectorine, A New Naphthalene–Isoquinoline Alkaloid from *Ancistrocladus tectorius*," *J. Natural Products*, 48 (4), 529–535 (Jul.–Aug. 1985).

Sandström et al., "Antiviral Therapy in AIDS Clinical Pharmacological Properties and Therapeutic Experience To Date," *Drugs*, 34, 373–390 (1987).

Saunders, *Peroxidase*, Butterworth, London, pp. 1–52 (1964).

Savard et al., "Reactions of Ketene Acetals—14," *Tetrahedron*, 40 (18), 3455–3464 (1984).

Scott, "Oxidative Coupling of Phenolic Compounds," in *Quarterly Reviews*, (London), 19, 1–35 (1965).

Sharma et al., "Alkaloids and terpenoids of *ancistrocladus heyneanus, sagittaria sagitifolia, lyonia formosa* and *hedychium spicatum,*" *Phytochemistry*, 14, 578–579 (1975).

Shimizu et al., "A Simple and Efficient Synthesis of 2–, 3–, or 4– (2–Nitrophenyl) pyridine Derivatives via Palladium Catalyzed Ullmann Cross–Coupling Reaction," *Tetrahedron Letters*, 34 (21), 3421–3424 (1993).

Snieckus, "Directed Ortho Metalation. Tertiary Amide and O– Carbamate Directors in Synthetic Strategies for Polysubstituted Aromatics," *Chemical Reviews*, 90, 879–933 (1990).

Sofer, *Introduction to Genetic Engineering*, Butterworth–Heinemenn, Stoneham, MA, pp. 1–21 & 103–126 (1991).

Steinberg et al., in *Recombinant DNA Technology Concepts and Biomedical Applications*, Prentice Hall, Englewood Cliffs, NJ, pp. 81–124 & 150–162 (1993).

Stuart–Harris et al., in *The Background to Chemotherapy of Virus Diseases*, Chapter 5, 76–77 (Charles C. Thomas Publishers, Springfield, IL (1965).

Supko et al., "Determination of Michellamine B in Biological Fluids by High–Performance Liquid Chromatography with Flourescence Detection," *Analytical Biochemistry*, 216, 52–60 (1994).

Suzuki, "New Synthetic Transformations via Organoboron Compounds," *Pure & Appl. Chem.*, 66 (2), 213–222 (1994).

Thomas et al., "*Ancistrocladus korupensis* (Ancistrocladacceae): A New Specis of Liana from Cameroon," *Novon*, 3(4), 494–498 (1993).

Trager et al., "Human malarial parasites in continuous culture," *Science*, 193, 673–675 (1976).

Vlietstra et al., "Trimethylacetic Formic Anhydride. Improved Preparation and Use As a Highly Efficient and Selective N–formylating Reagent," *J. Royal Netherlands Chemical Society*, 101, 460–462 (1982).

Wang et al., "Remote Directed Metalation of Biaryl σ–Carbamates. Ring to Ring Carbamoyl Transfer Route to Biaryls, Dibenzo[b,d]pyranones, and the Natural Flourenone Dengibsin," *J. Org. Chem.*, 57, 424–426 (1992).

Watanabe et al., "Synthesis of Sterically Hindered Biaryls via the Palladium–Catalyzed Cross–Coupling Reaction of Arylboronic Acids or their Esters with Haloarenes," *Synlett*, 207–210 (Mar. 1992).

Weislow et al., "New Soluble–Formazan Assay for HIV–1 Cytopathic Effects: Application to High–Flux Screening of Synthetic and Natural Products for AIDS–Antiviral Activity," *J. National Cancer Institute*, 81 (8), 577–586 (Apr. 19, 1989).

Whiting, in *Comprehensive Organic Synthesis*, (Trost and Fleming, eds.), Peragamon Press, Oxford, 659–703 (1991).

Ye et al., "Selective antimalarial activity of tetrandine against chloroquinone resistant *plasmodium falciparum,*" *Biochem. Biophys. Res. Com.*, 159, 242–248 (1989).

N-Methyl-dioncophylline A

Ancistrocladine

Dioncolactone A

Ancistrobrevine D

5'-O-Demethyl-7-epi-dioncophylline A

Hamatine

5'-O-Demethyl-8-O-methyl-7-epi-dioncophylline A

Dioncophylleine A

Ancistrobarterine A 7-epi-Dioncophylline A

N-Methyl-ancistrocladine

N-Formyl-ancistrocladine

*N*-Formyl-8-*O*-pivaloyl-dioncophylline C

*N*-Formyl-8-*O*-benzoyl-dioncophylline C

*N*-Formyl-8-*O*-methyl-dioncophylline C

*N*-Formyl-8-*O*-acetyl-dioncophylline C

DIMERIC ARYLISOQUINOLINE ALKALOIDS AND DERIVATIVES THEREOF

CROSS-REFERENCE TO RELATED APPLICATIONS

This patent application is a divisional of U.S. patent application Ser. No. 09/001,801, filed on Dec. 31, 1997 which issued as U.S. Pat. No. 6,140,339, which is a continuation-in-part of (a) U.S. patent application Ser. No. 08/843,582, filed Apr. 16, 1997, which is a divisional of U.S. patent application Ser. No. 08/195,547, filed Feb. 14, 1994, which issued as U.S. Pat. No. 5,639,761, (b) U.S. patent application Ser. No. 08/674,359, filed Jul. 1, 1996, which issued as U.S. Pat. No. 5,789,594, which is a divisional of U.S. patent application Ser. No. 08/279,339, filed Jul. 22, 1994, which issued as U.S. Pat. No. 5,571,919, (c) U.S. patent application Ser. No. 08/674,362, filed Jul. 1, 1996, which issued as U.S. Pat. No. 5,763,613, which is a divisional of U.S. patent application Ser. No. 08/279,291, filed Jul. 22, 1994, which issued as U.S. Pat. No. 5,552,550, and (d) U.S. patent application Ser. No. 08/721,084, filed Sep. 24, 1996, which issued as U.S. Pat. No. 5,786,482, which is a divisional of U.S. patent application Ser. No. 08/363,684, filed Dec. 23, 1994, which issued as U.S. Pat. No. 5,578,729, which is a continuation of U.S. patent application Ser. No. 08/305,211, filed Sep. 13, 1994, now abandoned, and a continuation-in-part of U.S. patent application Ser. No. 08/279,291, filed Jul. 22, 1994, which issued as U.S. Pat. No. 5,552,550, and U.S. patent application Ser. No. 08/279,339, filed Jul. 22, 1994, which issued as U.S. Pat. No. 5,571,919.

TECHNICAL FIELD OF THE INVENTION

The present invention relates to monomeric and dimeric arylisoquinoline alkaloids, derivatives, and compositions thereof. The present invention further relates to methods of preparing and using monomeric and dimeric arylisoquinoline alkaloids and derivatives thereof.

BACKGROUND OF THE INVENTION

Arylisoquinoline alkaloids exhibiting remarkable anti-parasitic and/or antiviral properties have recently been identified. Examples of such arylisoquinolines can be found in Boyd et al., U.S. Pat. No. 5,455,251; Boyd et al., U.S. Pat. No. 5,654,432; Frangois et al., U.S. Pat. No. 5,639,761; Francois et al., U.S. patent application Ser. No. 08/843,582; Boyd et al., U.S. Pat. No. 5,409,938; Bringmann et al., U.S. Pat. No. 5,571,919; Bringmann et al., U.S. patent application Ser. No. 08/674,359 U.S. Pat. No. 5,789,594; Bringmann et al., U.S. Pat. No. 5,552,550; U.S. patent application Ser. No. 08/674,362; Bringmann et al., U.S. Pat. No. 5,578,729; Bringmann et al., U.S. patent application Ser. No. 08/721,084 U.S. Pat. No. 5,786,482; and Bringmann and Pokorny, The Alkaloids, Vol. 46 (G. Cordell, ed.), Academic Press, New York, 1995, pp. 127–271. Arylisoquinoline alkaloids of this class include monomeric arylisoquinoline alkaloids ("monomers") and dimeric arylisoquinoline alkaloids ("dimers").

Monomeric arylisoquinoline alkaloids include korupensamines and derivatives thereof, which possess a C-8' to C-5 naphthalene/isoquinoline linkage, and non-korupensamines or other monomeric naphthylisoquinoline alkaloids and derivatives thereof, which lack a C-8' to C-5 naphthylene/isoquinoline linkage. The monomeric arylisoquinoline alkaloids and derivatives thereof have particular usefulness as preventative and/or therapeutic agents, for example, as antiparasitic agents. For example, the monomeric arylisoquinoline alkaloid dioncophylline C is among the most potent known antimalarial compounds with in vivo activity against malaria-causing parasites. Further, the monomeric arylisoquinolines can be used as precursors for the synthesis of medically useful dimeric arylisoquinoline alkaloids.

Dimeric arylisoquinoline alkaloids are exemplified by the michellamines, which, based on their molecular structure, are comprised of two monomeric arylisoquinoline alkaloid units coupled together (e.g., two monomeric or molecular "halves"). Michellamines or related arylisoquinoline alkaloid dimers or derivatives thereof may be either "homodimeric" (comprised of two monomeric arylisoquinoline halves which are the same) or "heterodimeric" (comprised of two monomeric arylisoquinoline halves which are different).

Dimeric arylisoquinoline alkaloids have highly desirable and eminently useful medical properties that are distinct from the properties of the monomeric naphthylisoquinoline alkaloids which comprise their molecular halves. For example, the michellamines, such as michellamine B, are highly effective inhibitors of the replication and resultant destructive effects of the human immunodeficiency virus (HIV) in human cells; moreover, the range of anti-HIV activity of these exemplary dimeric arylisoquinoline alkaloids is exceptionally broad, encompassing diverse strains and isolates of both the major viral types, HIV-1 and HIV-2 and a wide variety of human host cell lines; and, their mechanism of antiviral activity is distinct from any other known mechanistic class.

While the available monomeric and dimeric arylisoquinoline alkaloids have a variety of important medical and chemical uses and applications, new derivatives and structural subtypes of this class of compounds are expected to have additional advantageous properties. For example, new monomeric arylisoquinoline alkaloids can serve as precursors or building blocks for new dimeric arylisoquinoline alkaloids. Furthermore, in any given situation or indication, new monomeric and dimeric arylisoquinoline alkaloids are expected to have useful new or improved medical properties and applications, such as greater therapeutic potency against a particular disease or disease-causing organism, a broader spectrum of therapeutic activity against diverse diseases or disease-causing organisms, enhanced oral bioavailability, less toxicity in a particular host mammal, more advantageous pharmacokinetics and/or tissue distribution in a given host mammal, and the like. In addition, new monomeric and dimeric arylisoquinoline alkaloids are potentially useful for in-vitro assays and antimicrobial research.

In view of the foregoing, there exists a need for new medically and chemically useful monomeric and dimeric arylisoquinoline alkaloids and derivatives thereof. The present invention provides such monomeric and dimeric arylisoquinoline alkaloids and derivatives thereof. These and other advantages of the present invention, as well as additional inventive features, will be apparent from the description of the invention provided herein.

BRIEF SUMMARY OF THE INVENTION

The present invention provides new monomeric derivatives of the C-8'-7 linked naphthylisoquinoline alkaloid dioncophylline D. The invention also provides new C-4 substituted monomeric arylisoquinoline alkaloid derivatives of dioncophylline D, ancistrobrevine A, 6-O-demthylancistrobrevine A, yaoundamine A, yaoundamine B, ancistroheynine A, dioncophyllacine A, dioncophyllacine B, dioncophylline B, dioncopeltine A, dioncophylline A, dioncophylline C, dioncolactone A, N-methyl-dioncophylline A, ancistrobrevine D, ancistrocladine, 5'-O-demthyl-8-O-methyl-7-epi-dioncophylline A, 5'-O-demthyl-7-epi-dioncophylline A, dioncophylleine A, hamatine, ancistrobarterine A, 7-epi-dioncophylline A, N-formyl-ancistrolcladine, N-methyl-ancistrocladine, 6-deoxy-N-methyl-ancistrocladine, N-formyl-O,O-dimethyl-dioncophylline C, N-formyl-dioncophylline C, N-formyl-8-O-benzyl-dioncophylline C, N-formyl-8-O-methyl-dioncophylline C, N-formyl-8-O-pivaloyl-dioncophylline C, N-formyl-8-O-acetyl-dioncophylline C, N-formyl-8-O-benzoyl-dioncophylline C, 8-O-methyl-dioncophylline C, korupensamine A, korupensamine B, korupensamine C, korupensamine D, and ancistrobrevine B.

The present invention furthermore provides novel dimeric arylisoquinoline alkaloids comprised of coupled first and second arylisoquinoline monomers, wherein either or both of said monomer(s) is (are) monomeric compound(s) of the present invention.

Monomeric and dimeric compounds of the present invention have medically useful properties, such as antimicrobial properties, more specifically such as antimalarial and antiviral properties. Monomeric compounds of the present invention are also useful as building blocks or intermediates for synthesis of novel dimeric arylisoquinoline alkaloids.

Monomeric and dimeric compounds of the present invention may be obtained in substantially pure form by total synthesis, partial synthesis or derivatization from known synthetic or naturally occurring compounds, and by isolation and purification from plants of the Dioncophyllaceae and Ancistrocladaceae families.

DESCRIPTION OF THE PREFERRED EMBODIMENTS

The present invention provides derivatives of dioncophylline D, wherein the configuration at C-1 or C-3 is instead S; one or more phenolic hydroxyl group(s) is instead an ester, sulfonate ester, or ether group; a methyl ether group is instead a phenolic hydroxyl group; one or more phenolic hydroxyl group(s) is instead an aromatic hydrogen substituent; the secondary amine site is instead an amide, sulfonamide, tertiary amine, alkyl quaternary ammonium salt or corresponding Hoffmann elimination product thereof; one or more aromatic hydrogen substituent(s) is instead halo, nitro, amino, hydroxyl, acyloxy, alkoxy, aryloxy, glycosyloxy, thiol or cyano; at least one $CH_3$ is instead H; and/or the tetrahydroisoquinoline is instead a dihydroisoquinoline; with the proviso that said derivative is not ancistrobrevine A, 6-O-demethyl-ancistrobrevine A, yaoundamine A, yaoundamine B, or ancistroheynine A.

Figure 1A:
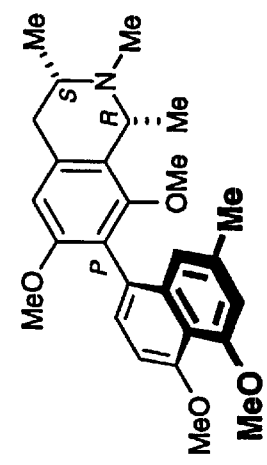
FIG. 1A illustrates the structures of dioncophylline D, ancistrobrevine A, 6-O-demethyl-ancistrolbrevine A, and yaoundamine A.
Figure 1A:
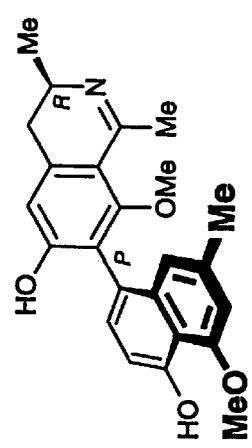
Figure 1A:
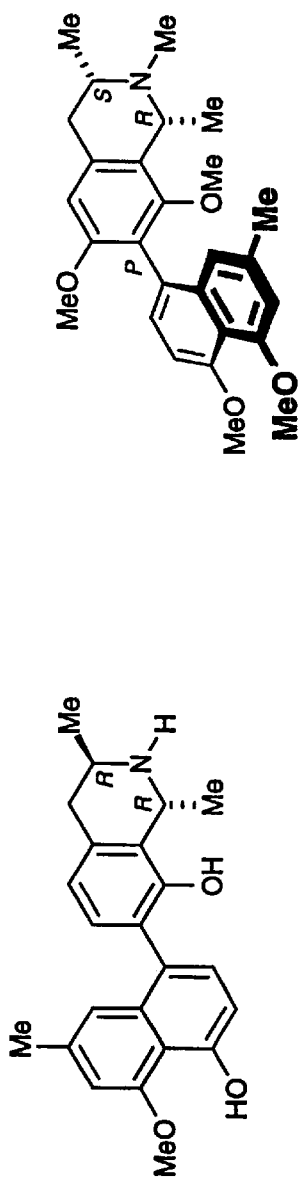
Figure 1A:
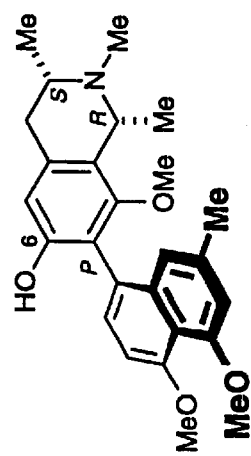
Figure 1B:
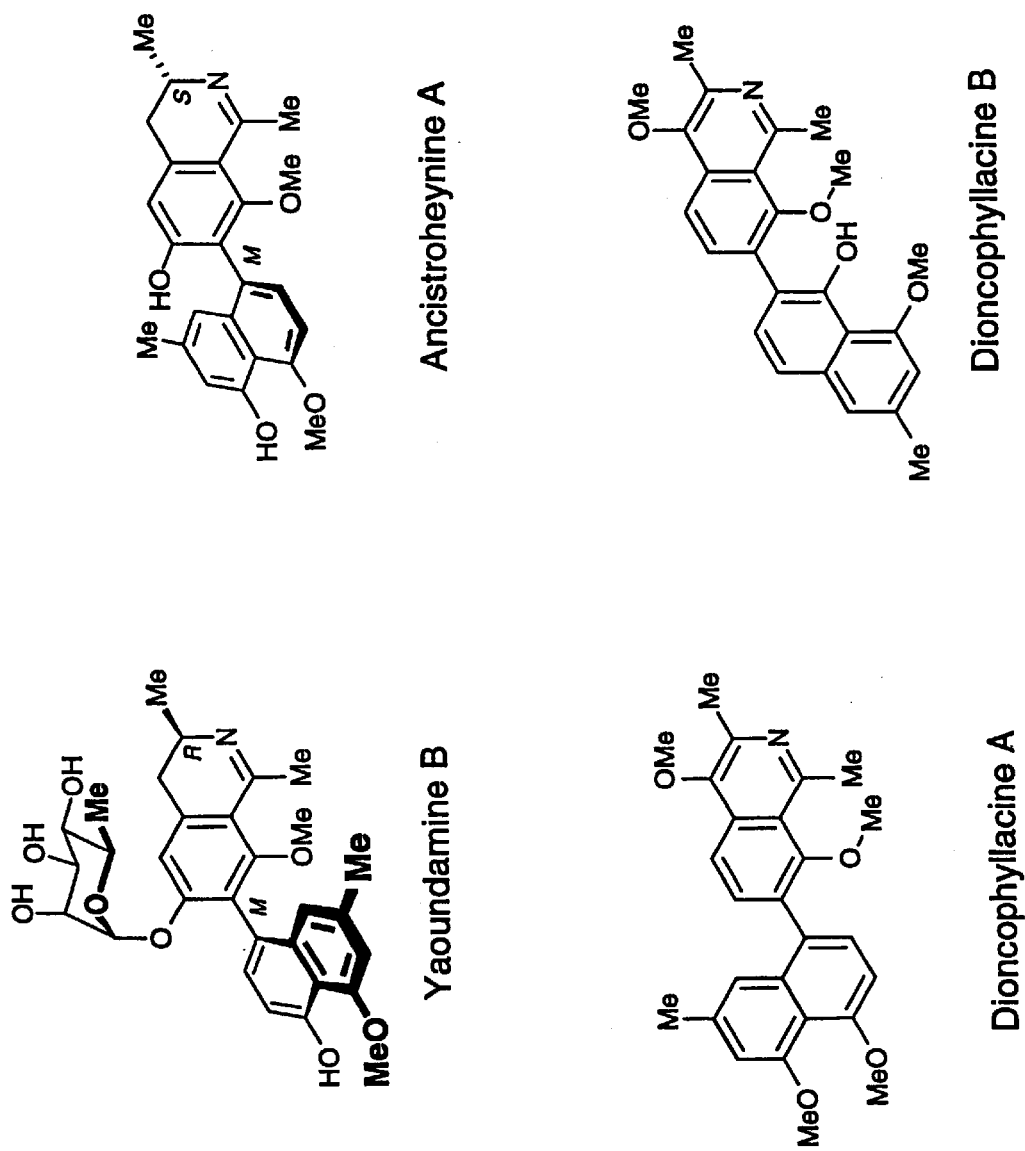
FIG. 1B illustrates the structure of yaoundamine B, ancistroheynine A, dioncophyllacine A, and dioncophyllacine B.
Figure 2A:
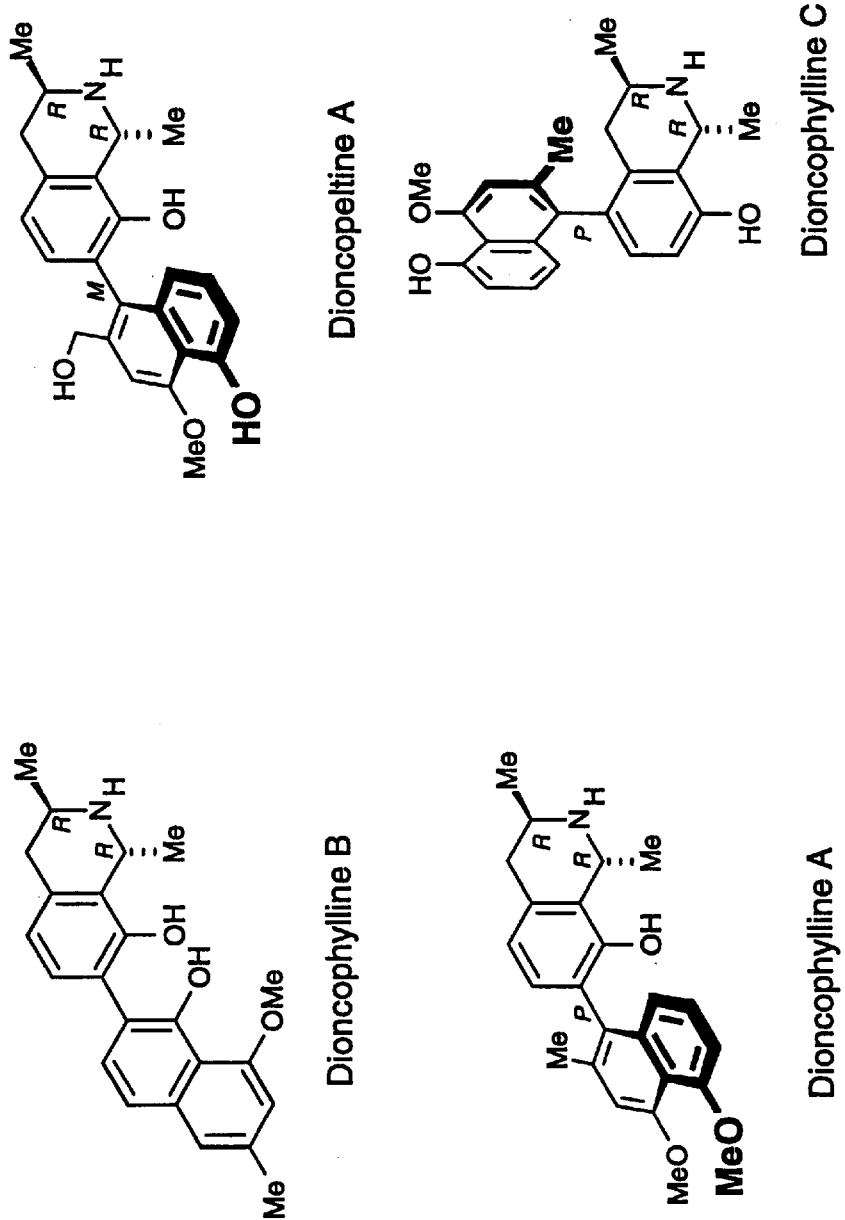
FIG. 2A illustrates the structures of dioncophylline B, dioncopeltine A, dioncophylline A, and dioncophylline C.
Figure 2B:
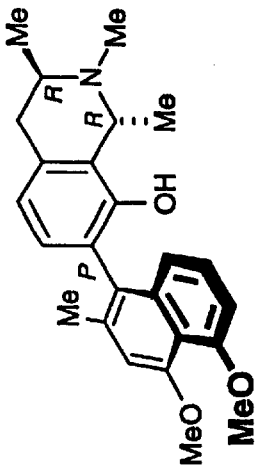
FIG. 2B illustrates the structure of dioncolactone A, N-methyl-dioncophylline A, ancistrobrevine D, and ancistrocladine.
Figure 2B:
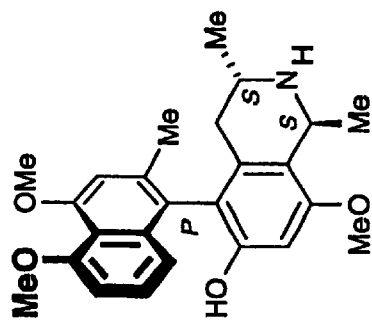
Figure 2B:
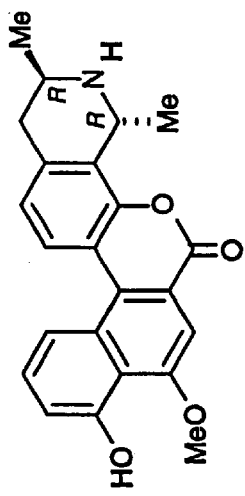
Figure 2B:
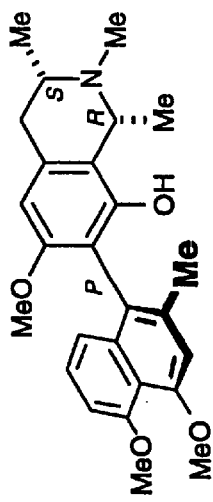
Figure 2C:
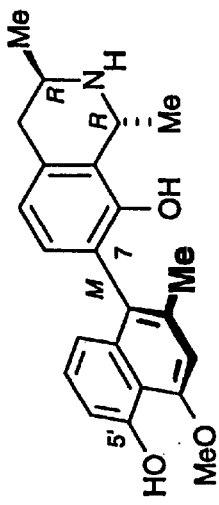
FIG. 2C illustrates the structures of 5'-O-demethyl-8-O-methyl-7-epi-dioncophylline A, 5'-O-demethyl-7-epi-dioncophylline A, dioncophylleine A, and hamatine.
Figure 2C:
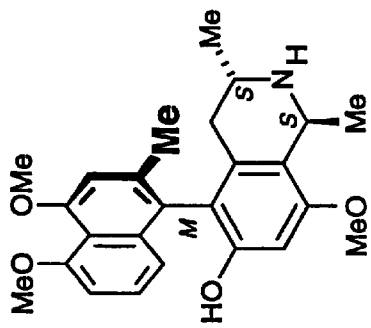
Figure 2C:
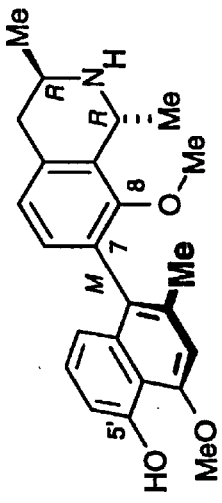
Figure 2C:
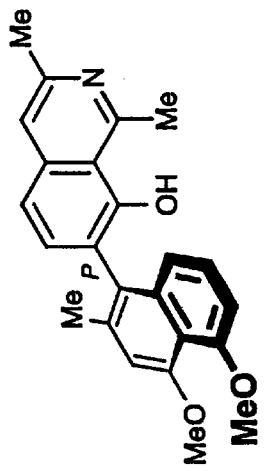
Figure 2D:
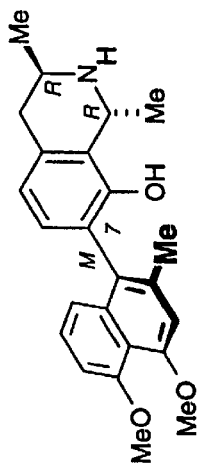
FIG. 2D illustrates the structure of ancistrobarterine A, 7-epi-dioncophylline, A, N-formyl-ancistrocladine, and N-methyl-ancistrocladine.
Figure 2D:
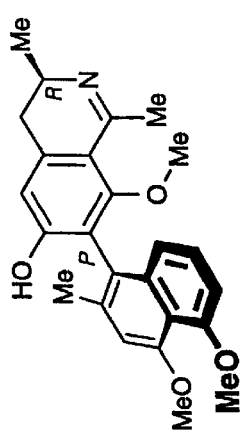
Figure 2D:
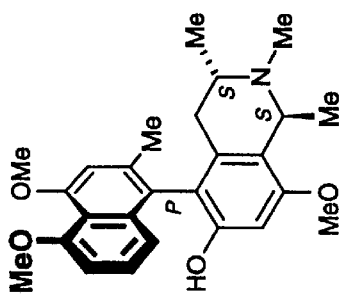
Figure 2D:
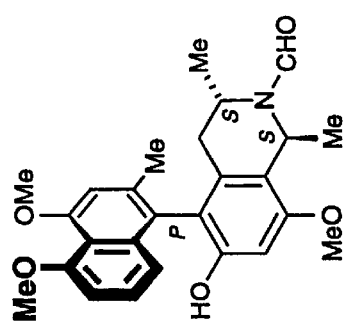
Figure 2E:
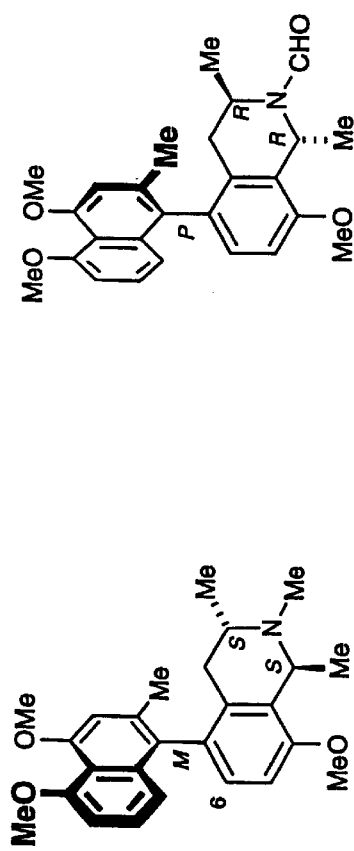
FIG. 2E illustrates the structure of 6-deoxy-N-methyl-ancistrocladine, N-formyl-O,O-dimethyl-dioncophylline C, N-formyl-dioncophylline C, and N-formyl-8-O-benzyl-dioncophylline C.
Figure 2E:
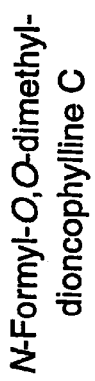
Figure 2E:
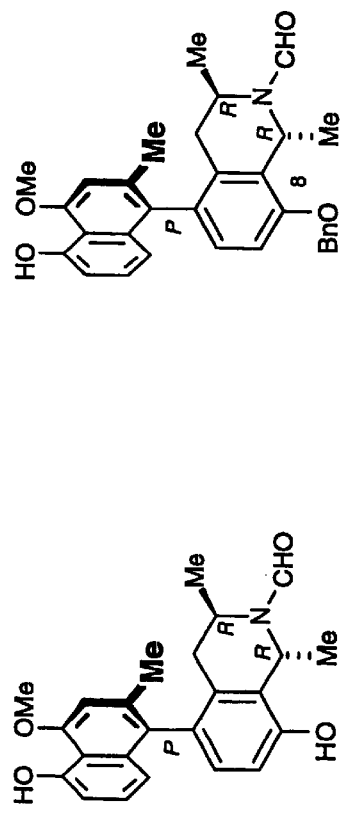
Figure 2E:
Figure 2F:
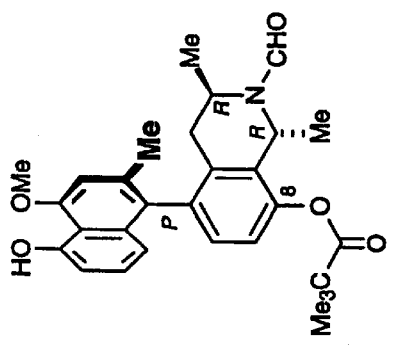
FIG. 2F illustrates the structure of N-formyl-8-O-methyl-dioncophylline C, N-formyl-8-O-pivaloyl-dioncophylline C N-formyl-8-O-acetyl-dioncophylline C, and N-formyl-8-O-benzoyl-dioncophylline C.
Figure 2F:
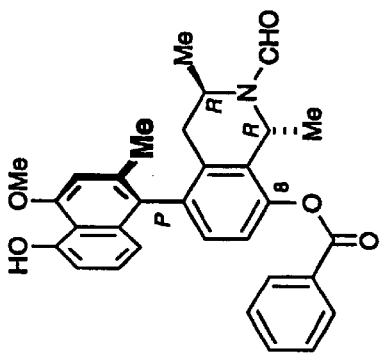
Figure 2F:
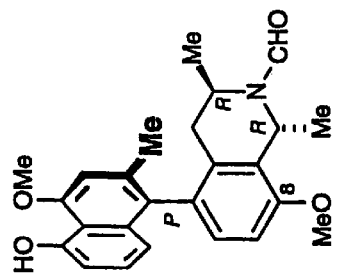
Figure 2F:
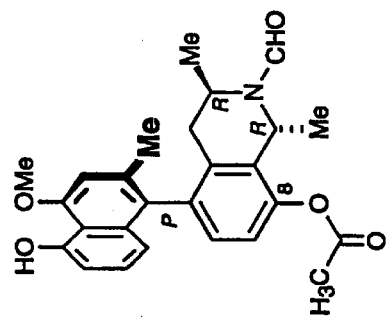
Figure 2G:
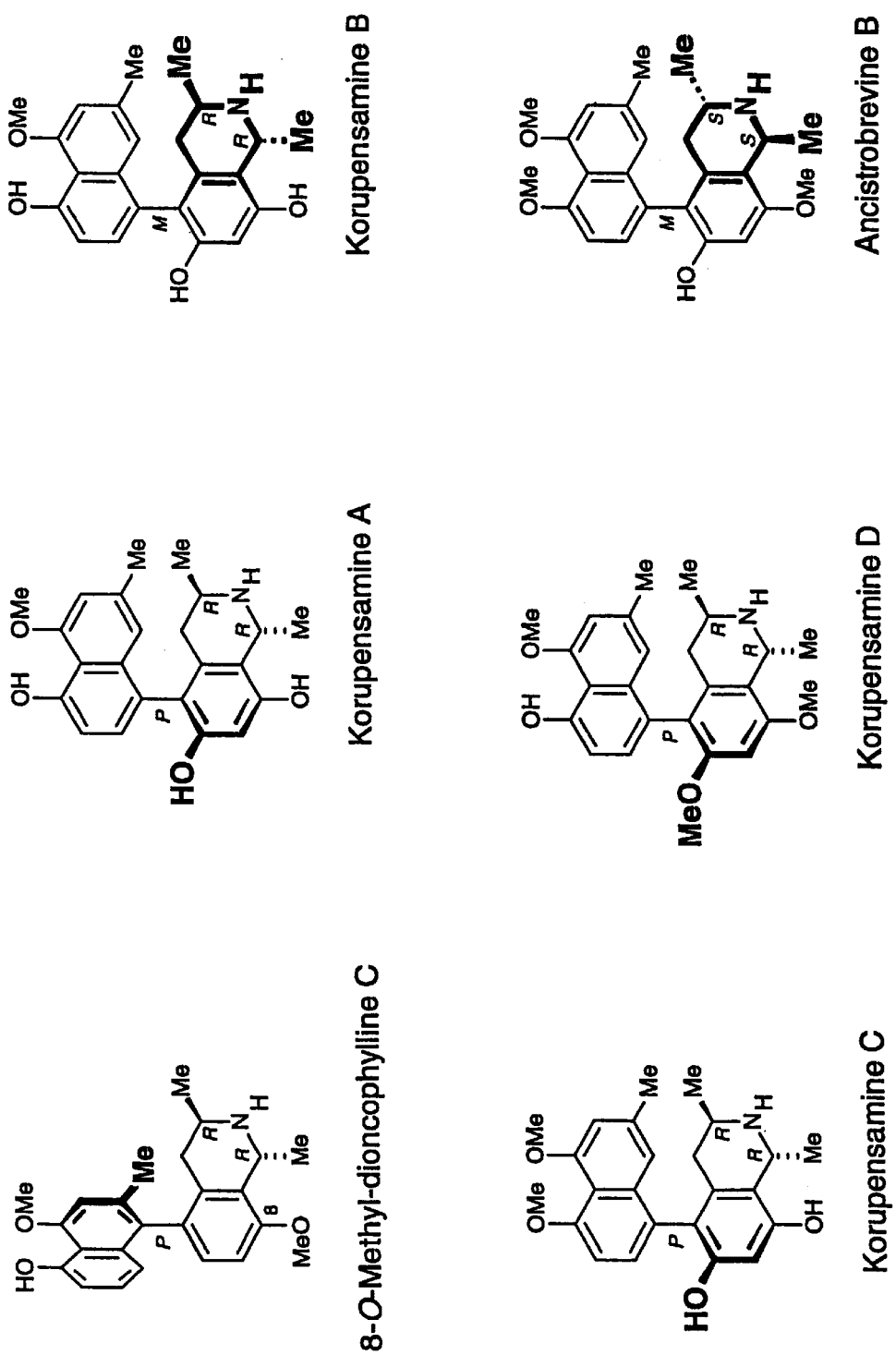
FIG. 2G illustrates the structure of 8-O-methyl-dioncophylline C, korupensamine A, korupensamine B, korupensamine C, korupensamine D, and ancistrobrevine B.

Heretofore the only reported monomeric arylisoquinoline alkaloid compounds known to contain a C-8' to C-7 naphthalene/isoquinoline linkage were dioncophylline D, ancistrobrevine A, 6-O-demethyl-ancistrobrevine A, yaoundamine A, yaoundamine B, and ancistroheynine A (FIGS. 1A–1B). These compounds were originally isolated and purified from plants of the Dioncophyllaceae and Ancistrocladaceae families (Bringmann and Pokorny, The Alkaloids, Vol. 46 (G. Cordell, ed.), Academic Press, New York, 1995, p. 151, pp. 163–164); Hallock et al., *Tetrahedron*, 53, 8121–8128 (1997); Bringmann et al., *Phytochem.*, 43, 1405–1410 (1996)). Furthermore, the only reported monomeric naphthylisoquinoline alkaloids known to contain any substituent other than a hydrogen at the C-4 position of the isoquinoline ring are the dioncophyllacines A and B (FIG. 1B), wherein the isoquinoline ring is fully aromatic (Bringmann and Pokorny, The Alkaloids, Vol. 46 (G. Cordell, ed.), Academic Press, New York, 1995, pp. 152–154). There has been no literature report of any dimeric arylisoquinoline alkaloid wherein either or both molecular half (halves) comprise a compound of the present invention.

The present invention provides useful new monomeric and dimeric arylisoquinoline alkaloid derivatives containing the C-8' to C-7 naphthalene/isoquinoline linkage. It is another object of the present invention to provide useful new monomeric and dimeric arylisoquinoline alkaloid derivatives containing substituent(s) other than hydrogen at the C-4 position(s) of the isoquinoline ring(s). Specifically excluded from the compounds of the present invention are the previously disclosed monomeric compounds: dioncophylline D, ancistrobrevine A, 6-O-demethylancistrobrevine A, yaoundamine A, yaoundamine B, ancistroheynine A, dioncophyllacine A, and dioncophyllacine B (FIGS. 1A–1B). Also specifically excluded from the present invention are other known (Bringmann and Porkorny, The Alkaloids, Vol. 46 (G. Cordell, ed.), Academic Press, New York, 1995, pp. 127–271) monomeric arylisoquinoline alkaloid compounds illustrated in FIGS. 2A–2G.

Compounds of the present invention comprise new monomeric and dimeric derivatives of dioncophylline D as well as new monomeric and dimeric derivatives of the other compounds shown in FIGS. 1–2. The monomeric compounds of the present invention are useful as synthetic intermediates or building blocks for making useful new dimeric arylisoquinoline alkaloid compounds. Furthermore, the monomeric as well as the dimeric compounds of the present invention have medically useful and other useful properties, particularly including antimalarial and antiviral properties.

Structures

To make it easier to compare arylisoquinoline alkaloids of the present invention of different coupling types, contrary to IUPAC numbering conventions, and consistent with previous work by the inventors (Bringmann and Pokorny, The Alkaloids, Vol. 46 (G. Cordell, ed.) Academic Press, New York, 1995, pp. 127–271), the naphthalene portion of the alkaloids is hereinafter numbered in the same way. In other words, there is always attributed a 2-methyl-4,5-dioxy-substitution pattern to the naphthalene, independent from the site of the axis.

Definitions

For clarification of the chemical structures described herein, the following definitions apply.

By arylisoquinoline homodimer is meant a dimeric alkaloid containing two monomeric arylisoquinoline halves, wherein each half is the same.

By arylisoquinoline heterodimer is meant a dimeric alkaloid containing two monomeric arylisoquinoline halves, wherein each half is different.

By $C_1$–$C_6$ alkyl is meant straight or branched-chain $C_1$–$C_6$ alkyl groups. Examples include, but are not limited to, methyl, ethyl, n-propyl, isopropyl, n-butyl, isobutyl, sec-butyl, tertiary-butyl, n-pentyl, isopentyl, and n-hexyl.

By aryl is meant an organic radical derived from an aromatic hydrocarbon. Examples of aryl groups include but are not limited to phenyl, o-, m-, and p-hydroxyphenyl, and naphthyl.

By aliphatic is meant an organic radical derived from an open straight or branched hydrocarbon chain. Examples of aliphatic radicals include alkanes, alkenes, and alkynes. Specific examples of aliphatic radicals which can be used in the present invention include, but are not limited to, $C_1$–$C_6$ alkyl radicals, straight or branched.

Medical and Other Uses

The new dimeric arylisoquinoline alkaloids and derivatives thereof are expected to have at least those medicinal properties possessed by previously disclosed monomeric and dimeric naphthylisoquinoline alkaloids (see, e.g., Boyd et al., U.S. Pat. No. 5,455,251; Francois et al., U.S. Pat. No. 5,639,761). However, depending upon the particular disease and host to be treated, a compound of the present invention will be distinctly advantageous in a given situation.

Medically useful properties of the compounds of the present invention can be readily confirmed by one knowledgeable and skilled in the art by use of any of a variety of methods which have been published or otherwise disclosed elsewhere. For example, antiviral properties, particularly anti-HIV properties, can be confirmed as described in Boyd et al., U.S. Pat. No. 5,455,251. Also, for example, in vitro and in vivo antimalarial activity may be confirmed as described in Francois et al., U.S. Pat. No. 5,639,761 and Boyd et al., U.S. Pat. No. 5,409,938.

The compounds of the present invention also are useful in a variety of in vitro applications. Such in vitro applications include biochemical assays, as well as chemical syntheses and viral research.

The compounds of the present invention are also useful as synthetic intermediates for the preparation of monomeric and dimeric arylisoquinoline alkaloids.

Preparation, Isolation, and Purification

One skilled in the art will readily appreciate that, based upon prior disclosures, and in conjunction with other now well-established methods and procedures, compounds of the present invention can be obtained, purified, and provided in substantially pure form from natural sources, particularly from plants of the Dioncophyllaceae and Ancistrocladaceae families, and/or can be prepared by chemical modification(s) or derivatization(s) of naturally occurring arylisoquinoline alkaloids (Boyd et al., U.S. Pat. No. 5,455,251; Boyd et al., U.S. Pat. No. 5,654,432; Francois et al, U.S. Pat. No. 5,639,761; Boyd et al, U.S. Pat. No. 5,409,938; Bringmann and Pokorny, The Alkaloids, Vol. 46 (G. Cordell, ed.), Academic Press, New York, 1995, pp. 127–271). Chemical structures of isolated and purified compounds of the present invention can be elucidated and/or verified by a variety of procedures, particularly spectroanalytical procedures, well-known to experienced practitioners of the art. Example 1 describes the isolation and purification, from a plant, of exemplary compounds of the present invention. Example 2 describes the detailed structure proof of an exemplary compound of the present invention.

In addition to isolation, purification and derivatization of compounds from natural sources, compounds of the present invention can be obtained by partial and/or total synthesis. For instance, one skilled in the art will readily appreciate that, based upon prior disclosures (Bringmann et al., U.S. Pat. No. 5,571,919; Bringmann et al., U.S. Pat. No. 5,552,550; Bringmann et al, U.S. patent application Ser. No. 08/721,084; Bringmann and Pokorny, The Alkaloids, Vol. 46 (G. Cordell, ed.), Academic Press, New York, 1995, pp.

127–271), monomeric and dimeric compounds of the present invention can be chemically synthesized using naturally occurring and/or fully synthetic precursors, intermediates or building blocks. Example 4 illustrates partial and total synthesis strategies for preparing exemplary monomeric compounds of the present invention using approaches defined in previous disclosures and in conjunction with other now well-established reactions and procedures (Bringmann et al., U.S. Pat. No. 5,552,550; Bringmann and Pokorny, The Alkaloids, Vol. 46 (G. Cordell, ed.), Academic Press, New York, 1995, pp. 127–271). Example 5 illustrates partial and total synthesis strategies for preparing exemplary dimeric compounds of the present invention using approaches defined in previous disclosures and in conjunction with other well-established reactions and procedures (Bringmann et al., U.S. Pat. No. 5,571,919; Bringmann et al., U.S. Pat. No. 5,578,729; Bringmann et al., U.S. patent application Ser. No. 08/721,084; Bringmann and Pokorny, The Alkaloids, Vol. 46 (G. Cordell, ed.), Academic Press, New York, 1995, pp. 127–271).

The Present Inventive Compounds

Accordingly, the present invention provides useful new monomeric derivative compounds of dioncophylline D, wherein at least one or more of the following modifications is incorporated: the configuration at C-1 or C-3 is instead S; one or more phenolic hydroxyl group(s) is (are) instead ester, sulfonate ester, or ether group(s); the methyl ether group is instead a phenolic hydroxyl group; one or more phenolic hydroxyl group(s) is (are) instead (an) aromatic hydrogen substituent(s); the secondary amine site is instead an amide, sulfonamide, tertiary amine, alkyl quaternary ammonium salt or corresponding Hoffmann elimination product thereof; one or more aromatic hydrogen substituent (s) is (are) instead halo, nitro, amino, hydroxyl, acyloxy, alkoxy, aryloxy, glycosyloxy, thiol or cyano; at least one $CH_3$ is instead H; a tetrahydroisoquinoline is instead a dihydroisoquinoline.

The present invention further provides useful new monomeric derivative compounds of dioncophylline D, ancistrobrevine A, 6-O-demethyl-ancistrobrevine A, yaoundamine A, yaoundamine B, ancistroheynine A, dioncophylline B, dioncopeltine A, dioncophylline A, dioncophylline C, dioncolactone A, N-methyl-dioncophylline A, ancistrobrevine D, ancistrocladine, 5'-O-demthyl-8-O-methyl-7-epi-dioncophylline A, 5'-O-demthyl-7-epi-dioncophylline A, hamatine, ancistrobarterine A, 7-epi-dioncophylline A, N-formyl-ancistrocladine, N-methyl-ancistrocladine, 6-deoxy-N-methyl-ancistrocladine, N-formyl-O,O-dimethyl-dioncophylline C, N-formyl-dioncophylline C, N-formyl-8-O-benzyl-dioncophylline C, N-formyl-8-O-methyl-dioncophylline C, N-formyl-8-O-pivaloyl-dioncophylline C, N-formyl-8-O-acetyl-dioncophylline C, N-formyl-8-O-benzoyl-dioncophylline C, and 8-O-methyl-dioncophylline C, wherein: (a) the configurations at C-1 and C-3 are the same or different, and each is R or S; the configuration about the naphthalene/isoquinoline axis is P or M, or may be configuratively unstable; one or more phenolic hydroxyl group(s) may instead be an ester, sulfonate ester, or ether group; one or more methyl ether group(s) may instead be a phenolic hydroxyl group; one or more phenolic hydroxyl group(s) may instead be an aromatic hydrogen substituent; one or more secondary amine site(s) may instead be an amide, sulfonamide, tertiary amine, alkyl quaternary ammonium salt or corresponding Hoffmann elimination product thereof, one or more tertiary amine site(s) may instead be a secondary amine; one or more aromatic hydrogen substituent(s) may instead be $C_1–C_6$ alkyl, acyl, halo, nitro, amino, hydroxyl, acyloxy, alkoxy, aryloxy, glycosyloxy, thiol or cyano; at least one $CH_3$ may instead be H; a tetrahydroisoquinoline may instead be a dihydroisoquinoline; and (b) a substituent at C-4 is $C_1–C_6$ alkyl, halo, nitro, amino, hydroxyl, acyloxy, alkoxy, aryloxy, glycosyloxy, thiol, cyano or oxo.

The present invention further provides new monomeric derivative compounds of dioncophylline D, ancistrobrevine A, 6-O-demethyl-ancistrobrevine A, yaoundamine A, yaoundamine B, ancistroheynine A, dioncophyllacine A, dioncophyllacine B, dioncophylline B, dioncopeltine A, dioncophylline A, dioncophylline C, dioncolactone A, N-methyl-dioncophylline A, ancistrobrevine D, ancistrocladine, 5'-O-demethyl-8-O-methyl-7-epi-dioncophylline A, 5'-O-demethyl-7-epi-dioncophylline A, dioncophylleine A, hamatine, ancistrobarterine A, 7-epi-dioncophylline A, N-formyl ancistrocladine, N-methyl-ancistrocladine, 6-deoxy-N-methyl-ancistrocladine, N-formyl-O, O-dimethyl-dioncophylline C, N-formyl-dioncophylline C, N-formyl-8-O-benzyl-dioncophylline C, N-formyl-8-O-methyl-dioncophylline C, N-formyl-8-O-pivaloyl-dioncophylline C, N-formyl-8-O-acetyl-dioncophylline C, N-formyl-8-O-benzoyl-dioncophylline C, and 8-O-methyl-dioncophylline C, wherein: (a) the configurations at C-1 and C-3 are the same or different, and each is R or S; the configuration about the naphthalene/isoquinoline axis is P or M, or may be configuratively unstable; one or more phenolic hydroxyl group(s) may instead be an ester, sulfonate ester, or ether group; one or more methyl ether group(s) may instead be a phenolic hydroxyl group; one or more phenolic hydroxyl group(s) may instead be an aromatic hydrogen substituent; one or more secondary amine site(s) may instead be an amide, sulfonamide, tertiary amine, alkyl quaternary ammonium salt or corresponding Hoffmann elimination product thereof, one or more tertiary amine site(s) may instead be a secondary amine; one or more aromatic hydrogen substituent(s) may instead be $C_1–C_6$ alkyl, acyl, halo, nitro, amino, hydroxyl, acyloxy, alkoxy, aryloxy, glycosyloxy, thiol or cyano; (b) the isoquinoline is a fully aromatic isoquinoline; and (c) a substituent at C-4 is acyloxy, alkoxy, aryloxy, glycosyloxy or oxo.

The present invention further provides useful new monomeric derivative compounds of korupensamine A, korupensamine B, korupensamine C, korupensamine D, and ancistrobrevine B, wherein: (a) the configurations at C-1 and C-3 are the same or different, and each is R or S; the configuration about the naphthalene/isoquinoline axis is P or M, or may be configuratively unstable; one or more phenolic hydroxyl group(s) may instead be an ester, sulfonate ester, or ether group; one or more methyl ether group(s) may instead be a phenolic hydroxyl group; one or more phenolic hydroxyl group(s) may instead be an aromatic hydrogen substituent; one or more secondary amine site(s) may instead be an amide, sulfonamide, tertiary amine, alkyl quaternary ammonium salt or corresponding Hoffmann elimination product thereof, one or more tertiary amine site(s) may instead be a secondary amine; one or more aromatic hydrogen substituent(s) may instead be halo, nitro, amino, hydroxyl, acyloxy, alkoxy, aryloxy, glycosyloxy, thiol or cyano; and (b) a substituent at C-4 is $C_1–C_6$ alkyl, halo, nitro, amino, hydroxyl, acyloxy, alkoxy, aryloxy, glycosyloxy, thiol, cyano or oxo.

The present invention further provides useful new monomeric derivative compounds of korupensamine A, korupensamine B, korupensamine C, korupensamine D, and ancistrobrevine B wherein: (a) the configurations at C-1 and C-3 are the same or different, and is be R or S; the configuration about the naphthalene/isoquinoline axis is P or M, or may be configuratively unstable; one or more phenolic hydroxyl group(s) may instead be an ester, sulfonate ester, or ether group; one or more methyl ether group(s) may instead be a phenolic hydroxyl group; one or more phenolic hydroxyl group(s) may instead be an aromatic hydrogen substituent; one or more secondary amine site(s) may instead be an amide, sulfonamide, tertiary amine, alkyl quaternary ammonium salt or corresponding Hoffmann elimination product thereof, one or more tertiary amine site(s) may instead be a secondary amine; one or more aromatic hydrogen substituent(s) may instead be $C_1-C_6$ alkyl, acyl, halo, nitro, amino, hydroxyl, acyloxy, alkoxy, aryloxy, glycosyloxy, thiol or cyano; at least one $CH_3$ may instead be H; the tetrahydroisoquinoline may instead be a dihydroisoquinoline or a fully aromatic isoquinoline; (b) a substituent at C-4 is acyloxy, alkoxy, aryloxy, glycosyloxy or oxo; and (c) at least one aromatic hydrogen substituent is instead an acyl or $C_1-C_6$ alkyl, and/or a substituent at C-2' cannot be methyl when substituents at C-1 and C-3 are both methyl.

The present invention further provides useful new dimeric arylisoquinoline alkaloids comprised of coupled first and second arylisoquinoline monomers, wherein either or both of said monomer(s) is (are) monomeric compound(s) of the present invention.

The present invention further provides 4-substituted monomeric arylisoquinolines of the formula:

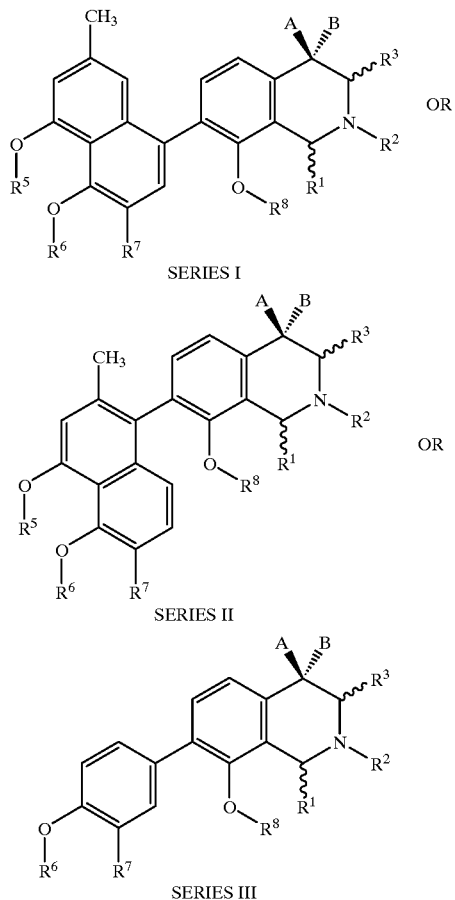

SERIES I

SERIES II

SERIES III wherein either A or B can be any suitable substituent or precursor thereof, preferably $C_1-C_6$ alkyl, acyl, aryl, halo, nitro, amino, azido, hydroxyl, acyloxy, alkoxy, aryloxy, glycosyloxy, thiol or cyano; or A and B together form a keto group (=O), a thio group (=S), or a ketal of the formula —O(CH$_2$)$_n$O—, wherein n is an integer from 2–4; $R^2$ can be any suitable N-terminal substituent on the isoquinoline ring, preferably H, $C_1-C_6$ alkyl, an amide, or sulfonamide; $R^1$ and $R^3$ are the same or different, preferably H or $C_1-C_3$ alkyl, more preferably ◀■H, ⋯⋯∥H, ◀■CH$_3$, or ⋯⋯∥CH$_3$; $R^5$, $R^6$, and $R^8$ are the same or different and each is H, $C_1-C_6$ alkyl, arylmethyl, or aryl, preferably H or $C_1-C_6$ alkyl; one or more aromatic hydrogen substituent(s) may instead be any functional group or organic radical, preferably $C_1-C_6$ alkyl, acyl, halo, nitro, amino, hydroxyl, acyloxy, alkoxy, aryloxy, glycosyloxy, thiol or cyano; the tetrahydroisoquinoline ring may instead be a dihydroisoquinoline ring or a fully aromatic isoquinoline ring; and $R^7$ can be any functional group, preferably selected from the group consisting of H, $C_1-C_6$ alkyl, acyl, halo, nitro, amino, hydroxyl, acyloxy, alkoxy, aryloxy, glycosyloxy, thiol, and cyano.

The present invention further provides 4-substituted dimeric arylisoquinolines of the formula:

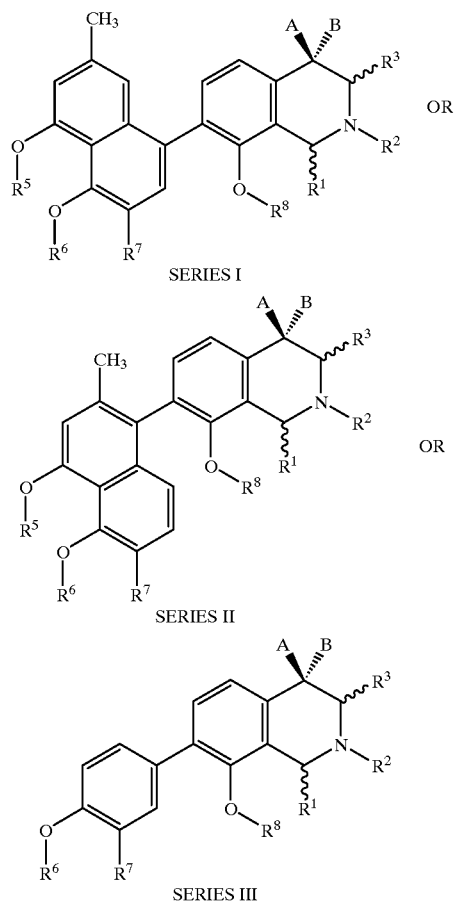

SERIES I

SERIES II

SERIES III wherein either A or B can be any suitable substituent or precursor thereof, preferably $C_1-C_6$ alkyl, acyl, aryl, halo, nitro, amino, azido, hydroxyl, acyloxy, alkoxy, aryloxy, glycosyloxy, thiol or cyano; or A and B together form a keto group (=O), a thio group (=S), or a ketal of the formula —O(CH$_2$)$_n$O—, wherein n is an integer from 2–4; $R^2$ can be any suitable N-terminal substituent on the isoquinoline ring, preferably H, $C_1-C_6$ alkyl, an amide, or sulfonamide; $R^1$ and $R^3$ are the same or different, preferably H or $C_1-C_3$ alkyl, more preferably ◀■H, ⋯⋯∥H, ◀■CH$_3$; or ⋯⋯∥CH$_3$; $R^5$, $R^6$, and $R^8$ are the same or different and each is H, $C_1-C_6$ alkyl, arylmethyl, or aryl, preferably H or $C_1-C_6$ alkyl; one or more aromatic hydrogen substituent(s) may instead be any functional group or organic radical, preferably $C_1$–$C_6$ alkyl, acyl, halo, nitro, amino, hydroxyl, acyloxy, alkoxy, aryloxy, glycosyloxy, thiol or cyano; the tetrahydroisoquinoline ring may instead be a dihydroisoquinoline ring or a fully aromatic isoquinoline ring; and $R^7$ is arylisoquinoline of the formula:

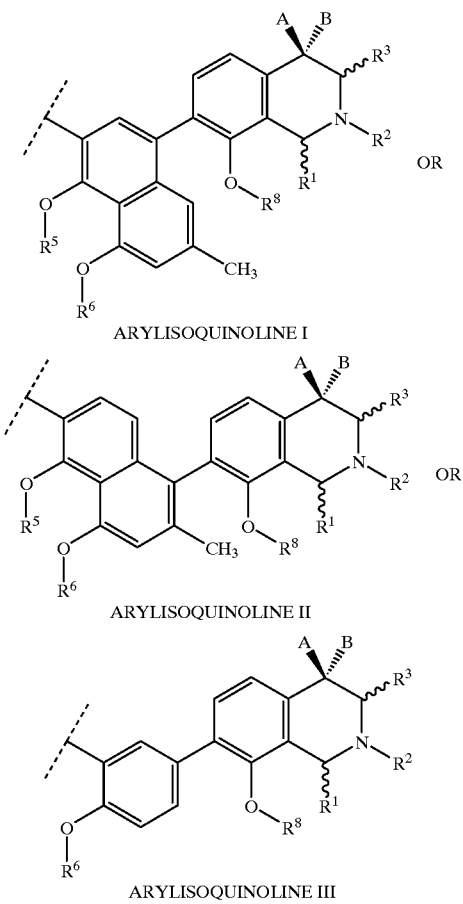

ARYLISOQUINOLINE I

ARYLISOQUINOLINE II

ARYLISOQUINOLINE III wherein either A or B can be any suitable substituent or precursor thereof, preferably $C_1$–$C_6$ alkyl, acyl, aryl, halo, nitro, amino, azido, hydroxyl, acyloxy, alkoxy, aryloxy, glycosyloxy, thiol or cyano; or A and B are both H or together form a keto group (=O), a thio group (=S), or a ketal of the formula —O$(CH_2)_n$O—, wherein n is an integer from 2–4; $R^2$ can be any suitable N-terminal substituent on the isoquinoline ring, preferably H, $C_1$–$C_6$ alkyl, an amide, or sulfonamide; $R^1$ and $R^3$ are the same or different, preferably H or $C_1$–$C_3$ alkyl, more preferably ◄H, ⋯⋯H, ◄$CH_3$; or ⋯⋯$CH_3$;

$R^5$, $R^6$, and R8 are the same or different and each is H, $C_1$–$C_6$ alkyl, arylmethyl, or aryl, preferably H or $C_1$–$C_6$ alkyl; one or more aromatic hydrogen substituent(s) may instead be any functional group or organic radical, preferably $C_1$–$C_6$ alkyl, acyl, halo, nitro, amino, hydroxyl, acyloxy, alkoxy, aryloxy, glycosyloxy, thiol or cyano; and the tetrahydroisoquinoline ring may instead be a dihydroisoquinoline ring or a fully aromatic isoquinoline ring.

The present invention further provides 4-substituted dimeric arylisoquinolines of the formula:

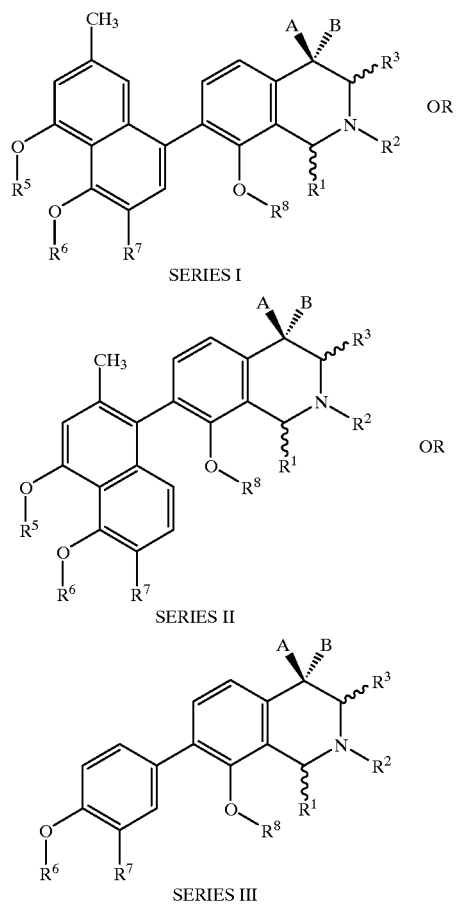

SERIES I

SERIES II

SERIES III wherein either A or B can be any suitable substituent or precursor thereof, preferably $C_1$–$C_6$ alkyl, acyl, aryl, halo, nitro, amino, azido, hydroxyl, acyloxy, alkoxy, aryloxy, glycosyloxy, thiol or cyano; or A and B together form a keto group (=O), a thio group (=S), or a ketal of the formula —O$(CH_2)_n$O—, wherein n is an integer from 2–4; $R^2$ can be any suitable N-terminal substituent on the isoquinoline ring, preferably H, $C_1$–$C_6$ alkyl, an amide, or sulfonamide; $R^1$ and $R^3$ are the same or different, preferably H or $C_1$–$C_3$ alkyl, more preferably ◄H, ⋯⋯H, ◄$CH_3$; ⋯⋯$CH_3$;

$R^5$, $R^6$, and $R^8$ are the same or different and each is H, $C_1$–$C_6$ alkyl, arylmethyl, or aryl, preferably H or $C_1$–$C_6$ alkyl; one or more aromatic hydrogen substituent(s) may instead be any functional group or organic radical, preferably $C_1$–$C_6$ alkyl, acyl, halo, nitro, amino, hydroxyl, acyloxy, alkoxy, aryloxy, glycosyloxy, thiol or cyano; the tetrahydroisoquinoline ring may instead be a dihydroisoquinoline ring or a fully aromatic isoquinoline ring; and $R^7$ is a radical having a structure selected from the group consisting of derivatives of dioncophylline D, wherein the configuration at C-1 or C-3 is instead S; one or more phenolic hydroxyl group(s) is instead an ester, sulfonate ester, or ether group;-a methyl ether group is instead a phenolic hydroxyl group; one or more phenolic hydroxyl group(s) is instead an aromatic hydrogen substituent; the secondary amine site is instead an amide, sulfonamide, tertiary amine, alkyl quaternary ammonium salt or corresponding Hoffmann elimination product thereof; one or more aromatic hydrogen substituent(s) is instead halo, nitro, amino, hydroxyl, acyloxy, alkoxy, aryloxy, glycosyloxy, thiol or cyano; at least one $CH_3$ is instead H; and/or the tetrahydroisoquinoline is instead a dihydroisoquinoline; with the proviso that said derivative is not ancistrobrevine A, 6-O-demethyl-ancistrobrevine A, yaoundamine A, yaoundamine B, or ancistroheynine A.

The present invention further provides 4-substituted dimeric arylisoquinolines of the formula:

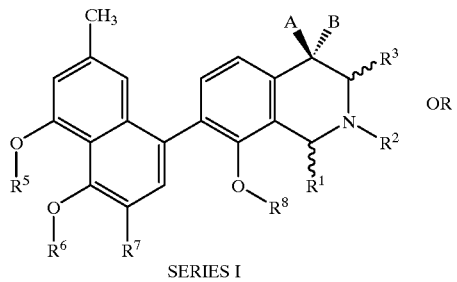

SERIES I

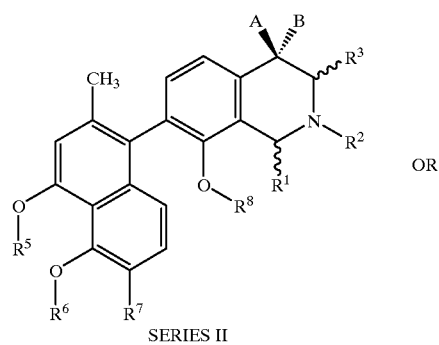

SERIES II

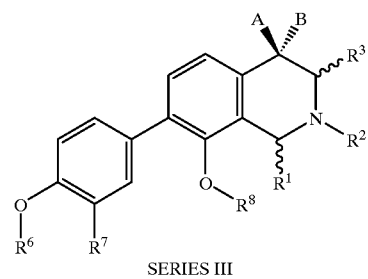

SERIES III wherein either A or B can be any suitable substituent or precursor thereof, preferably $C_1$–$C_6$ alkyl, acyl, aryl, halo, nitro, amino, azido, hydroxyl, acyloxy, alkoxy, aryloxy, glycosyloxy, thiol or cyano; or A and B together form a keto group (=O), a thio group (=S), or a ketal of the formula —O($CH_2$)$_n$O—, wherein n is an integer from 2–4; $R^2$ can be any suitable N-terminal substituent on the isoquinoline ring, preferably H, $C_1$–$C_6$ alkyl, an amide, or sulfonamide; $R^1$ and $R^3$ are the same or different, preferably H or $C_1$–$C_3$ alkyl, more preferably ◂H, ⋯⋯H, ◂$CH_3$; or ⋯⋯$CH_3$;
$R^5$, $R^6$, and $R^8$ are the same or different and each is H, $C_1$–$C_6$ alkyl, arylmethyl, or aryl, preferably H or $C_1$–$C_6$ alkyl; one or more aromatic hydrogen substituent(s) may instead be any functional group or organic radical, preferably $C_1$–$C_6$ alkyl, acyl, halo, nitro, amino, hydroxyl, acyloxy, alkoxy, aryloxy, glycosyloxy, thiol or cyano; the tetrahydroisoquinoline ring may instead be a dihydroisoquinoline ring or a fully aromatic isoquinoline ring; and $R^7$ is a radical selected from the group consisting of derivatives of dioncophylline D, ancistrobrevine A, 6-O-demethyl-ancistrobrevine A, yaoundamine A, yaoundamine B, ancistroheynine A, dioncophylline B, dioncopeltine A, dioncophylline A, dioncophylline C, dioncolactone A, N-methyl-dioncophylline A, ancistrobrevine D, ancistrocladine, 5'-O-demethyl-8-O-methyl-7-epi-dioncophylline A, 5'-O-demethyl-7-epi-dioncophylline A, hamatine, ancistrobarterine A, 7-epi-dioncophylline A, N-formyl ancistrocladine, N-methyl-ancistrocladine, 6-deoxy-N-methyl-ancistrocladine, N-formyl-O,O-dimethyl-dioncophylline C, N-formyl-dioncophylline C, N-formyl-8-O-benzyl-dioncophylline C, N-formyl-8-O-methyl-dioncophylline C, N-formyl-8-O-pivaloyl-dioncophylline C, N-formyl-8-O-acetyl-dioncophylline C, N-formyl-8-O-benzoyl-dioncophylline C, and 8-O-methyl-dioncophylline C, wherein: (a) the configurations at C-1 and C-3 are the same or different, and each is R or S; the configuration about the naphthalene/isoquinoline axis is P or M, one or more phenolic hydroxyl group(s) may instead be an ester, sulfonate ester, or ether group; one or more methyl ether group(s) may instead be a phenolic hydroxyl group; one or more phenolic hydroxyl group(s) may instead be an aromatic hydrogen substituent; one or more secondary amine site(s) may instead be an amide, sulfonamide, tertiary amine, alkyl quaternary ammonium salt or corresponding Hoffmann elimination product thereof, one or more tertiary amine site(s) may instead be a secondary amine; one or more aromatic hydrogen substituent(s) may instead be $C_1$–$C_6$ alkyl, acyl, halo, nitro, amino, hydroxyl, acyloxy, alkoxy, aryloxy, glycosyloxy, thiol or cyano; at least one $CH_3$ may instead be H; the tetrahydroisoquinoline may instead be a dihydroisoquinoline; and (b) a substituent at C-4 is $C_1$–$C_6$ alkyl, halo, nitro, amino, azido, hydroxyl, acyloxy, alkoxy, aryloxy, glycosyloxy, thiol, cyano or oxo.

The present invention further provides 4-substituted dimeric arylisoquinolines of the formula:

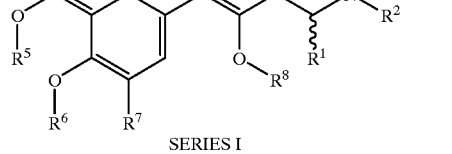

SERIES I

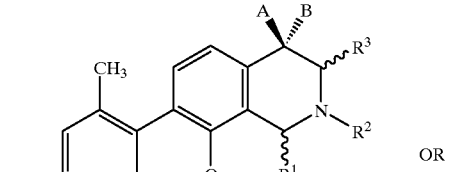

SERIES II

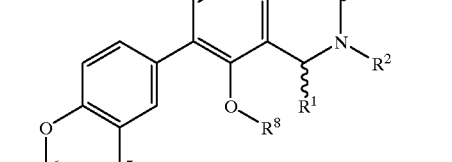

SERIES III wherein either A or B can be any suitable substituent or precursor thereof, preferably $C_1$–$C_6$ alkyl, acyl, aryl, halo, nitro, amino, azido, hydroxyl, acyloxy, alkoxy, aryloxy, glycosyloxy, thiol or cyano; or A and B together form a keto group (=O), a thio group (=S), or a ketal of the formula —O(CH$_2$)$_n$O—, wherein n is an integer from 2–4; R$^2$ can be any suitable N-terminal substituent on the isoquinoline ring, preferably H, C$_1$–C$_6$ alkyl, an amide, or sulfonamide; R$^1$ and R$^3$ are the same or different, preferably H or C$_1$–C$_3$ alkyl, more preferably ◂H, ⋯⋯H, ◂CH$_3$; or ⋯⋯CH$_3$; R$^5$, R$^6$, and R$^8$ are the same or different and each is H, C$_1$–C$_6$ alkyl, arylmethyl, or aryl, preferably H or C$_1$–C$_6$ alkyl; one or more aromatic hydrogen substituent(s) may instead be any functional group or organic radical, preferably C$_1$–C$_6$ alkyl, acyl, halo, nitro, amino, hydroxyl, acyloxy, alkoxy, aryloxy, glycosyloxy, thiol or cyano; the tetrahydroisoquinoline ring may instead be a dihydroisoquinoline ring or a fully aromatic isoquinoline ring; and R$^7$ is a radical having a structure selected from the group consisting of derivatives of dioncophylline D, ancistrobrevine A, 6-O-demthyl-ancistrobrevine A, yaoundamine A, yaoundamine B, ancistroheynine A, dioncophyllacine A, dioncophyllacine B, dioncophylline B, dioncopeltine A, dioncophylline A, dioncophylline C, dioncolactone A, N-methyl-dioncophylline A, ancistrobrevine D, ancistrocladine, 5'-O-demethyl-8-O-methyl-7-epi-dioncophylline A, 5'-O-demethyl-7-epi-dioncophylline A, dioncophylleine A, hamatine, ancistrobarterine A, 7-epi-dioncophylline A, N-formyl ancistrocladine, N-methyl-ancistrocladine, 6-deoxy-N-methyl-ancistrocladine, N-formyl-O, O-dimethyl-dioncophylline C, N-formyl-dioncophylline C, N-formyl-8-O-benzyl-dioncophylline C, N-formyl-8-O-methyl-dioncophylline C, N-formyl-8-O-pivaloyl-dioncophylline C, N-formyl-8-O-acetyl-dioncophylline C, N-formyl-8-O-benzoyl-dioncophylline C, and 8-O-methyl-dioncophylline C, wherein: (a) the configurations at C-1 and C-3 are the same or different, and each is R or S; the configuration about the naphthalene/isoquinoline axis is P or M, one or more phenolic hydroxyl group(s) may instead be an ester, sulfonate ester, or ether group; one or more methyl ether group(s) may instead be a phenolic hydroxyl group; one or more phenolic hydroxyl group(s) may instead be an aromatic hydrogen substituent; one or more secondary amine site(s) may instead be an amide, sulfonamide, tertiary amine, alkyl quaternary ammonium salt or corresponding Hoffmann elimination product thereof, one or more tertiary amine site(s) may instead be a secondary amine; one or more aromatic hydrogen substituent(s) may instead be C$_1$–C$_6$ alkyl, acyl, halo, nitro, amino, hydroxyl, acyloxy, alkoxy, aryloxy, glycosyloxy, thiol or cyano; (b) the isoquinoline is instead a fully aromatic isoquinoline; and (c) a substituent at C-4 is acyloxy, alkoxy, aryloxy, glycosyloxy or oxo; with the proviso that said compound is not dioncophyllacine A or dioncophyllacine B.

The present invention further provides 4-substituted dimeric arylisoquinolines of the formula:

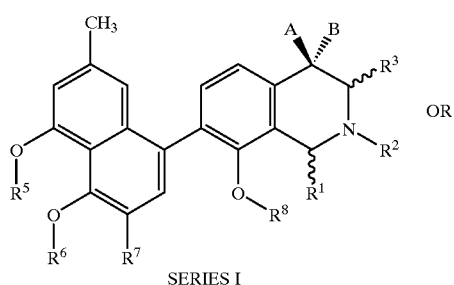

SERIES I

OR

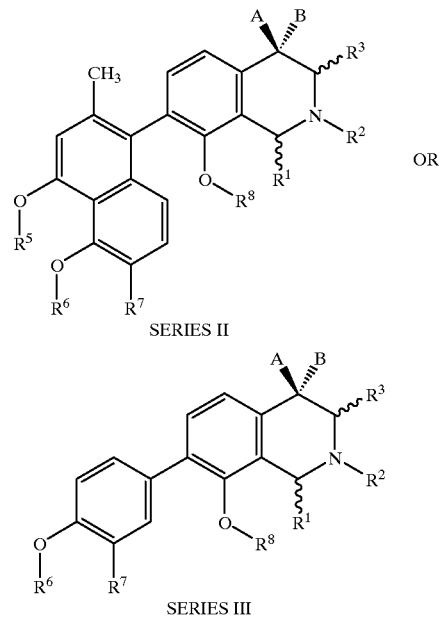

SERIES II

OR

SERIES III wherein either A or B can be any suitable substituent or precursor thereof, preferably C$_1$–C$_6$ alkyl, acyl, aryl, halo, nitro, amino, azido, hydroxyl, acyloxy, alkoxy, aryloxy, glycosyloxy, thiol or cyano; or A and B together form a keto group (=O), a thio group (=S), or a ketal of the formula —O(CH$_2$)$_n$O—, wherein n is an integer from 2–4; R$^2$ can be any suitable N-terminal substituent on the isoquinoline ring, preferably H, C$_1$–C$_6$ alkyl, an amide, or sulfonamide; R$^1$ and R$^3$ are the same or different, preferably H or C$_1$–C$_3$ alkyl, more preferably ◂H, ⋯⋯H, ◂CH$_3$; or ⋯⋯CH$_3$; R$^5$, R$^6$, and R$^8$ are the same or different and each is H, C$_1$–C$_6$ alkyl, arylmethyl, or aryl, preferably H or C$_1$–C$_6$ alkyl; one or more aromatic hydrogen substituent(s) may instead be any functional group or organic radical, preferably C$_1$–C$_6$ alkyl, acyl, halo, nitro, amino, hydroxyl, acyloxy, alkoxy, aryloxy, glycosyloxy, thiol or cyano; the tetrahydroisoquinoline ring may instead be a dihydroisoquinoline ring or a fully aromatic isoquinoline ring; and R$^7$ is a radical having a structure selected from the group consisting of derivatives of korupensamine A, korupensamine B, korupensamine C, korupensamine D, and ancistrobrevine B, wherein: (a) the configurations at C-1 and C-3 are the same or different, and each is R or S; the configuration about the naphthalene/isoquinoline axis is P or M, one or more phenolic hydroxyl group(s) may instead be an ester, sulfonate ester, or ether group; one or more methyl ether group(s) may instead be a phenolic hydroxyl group; one or more phenolic hydroxyl group(s) may instead be an aromatic hydrogen substituent; one or more secondary amine site(s) may instead be an amide, sulfonamide, tertiary amine, alkyl quaternary ammonium salt or corresponding Hoffmann elimination product thereof, one or more tertiary amine site(s) may instead be a secondary amine; one or more aromatic hydrogen substituent(s) may instead be halo, nitro, amino, hydroxyl, acyloxy, alkoxy, aryloxy, glycosyloxy, thiol or cyano; and (b) a substituent at C-4 is C$_1$–C$_6$ alkyl, halo, nitro, amino, hydroxyl, acyloxy, alkoxy, aryloxy, glycosyloxy, thiol, cyano or oxo.

The present invention further provides 4-substituted dimeric arylisoquinolines of the formula:

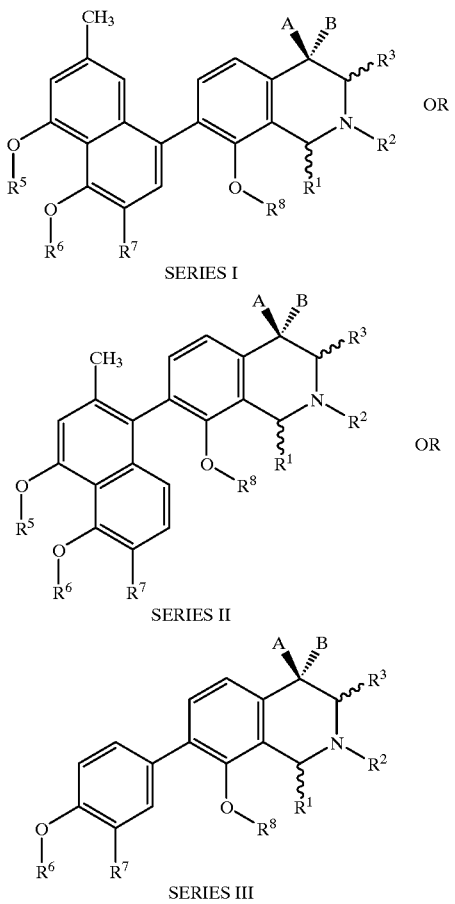

SERIES I

SERIES II

SERIES III wherein either A or B can be any suitable substituent or precursor thereof, preferably $C_1-C_6$ alkyl, acyl, aryl, halo, nitro, amino, azido, hydroxyl, acyloxy, alkoxy, aryloxy, glycosyloxy, thiol or cyano; or A and B together form a keto group (=O), a thio group (=S), or a ketal of the formula —O(CH$_2$)$_n$O—, wherein n is an integer from 2–4; $R^2$ can be any suitable N-terminal substituent on the isoquinoline ring, preferably H, $C_1-C_6$ alkyl, an amide, or sulfonamide; $R^1$ and $R^3$ are the same or different, preferably H or $C_1-C_3$ alkyl, more preferably ◀H, ·····H, ◀CH$_3$; or ·····CH$_3$; $R^5$, $R^6$, and $R^8$ are the same or different and each is H, $C_1-C_6$ alkyl, arylmethyl, or aryl, preferably H or $C_1-C_6$ alkyl; one or more aromatic hydrogen substituent(s) may instead be any functional group or organic radical, preferably $C_1-C_6$ alkyl, acyl, halo, nitro, amino, hydroxyl, acyloxy, alkoxy, aryloxy, glycosyloxy, thiol or cyano; the tetrahydroisoquinoline ring may instead be a dihydroisoquinoline ring or a fully aromatic isoquinoline ring; and $R^7$ is a radical having a structure selected from the group consisting of derivatives of korupensamine A, korupensamine B, korupensamine C, korupensamine D, and ancistrobrevine B, wherein: (a) the configurations at C-1 and C-3 are the same or different, and each is R or S; the configuration about the naphthalene/isoquinoline axis is P or M, one or more phenolic hydroxyl group may instead be an ester, sulfonate ester, or ether group; one or more methyl ether group may instead be a phenolic hydroxyl group; one or more phenolic hydroxyl group may instead be an aromatic hydrogen substituent; one or more secondary amine site may instead be an amide, sulfonamide, tertiary amine, alkyl quaternary ammonium salt or corresponding Hoffmann elimination product thereof, one or more tertiary amine site may instead be a secondary amine; one or more aromatic hydrogen substituent may instead be $C_1-C_6$ alkyl, acyl, halo, nitro, amino, hydroxyl, acyloxy, alkoxy, aryloxy, glycosyloxy, thiol or cyano; at least one CH$_3$ may instead be H; the tetrahydroisoquinoline may instead be a dihydroisoquinoline or a fully aromatic isoquinoline; (b) a substituent at C-4 is acyloxy, alkoxy, aryloxy, glycosyloxy or oxo; and (c) at least one aromatic hydrogen substituent is instead an acyl or $C_1-C_6$ alkyl, and/or a substituent at C-2' is not methyl when C-1 and C-3 are each substituted with a methyl.

Compositions

The present invention further provides compositions comprising one or more of the present inventive compounds and a carrier therefor. With respect to medical uses, the present inventive composition will be a parmaceutical composition, the present inventive compound will be present in a therapeutic or prophylatic amount, and the carrier will be a pharmaceutically acceptable carrier.

EXAMPLES

The following examples further illustrate the present invention but, of course, should not be construed as in any way limiting its scope.

In the following examples, IR spectra were recorded on a Perkin-Elmer 1420 infrared spectrophotometer. Mass spectra were measured at 70 eV on a Finnigan MAT 8200 or on a Varian MAT CH7 mass spectrometer. $^1$H and $^{13}$C NMR spectra were recorded on a Bruker DMX 600 spectrometer using CD$_3$OD ($\delta$3.33 ppm) as the internal reference. HPLC purifications were carried out with a Waters 600E pump, a Nova-Pak C$_{18}$ (Waters, 200×25 mm, 6 μm, integrated guard pak) column, and a Waters 996 photodiode array detector.

*Triphyophyllum peltatum* plants were collected and identified by L. Aké Assi in November, 1991, and by L. Aké Assi and G. Bringmann in March, 1996 in the Parc de Taï, West Ivory Coast. Herbarium specimens of these collections were placed on deposit at the Centre National de Floristique, Abidjan, Ivory Coast, and at the Institut für Organische Chemie, Würzburg, Germany.

Example 1

This example illustrates the procedure for isolation and purification of a compound of the present invention. Dried leaves of *T. peltatum* (40 g) were powdered and macerated for 2 days with 400 mL MeOH/1 N HCl (1:1 v/v) at room temperature with ultrasonic assistance. After removal of the MeOH, the aqueous residue was re-extracted with 1.5 L of chloroform to yield 180 mg of a brownish crude extract, which was chromatographed over silica gel (60 g, deactivated with 7.5% NH$_3$) using CH$_2$Cl$_2$/MeOH (95:5) as the eluent to yield a fraction of 22 mg containing the new compound. Further purification was done by semipreparative HPLC using a Nova-Pak C$_{18}$ (200×25 mm, 6 μm) column with MeOH/H$_2$O (6:2) as the eluent to give 6 mg (0.015%) of a yellow solid, mp 209° C.; $\alpha_D^{25}$+17° (c=0.046, CHCl$_3$), IR (KBr) 3395, 3195, 3000, 1660, 1410, 1190, 1110 cm$^{-1}$; $^1$mH NMR (CD$_3$OD, 600 MHZ) $\delta$7.32 (1H, d, J=8.6 Hz, 6'-H), 7.27 (1H, d, J=8.6 Hz, 7'-H), 7.25 (1H, d J=8.1 Hz, 6-H), 7.24 (1H, s, 1$^1$-H), 7.00 (1H, d, J=8.1 Hz, 5-H), 6.85 (1H, d, J=0.9, Hz, 3'-H), 4.66 (1H, q, J=6.8 Hz, 1-H), 4.50 (1H, d, J=2.2 Hz), 4.08 (3H, s, 4'-OCH$_3$), 3.66 (1H, dq, J=2.2 Hz, 6.7 Hz, 3-H), 2.47 (3H, s, 2'-CH$_3$), 1.60 (3H, d, J=6.8 Hz, 1-CH$_3$), 1.42 (3H, d, J=6.7 Hz, 3-CH$_3$); $^{13}$C NMR (CD$_3$OD, 150 MHZ) $\delta$15.09 (3-CH$_3$), 17.21 (1-CH$_3$) 21.89 (2'-CH$_3$), 49.79 (3-C), 50.17 (1-C), 56.93 (4'-OCH$_3$), 67.07 (4-C), 108.40 (3'-C), 114.31 (4a'-C), 118.91 (8a'-C), 120.45 (6'-C), 121.69 (1'-C), 122.23 (8a-C), 122.78 (5-C), 128.58

(7-C), 131.20 (7'-C), 132.60 (6-C), 135.66 (5a'-C), 138.15, 138.22 (8'-C, 2'-C), 151.60 (8-C), 151.72 (5'-C), 157.51 (4'-C); MS m/z (rel. int.) 379 (M+, 10.7), 364 (M—$CH_3$, 100), 348 (M—$OCH_3$, 11); HRMS m/z 379.177 (M+, $C_{23}H_{25}O_4N$, requires 379.178). These and other spectroanalytical data and analyses were used to elucidate the identity of this isolated and purified compound.

Example 2

Figure 4:
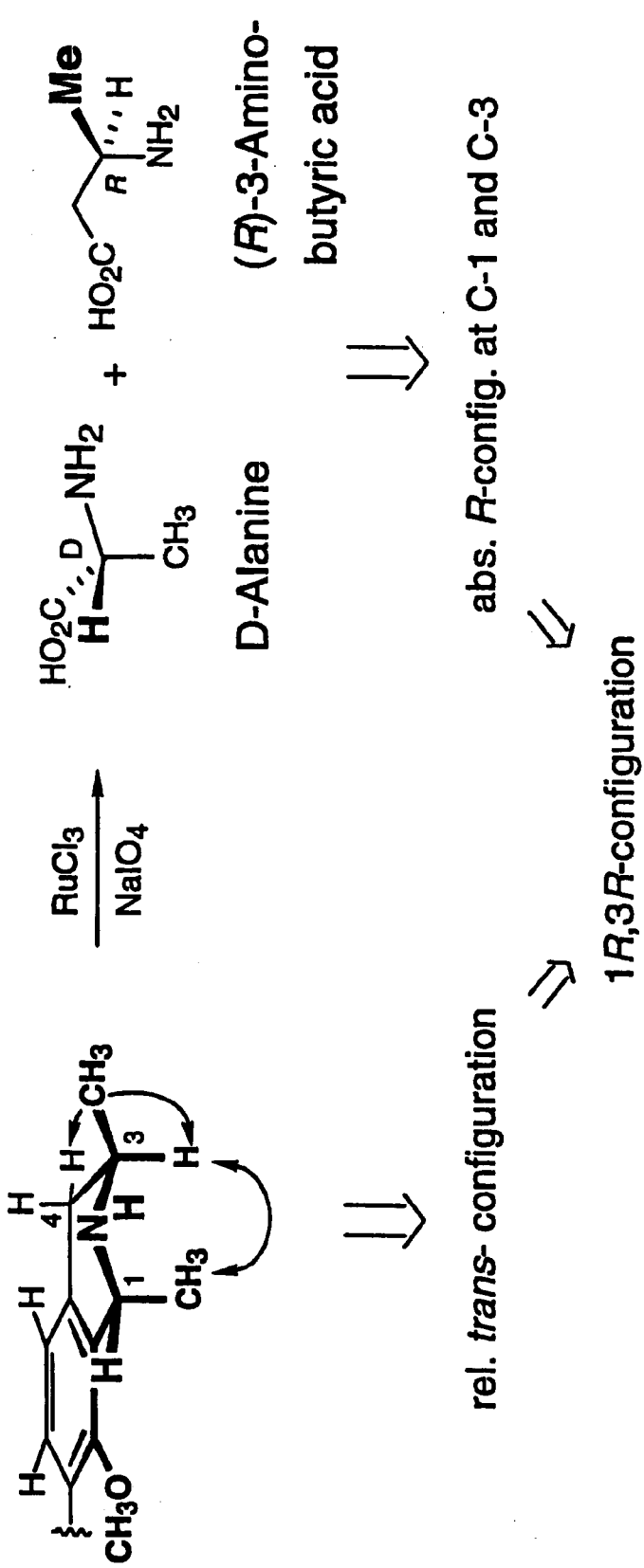
FIG. 4 illustrates the degradation procedure and the key NOE interactions used to demonstrate the relative and absolute configurations at the stereogenic centers of the tetrahydroisoquinoline portion of a compound of the present invention.

This example illustrates the procedure for isolation, purification, and structure elucidation of a compound of the present invention. Dried leaves of *T. peltatum* (19.4 g) were powdered and macerated two times for 2 days with 200 mL MeOH/1 N HCl (1:1 v/v) at ambient temperature with ultrasonic assistance. After evaporation of the MeOH in vacuo, the aqueous residue was re-extracted two times with 1 L portions of chloroform to yield 317 mg of a yellow crude extract, which was chromatographed over silica gel (40 g, deactivated with 7.5% $NH_3$) using $CH_2Cl_2$/MeOH (95:5) as the eluent to yield a fraction of 18 mg containing a compound of the present invention. Further purification was done first by semipreparative TLC ($CH_2Cl_2$/MeOH (95:5), $R_f$=0.63) and then by semipreparative HPLC using a Nova-Pak $C_{18}$ (200×25 mm, 6 μm) column with MeOH/$H_2O$ (6:2) as the eluent to give 4 mg (0.021%) as a yellow solid, mp 228–232° C.; $α_D^{25}$+21° (c=0.051, $CHCl_3$), IR (KBr): v=3400, 3920, 1650, 1400, 1250, 1090 $cm^{-1}$. $^1$H-NMR (200.1 MHZ $CDCl_3$): δ=1.22 (3H, d, J=6.1 Hz, 3-$CH_3$), 1.53 (3H, d, J=6.4 Hz, 1-$CH_3$), 2.40 (3H, s, 2'-$CH_3$), 2.69 (1H, dd, J=15.56, 2.74 Hz, 4-H), 2.91 (1H, m, 3-H), 3.36, (3H, s, 8-$OCH_3$), 3.95 (3H, s, 5'-$OCH_3$), 4.36 (1H, q, J=5.8 Hz, 1-H), 6.57 (1H, d, J=1.2 Hz, 3'-H), 6.83 (1H, d, J=8.1 Hz, 5-H), 7.21 (1H, d, J=8.1 Hz, 6-H), 7.22 (1H, d, J=1.2 Hz, 1'-H), 7.25 (1H, d, J=8.45 Hz, 7'-H), 7.36 (1H, d, J=8.45 Hz, 6'-H), $^{13}$C-NMR (63.25 MHZ, $CDCl_3$): δ=20.30 (3-$CH_3$), 21.90 (1-$CH_3$ and 2'-$CH_3$), 37.00 (4-C), 49.53 (3-C), 50.93 (1-C), 56.09 (4'-$OCH_3$), 60.11 (8-$OCH_3$), 106.55 (3'-C), 113.31 (4a'-C), 118.00 (6-C), 120.84 (1'-C), 123.72 (5-C), 127.20 (8a-C), 129.72 (7-C), 130.31 (7'-C), 130.93 (6'-C), 136.29 (8a'-C), 135.85 (2'-C), 136.45 (4a-C), 150.89 (5'-C), 155.95 (8-C), 156.18 (4'-C), MS (70 eV): m/z (%)=378 (3.81[M+], 377 (13.43) [M+—H], 362 (100) [M+—$CH_3$] HRMS: m/z 362.175 (M+—$CH_3$, $C_{23}H_{24}O_3N$, 362.176). These and other spectroanalytical data and analyses were used to elucidate the identity of this isolated and purified compound. FIG. 4 illustrates the degradation procedures used to demonstrate the stereochemistry. Example 3, which follows, illustrates in greater detail the use of these types of data, analyses, and procedures for demonstration of structures and stereochemistry of compounds of the present invention.

Example 3

Figure 5:
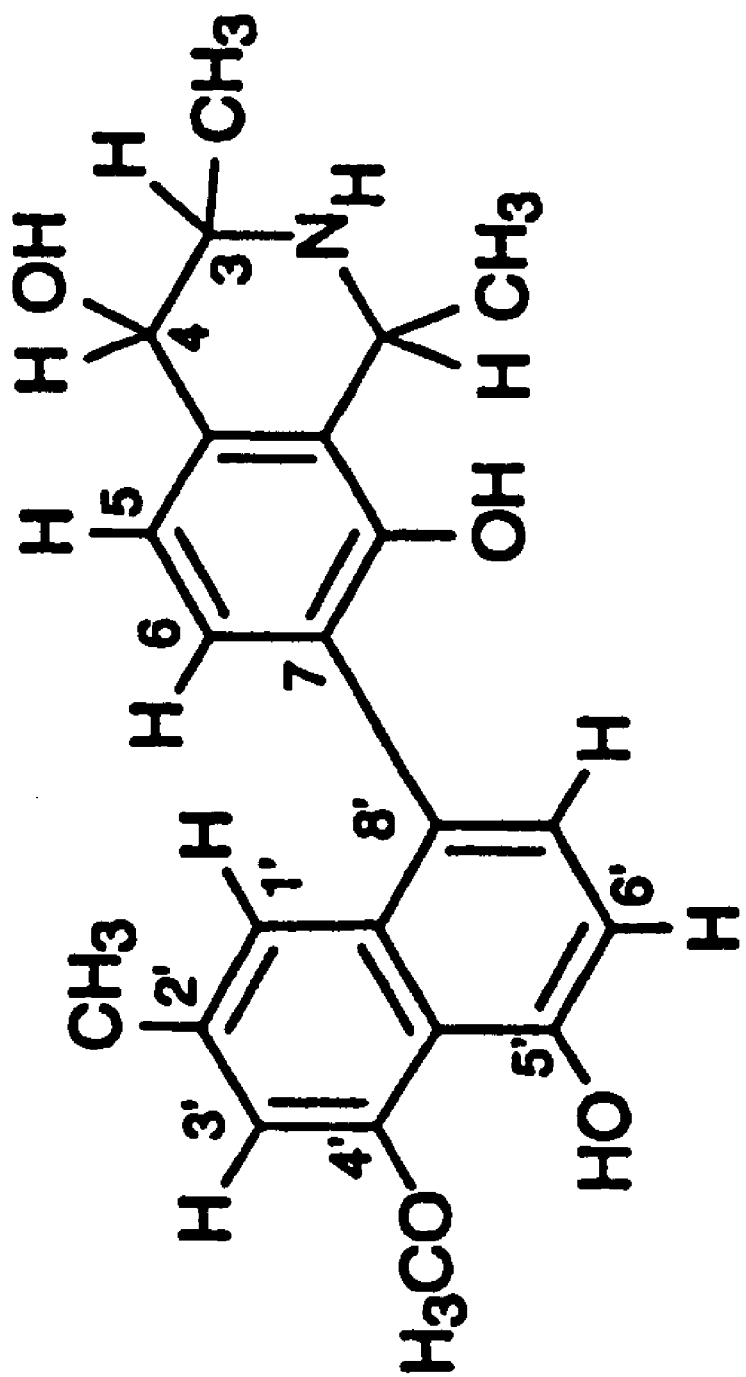
FIG. 5 illustrates the structure of dioncophyllinol D.

This example illustrates the structure elucidation of a compound of the present invention. The $^1$H NMR spectrum of the compound isolated Example 1 showed the typical signals for a naphthylisoquinoline alkaloid. Different, for example, from dioncophylline A (Bringmann et al. *Tetrahedron Lett.*, 31, 643–646 (1990)), the coupling pattern of the aromatic protons, in particular the presence of four aromatic doublets and two singlets, suggested the biaryl axis to be positioned in the 6' or in the 8' position of the naphthalene part. The main difference compared to the $^1$H NMR spectrum of dioncophylline A, however, was the lack of the typical diastereotopic protons at C-4 with expected chemical shifts of 2.7 (dd) and 3.4 (dd) ppm. Instead, a distinctly low-field shifted doublet (J=2.2 Hz) was observed at 4.5 ppm (FIG. 5A), hinting at the presence of a CH-X array at C-4, which was furthermore confirmed by the multiplicity of H-3 (δ3.7 ppm, dq, J=2.2 Hz, 6.9 Hz). From the chemical shift of H-4 (δ4.5 ppm), an OH group could be assumed to be located at C-4. The presence of a novel 4-hydroxylated naphthyltetrahydroisoquinoline alkaloid was corroborated by HRMS, which delivered the molecular formula $C_{23}H_{25}NO_4$ (M+, m/z=379.177). NOE interactions of H-5 with both H-4 and H-6 suggested the biaryl axis was located at C-7 of the isoquinoline part. The methoxy group in the naphthalene part was located at C-4'.

Figure 6:
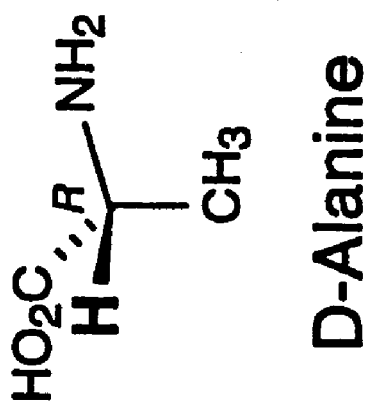
FIG. 6 illustrates the degradation procedure and key NOE interactions used to demonstrate the relative and absolute configurations at the stereogenic centers of the tetrahydroisoquinoline portion of a compound of the present invention.
Figure 6:
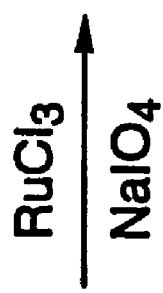
Figure 6:
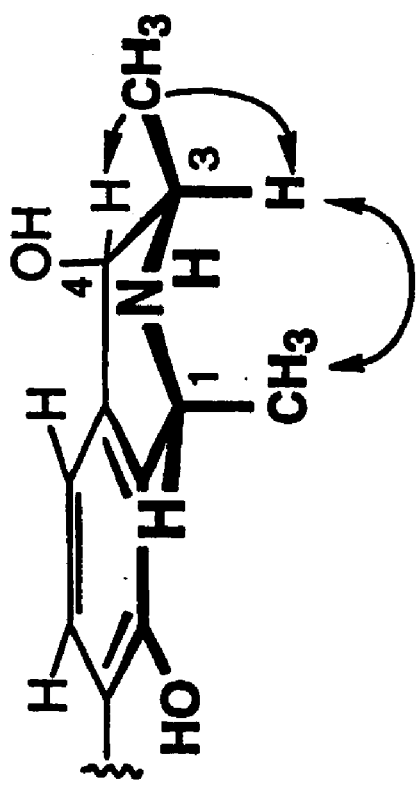

This novel alkaloid with the unprecedented extra OH—group at C-4 is the first naphthylisoquinoline alkaloid with three stereocenters at C-1, C-3, and C-4. From an NOE interaction between H-3 and $CH_3$-1 (FIG. 6), which were thus both axial and cis to each other, a relative trans-configuration of the two methyl groups at C-1 and C-3 was deduced. The small coupling constant (J =2.2 Hz) between the axial proton at C-3 and H-4 indicated the latter to be equatorial, revealing a relative cis-configuration of OH-4 and $CH_3$-3. This was confirmed by another clear NOE interaction between H-3 and H-4, which excluded a trans-diaxial position of these two protons and thus an equatorial position of the oxygen substituent at C-4. For the given cis-configuration at C-3 and C-4, both trans relative to $CH_3$-1, a semiempirical conformational analysis [AM1 (Dewar et al.,*J. Am. Chem. Soc.*, 107, 3902–3909 (1995)) as implemented in VAMP 5.0 (Rauhut et al., VAMP 5.0, Oxford Molecular Limited, Oxford Science Park, Standford on Thames, Oxford)] indicated the preferred presence of a half-chair conformation as seen in FIG. 6, in full agreement with the NOE data and coupling constants observed.

For the determination of the absolute configuration, the oxidative degradation procedure as disclosed in Bringmann et al., *Phytochemistry*, 43, 1393–1409 (1996), was used. Unlike all the other naphthyltetrahydroisoquinoline alkaloids degraded so far, no 3-amino butyric acid was to be expected because of the additional hydroxy function at C-4. In the present case, D-alanine was liberated. Unambiguous results were obtained from the D-alanine analyzed, whose absolute configuration clearly showed C-1 to be R-configured. From this and the relative configuration as elucidated above, the stereocenters C-3 and C-4 were also deduced to have the R-configuration as illustrated in FIG. 6.

Example 4

Figure 3:
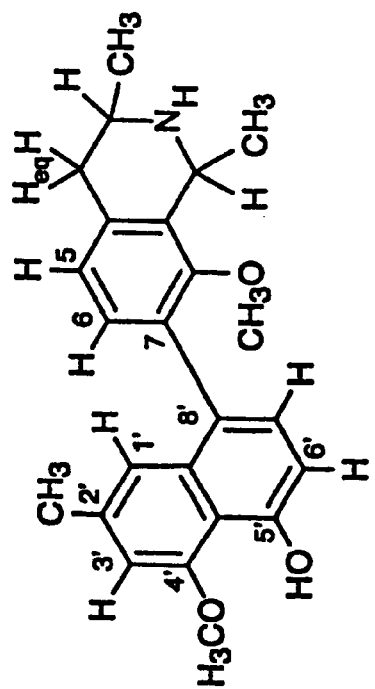
FIG. 3 illustrates the structure of 8-O-methyldioncophylline D.
Figure 7:
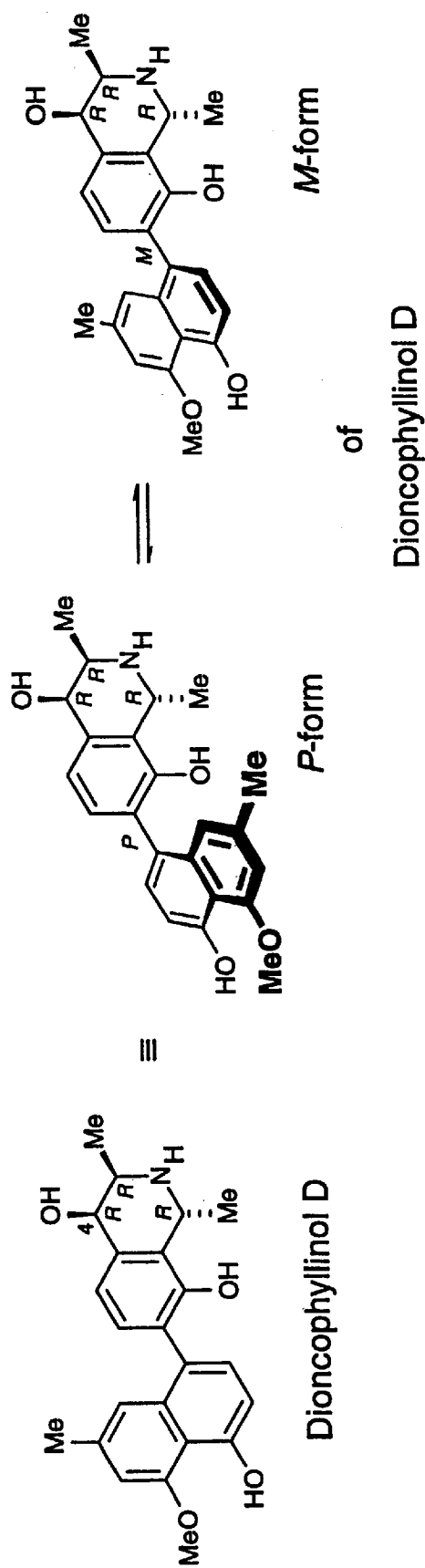
FIG. 7 illustrates the P- and M-atropisomeric forms of a dioncophyllinol, rapidly interconverting at room temperature.

This example illustrates the partial and total syntheses of the following exemplary monomeric compounds of the present invention: 8-O-methyl-dioncophylline D (FIG. 3), dioncophyllinol D (FIGS. 5 and 7), and 4-oxodioncophylline D.

In this example, approaches defined in previous disclosures are utilized in conjunction with known synthetic reactions and procedures, which can be found in Bringmann et al., U.S. Pat. No. 5,552,550; and Bringmann and Pokorny, The Alkaloids, Vol. 45 (G. Cordell, ed.), Academic Press, New York, pp. 127–271.

Figure 8:
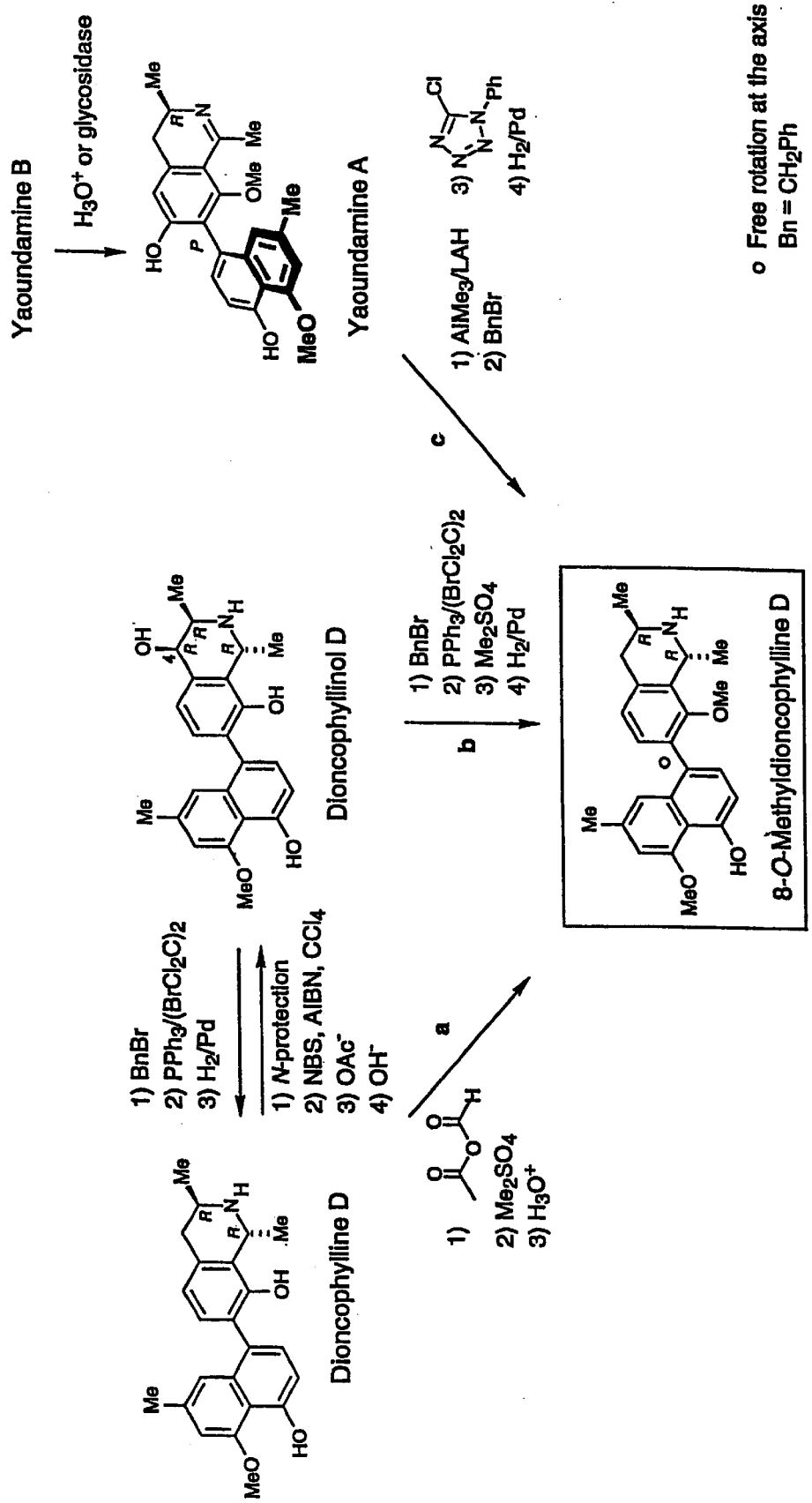
FIG. 8 illustrates various methods of preparation of 8-O-methyl-dioncophylline D.

FIG. 8 schematically shows preparation of 8-O-methyl-dioncophylline D by partial synthesis from other related alkaloids by several alternative methods including: (a) from dioncophylline D; by N-formylation, selective 8-O-methylation and acid-catalyzed cleavage of the N-protective group (analogous to: Bringmann et al., *Phytochemistry*, 30, 1691–1696 (1991)), (b) from dioncophyllinol D; by deoxygenation at C-4 to give dioncophylline D, and subsequent 8-O-methylation as above, or by N-beneylation, 8-O-methylation, and subsequent deoxygenation at C-4 (analogous to: Bringmann et al., *Phytochemistry*, 30, 1691–1696 (1991)), and (c) from yaoundamine A (which may be isolated and purified from *A. korupensis*, or by deglycosylation from yaoundamine B which is isolable from the same plant); by trans-selective reduction (analogous to: Bringmann et al., *Angew. Chem. Int. Ed. Engl.*, 25, 913–915 (1986)), N-benzylation, and 6-deoxygenation via the corresponding phenytetrazol- (or triflate-) derivative and hydrogenolytic debenzylation (analogous to: Bringmann et al., *Phytochemistry*, 31, 4019–4024 (1992); Bringmann et al., *Liebigs Ann. Chem.*, 877–888 (1993)).

Figure 9:
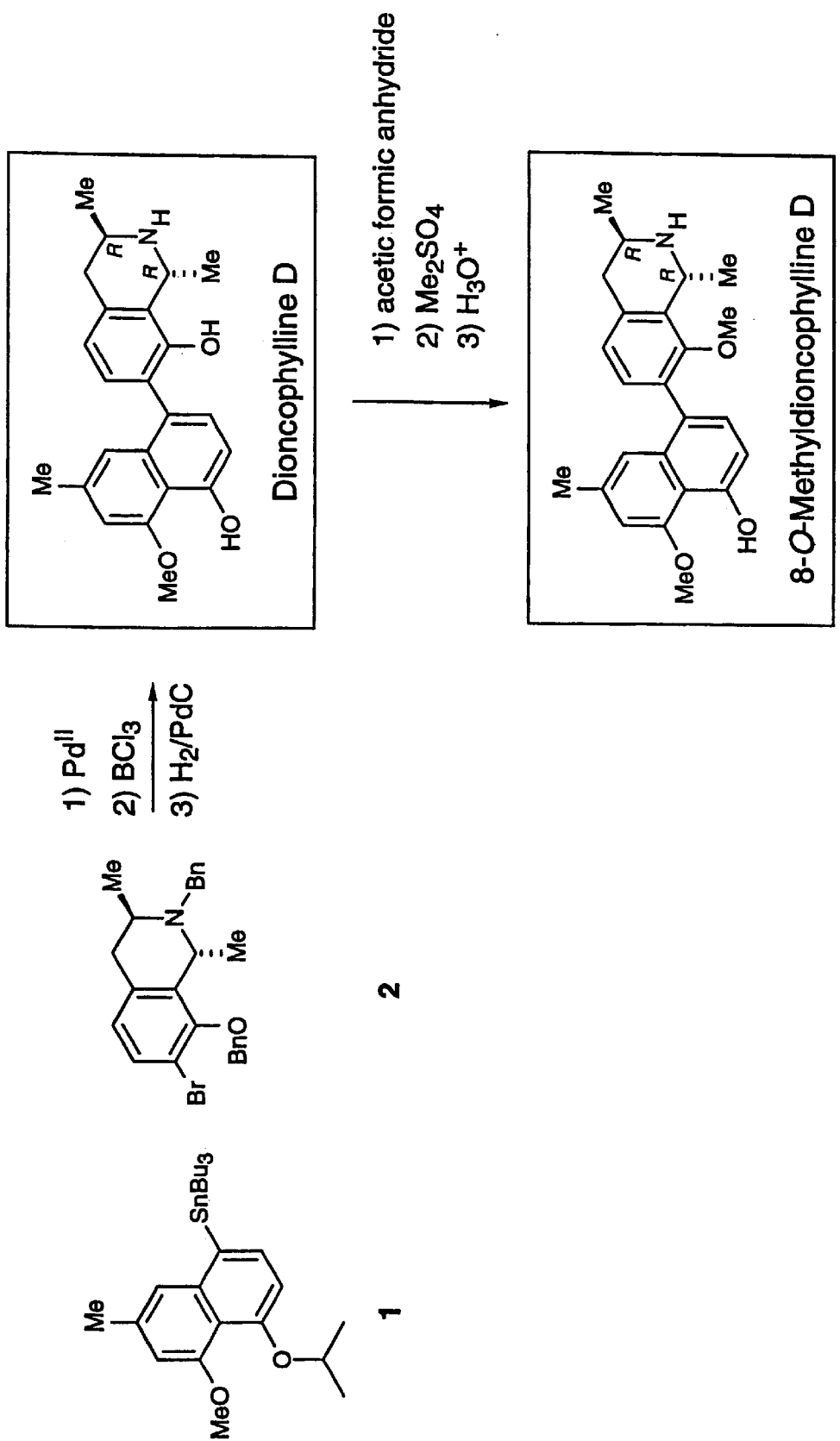
FIG. 9 illustrates a method of preparing dioncophylline D and 8-O-methyldioncophylline D by total synthesis via intermolecular biaryl coupling.
Figure 10:
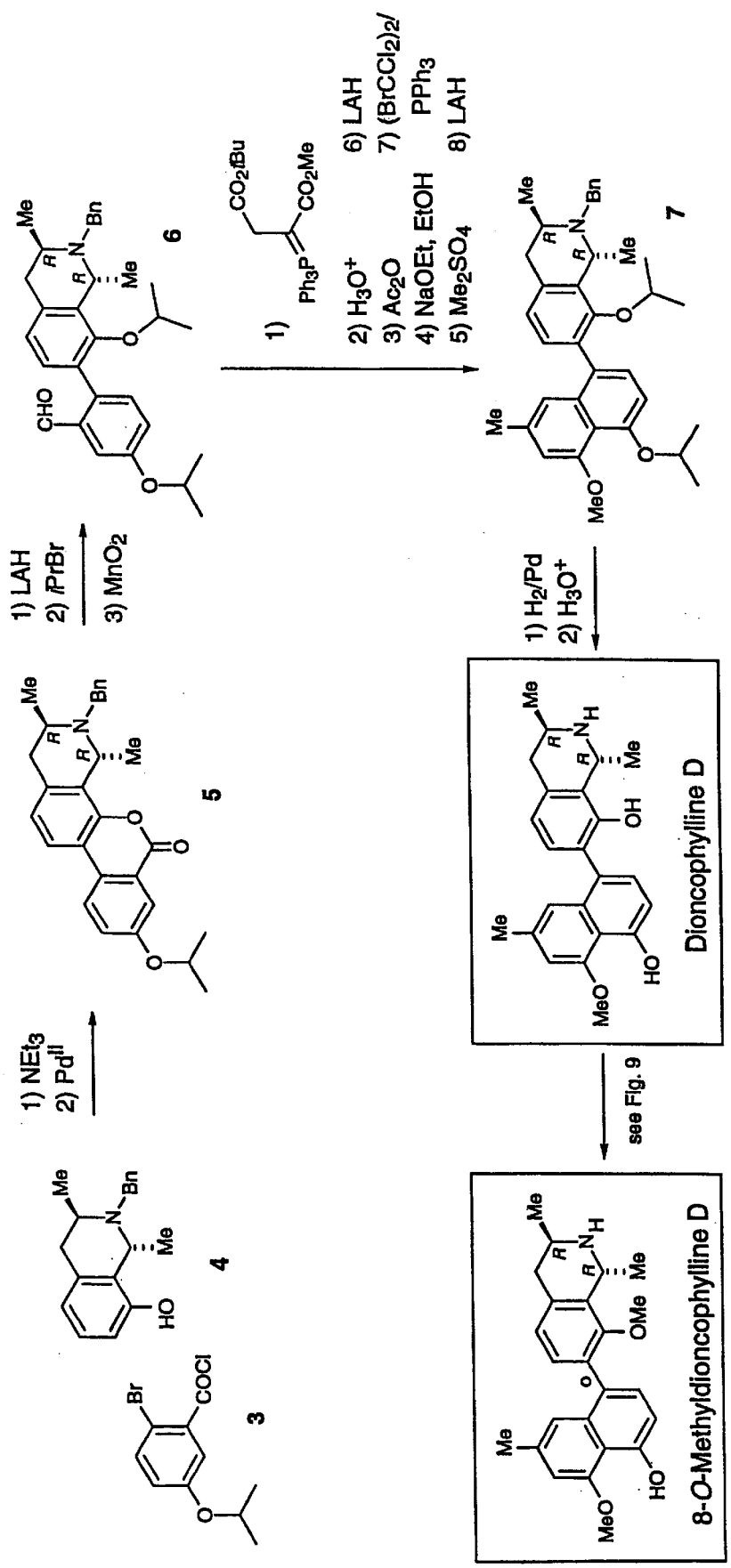
FIG. 10 illustrates preparation of dioncophylline D and 8-O-methyl-dioncophylline D by total synthesis via intramolecular biaryl coupling.
Figure 11:
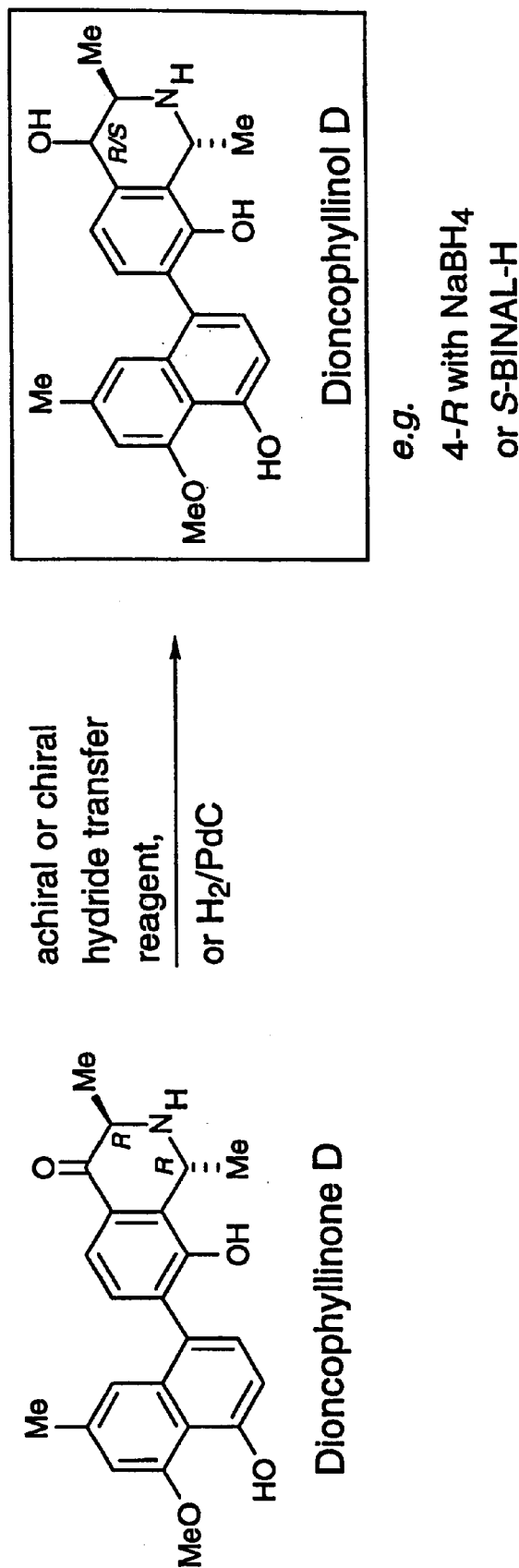
FIG. 11 illustrates a method of preparing dioncophyllinol D from dioncophyllinone D.

FIGS. 9 and 10 schematically show two alternative methods of preparing dioncophylline D and 8-O-methyldioncophylline D by total synthesis, including: (a) (FIG. 9) construction of the biaryl axis through intermolecular coupling of an appropriately protected and activated naphthalene building block 1 and a protected and activated tetrahydroisoquinoline part 2 using transition metal catalysis (analogous to: Bringmann et al., *Heterocycles*, 39, 503–512 (1994); Bringmann et al., U.S. Pat. No. 5,552,550) and subsequent cleavage of the protective groups, to give dioncophylline D, which may be converted to O-methyldioncophylline D as described above, and (b) (FIG. 10) by construction of the biaryl axis using the "lactone method" (analogous to: Bringmann et al., *Tetrahedron Lett.*, 31, 643–646 (1990)); Bringmann et al., Methods of Organic Chemistry (G. Helmchen, et al., eds.), Vol. E21a, Thierne, Stuttgart, 1995, pp. 567–587) comprising prefixation of an appropriately protected phenolic isoquinoline building block 4 with the acid chloride of the monocyclic benzoic acid derivative 3, transition metal catalyzed intramolecular coupling, ring cleavage with hydrogen transfer reagents, 8-O-protection and oxidation to give the intermediate 6 whose aldehyde function is then used to build up the second naphthalene ring to give 7 (analogous to: Bringmann et al., *Heterocycles*, 39, 503–512 (1994); Bringmann et al., U.S. Pat. No. 5,552,550), cleavage of the protective groups to give dioncophyllinone D, which can be transformed into 8-O-methyldioncophylline D as described above. FIG. 11 shows a method for preparing dioncophyllinol D by partial synthesis from dioncophylline D, by reduction with achiral (e.g., NaBH$_4$) or chiral (e.g., S-BINAL-H) hydride transfer reagents (analogous to: R. Noyori et al., *J. Am. Chem. Soc.*, 106, 6709–6716 (1984)), to give dioncophyllinol D or its epimer respectively.

Figure 12:
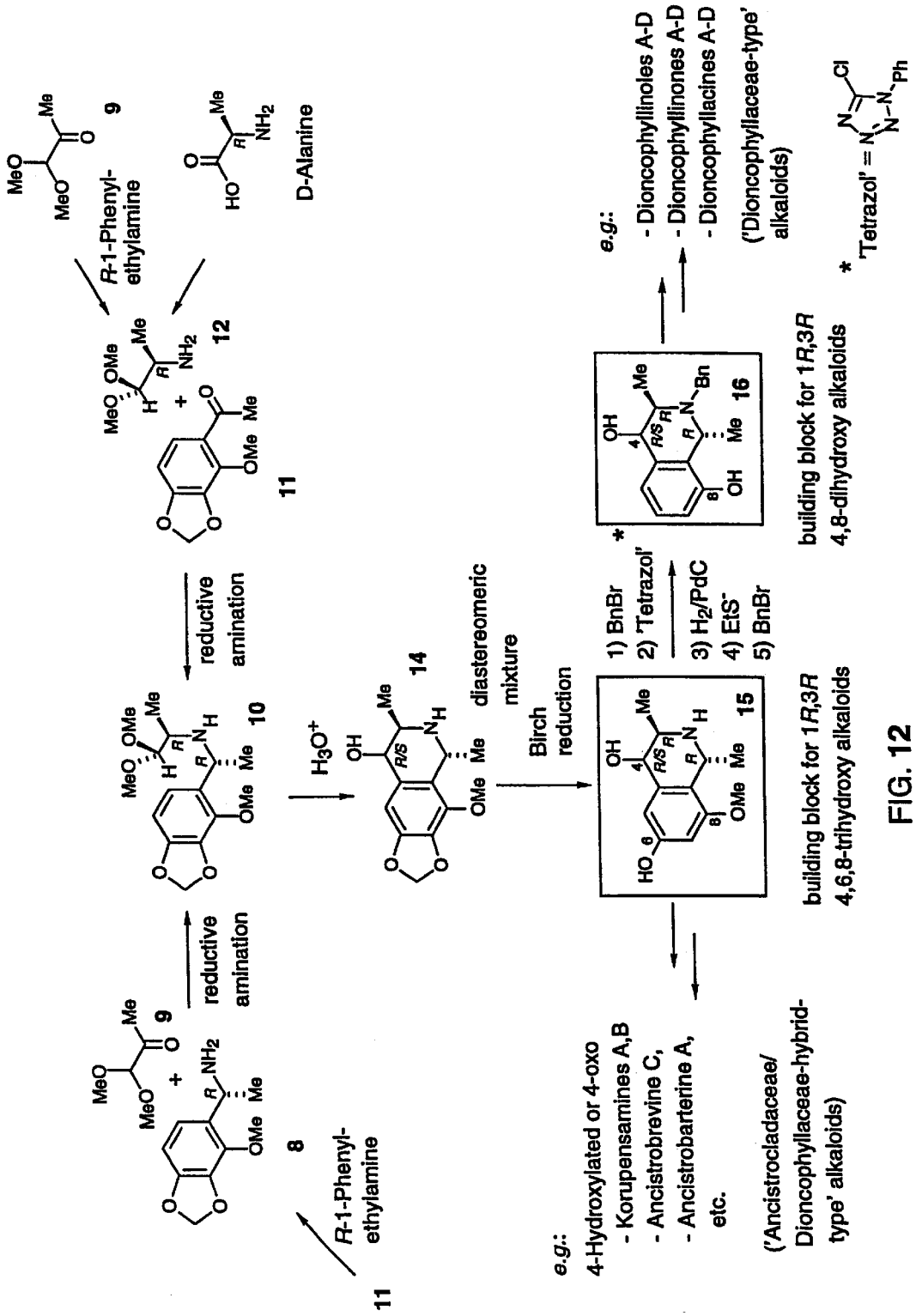
FIG. 12 illustrates a method of preparing of 4-hydroxyisoquinoline building blocks with 1R,3R-configuration.
Figure 13:
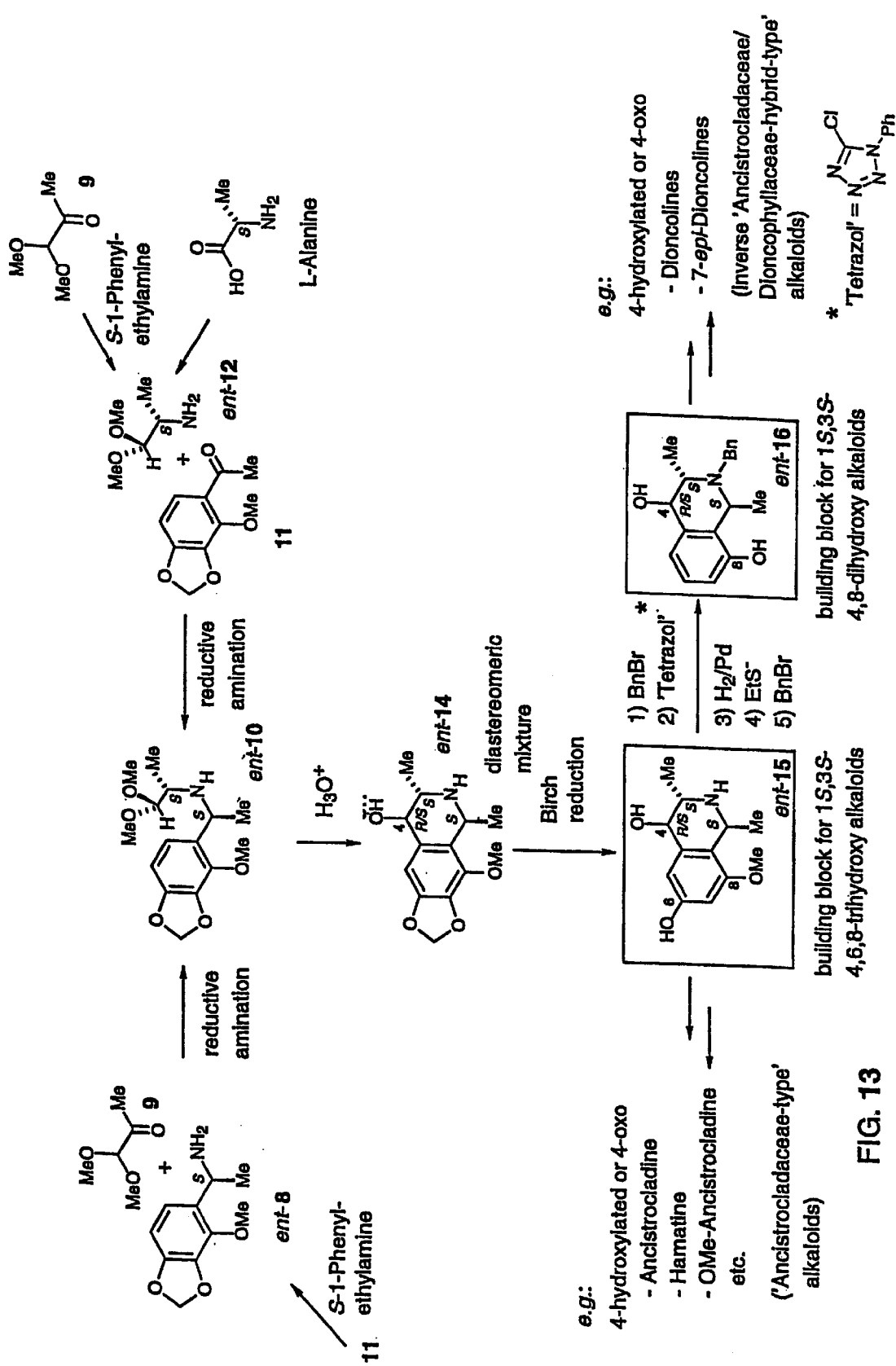
FIG. 13 illustrates preparation of 4-hydroisoquinoline building blocks with 1S,3S-configuration.
Figure 14:
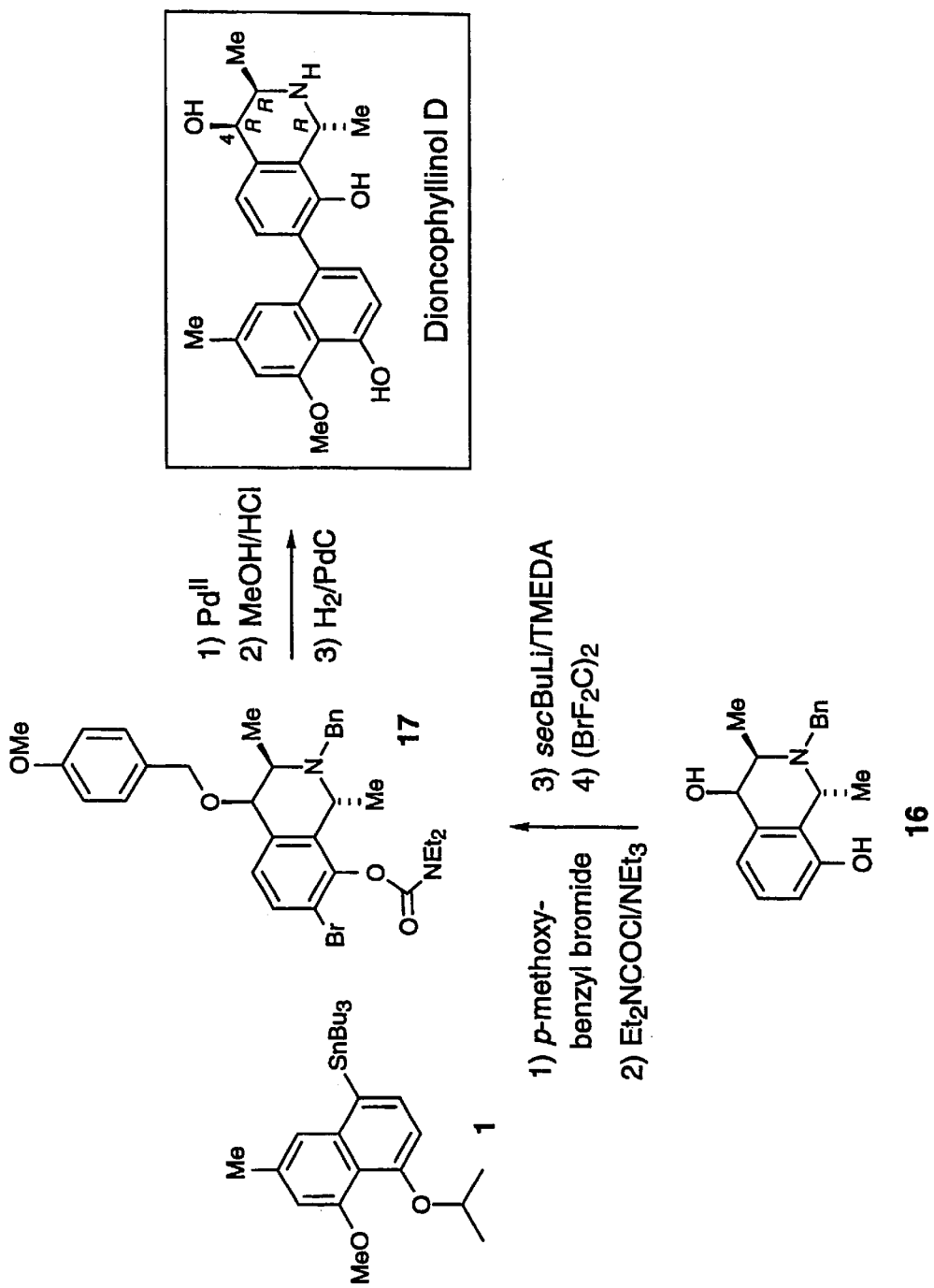
FIG. 14 illustrates a method of forming the naphthalene/isoquinoline biaryl axis by an intermolecular transition metal catalyzed coupling.

FIGS. 12–14 illustrate a method for preparing dioncophyllinol D and related 4-hydroxylated naphthylisoquinoline alkaloids by total synthesis, comprising: (a) (FIG. 12) synthesis of the required 4-hydroxyisoquinoline building block, e.g., with 3R-configuration, by stereoselective reductive amination of the keto acetal 9 using the substituted 1-phenylethylamine 8 (analogous to: Bringmann et al., German Patent (D.O.S.) 38 19 438; Bringmann et al., *Liebigs Ann. Chem.*, 795–805 (1990)) to give the amino acetal intermediate 10, which can also be prepared by reductive amination of the acetophenone 11 using the amino acetal 12, which, itself, is available by reductive amination of the aforementioned keto acetal 9 with unsubstituted 1-phenylethylamine (Bringmann and Geisler, *Synthesis*, 608–610 (1989); Bringmann et al., German Patent (D.O.S.) 38 43 390; European Patent 0 374 647) or from the amino acid D-alanine (analogous to: Jurcak and Golebiowski, *Chem. Rev.*, 89, 149, (1989)); ring closure of 10 by Pommeranz-Fritsch cyclization to give 14, and Birch reduction for the elimination of the 7-oxo-function to give 15 (analogous to: Bringmann, The Alkaloids, Vol. 29 (A. Brossi, ed.) Academic Press, New York, 1986, pp. 141–184) which is the required building block for the synthesis of a series of 4,6,8-trihydroxy alkaloids with R-configuration at C-3 (the "Ancistrocladaceae/Dioncophyllaceae hybrid-type" alkaloids), in particular 4-hydroxylated or 4-oxo derivatives of korupensamines, ancistrobrevine C, ancistrobarterine A, and others; final reductive elimination of O-6 using the tetrazol method (analogous to: Bringmann et al., *Liebigs Ann. Chem.*, 877–888 (1993)), 8-O-demethylation as before, and N-protection to give 16, the crucial building block for the C-4 hydroxyl, methoxy or oxo derivatives of dioncophyllines A–C, and the dioncophyllacines A–D; (b) (FIG. 13) the corresponding enantiomeric isoquinoline building blocks, with 1S,3S-configuration, which can be prepared by the aforementioned methods, but starting from the enantiomeric materials, giving rise to ent-10 and thus ent-15, the synthetic precursor to 1S-3S-configured 4,6,8-trihydroxy alkaloids like 4-hydroxylated or 4-oxo analogs of ancistrocladine, hamatine, O-methylancistrocladine, and others ("Ancistrocladaceae-type" alkaloids) and ent-16, the building block for 1S,3S-configured 4,8-dihydroxy alkaloids, such as 4-hydroxylated or 4-oxo analogs of dioncoline or 7-epi-dioncoline (inverse "Ancistrocladaceae/Dioncophyllaceae hybrid-type" alkaloids—e.g., Bringmann and Pokorny, The Alkaloids, Vol. 46 (G. Cordell, ed.), Academic Press, New York, 1995, pp. 127–271); (c) (FIG. 14) the construction of the axis by intermolecular transition metal catalyzed coupling of the appropriately protected and activated naphthalene building block 1 (analogous to: Bringmann et al., *Heterocycles*, 39, 503–512 (1994); Bringmann et al., U.S. Pat. No. 5,552,550) with the protected and appropriately activated isoquinoline building block 17 prepared from the aforementioned dihydroxytetrahydroisoquinoline 16 by standard protection and activation steps and subsequent deprotection to give dioncophyllinol D (analogous to: Wang et al., *J. Org. Chem.*, 57, 424–436 (1992)).

Figure 15:
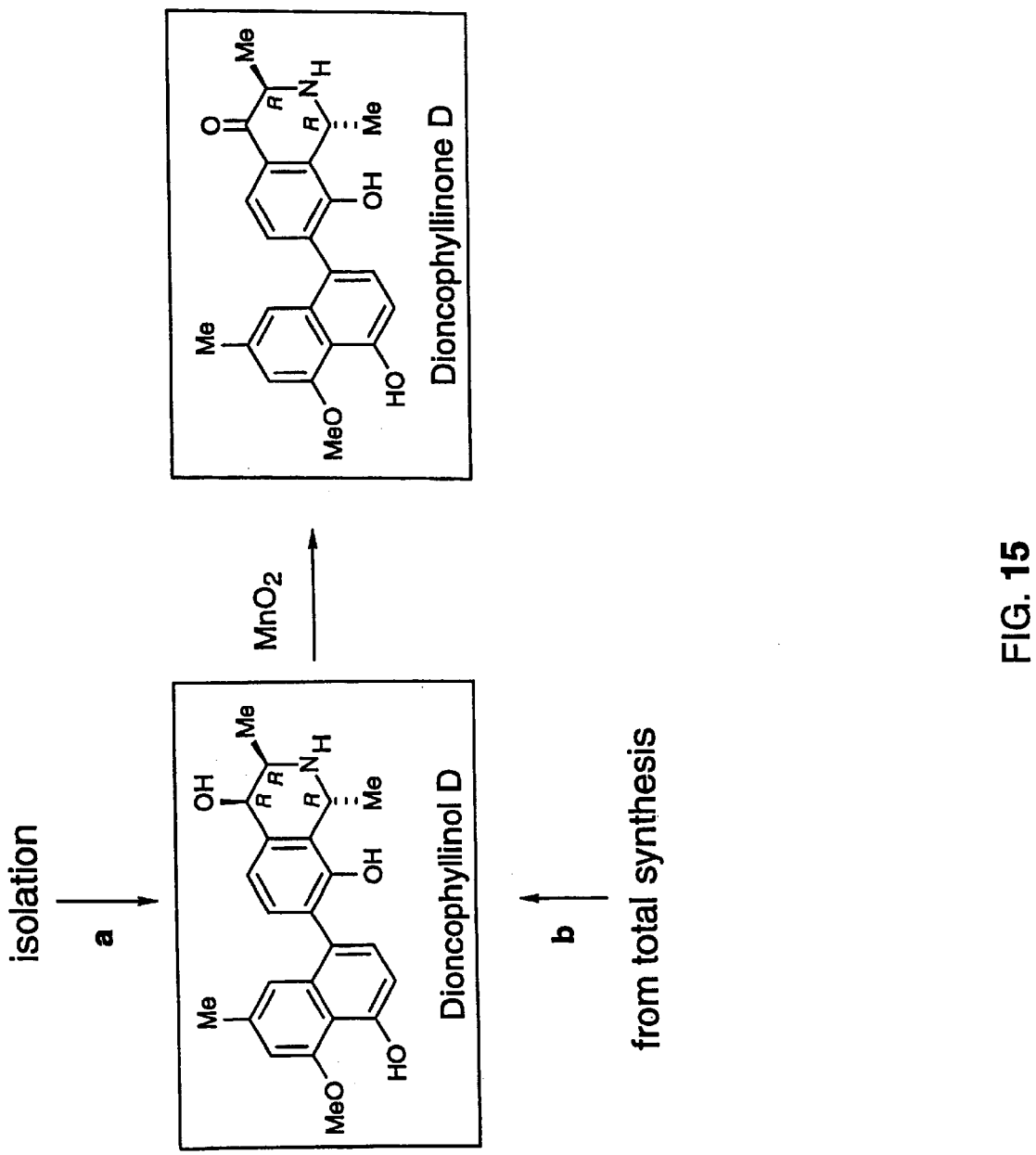
FIG. 15 illustrates a method of preparing a C-4 oxo arylisoquinoline from dioncophyllinol D by partial synthesis or total synthesis.
Figure 16:
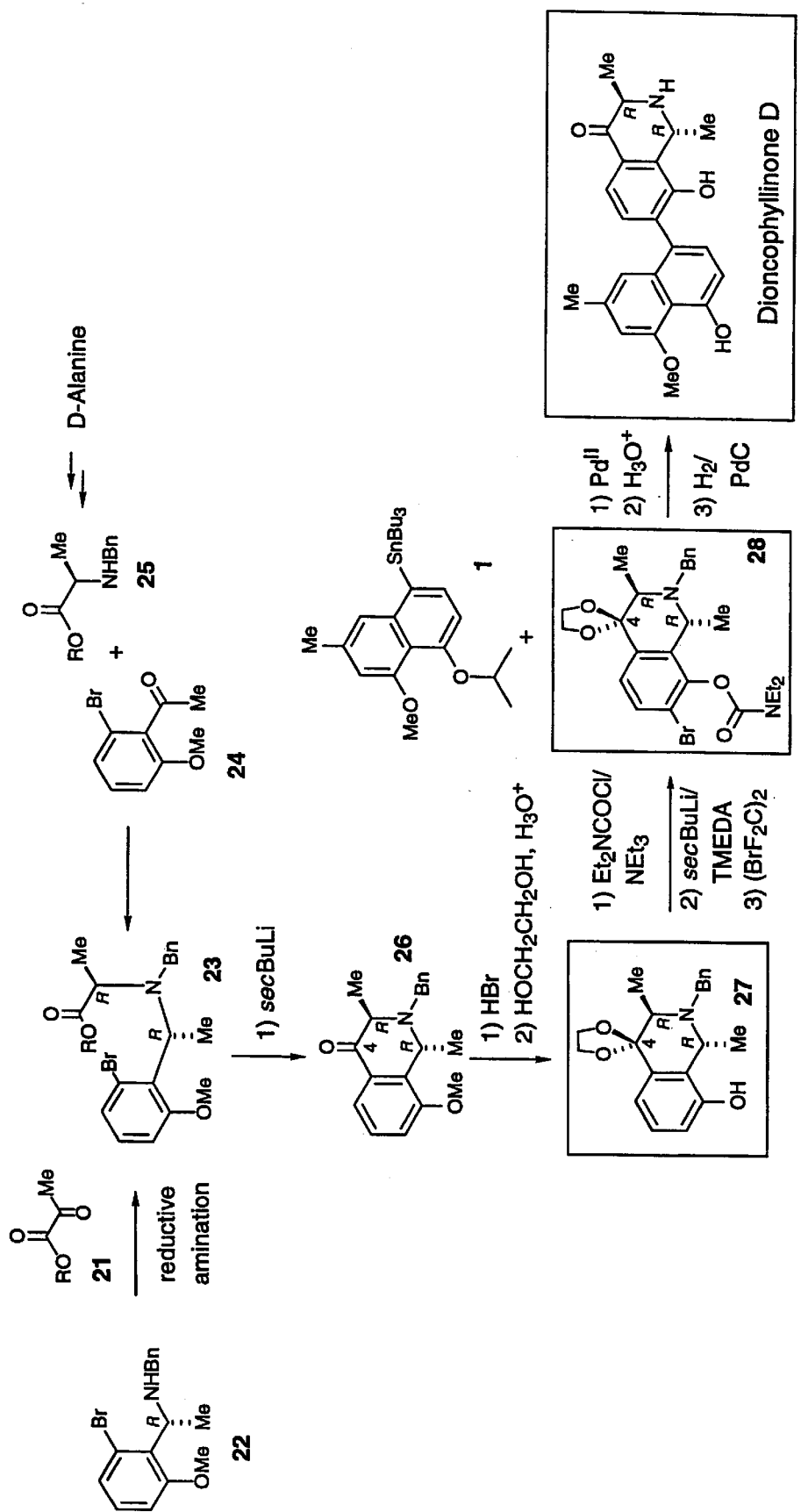
FIG. 16 illustrates a method of preparing a C-4 oxo arylisoquinoline by total synthesis.

FIGS. 15 and 16 illustrate methods of preparing an exemplary C-4 oxo compound of the present invention: dioncophyllinone D. These include by (a) (FIG. 15) partial synthesis from isolated dioncophyllinol D through e.g., oxidation with MnO$_2$ or (b) (FIG. 15) starting from dioncophyllinol D obtained by total synthesis. FIG. 16 illustrates preparation of dioncophyllinone D through independent total synthesis, by preparation of the appropriate 4-oxo-tetrahydroisoquinoline building block by reductive amination of the α-keto ester 21 with the appropriately substituted 1-phenylethylamine 22 to give the amino ester 23 (which can likewise be produced by reductive amination of the acetophenone 24 with the D-alanine derivative 25), subsequent cyclization of 23 to give the 4-oxo-tetrahydroisoquinoline 26, transformation into the building block 28, which is coupled to the aforementioned building block 1 (Bringmann et al., *Heterocycles*, 39, 503–512 (1994); Bringmann et al., U.S. Pat. No. 5,552,550), followed by hydrogenolytic and acid-catalyzed cleavage of the protective groups, to give dioncophyllinone D.

Example 5

Partial and Total Synthesis of Exemplary Dimeric Arylisoquinoline Alkaloid Compounds of the Present Invention: Homodimeric Naphthylisoquinoline Alkaloids, Heterodimeric Naphthylisoquinoline Alkaloids, and Heterodimeric Naphthylisoquinoline/Phenylisoquinoline alkaloids.

This example illustrates partial and total synthesis strategies for preparing exemplary homodimeric and heterodimeric arylisoquinoline alkaloids compounds of the present invention using approaches defined in previous disclosures and in conjunction with other now well-known reactions and procedures (Bringmann et al., U.S. Pat. No. 5,571,919; Bringmann et al., U.S. Pat. No. 5,578,729; Bringmann et al., U.S. patent application Ser. No. 08/721,084; and Bringmann and Pokorny, The Alkaloids, Vol. 46 (G. Cordell, ed.), Academic Press, New York, 1995, 127–271.

Figure 17:
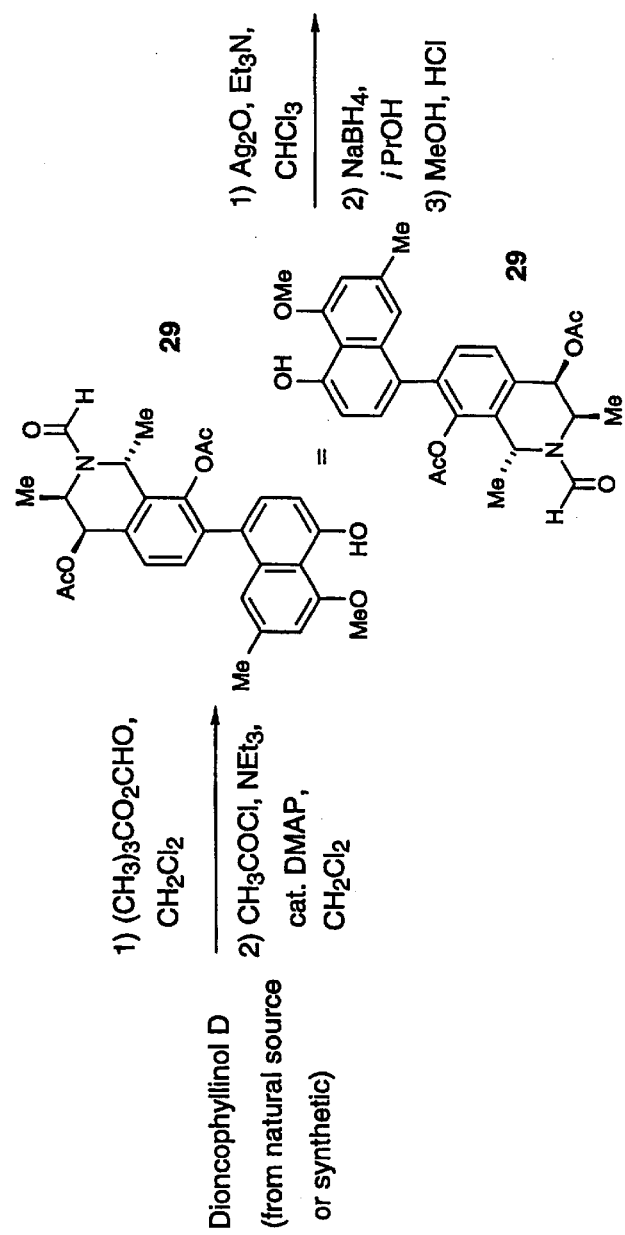
FIG. 17 illustrates a method of preparing a homodimeric arylisoquinoline alkaloid.
Figure 18:
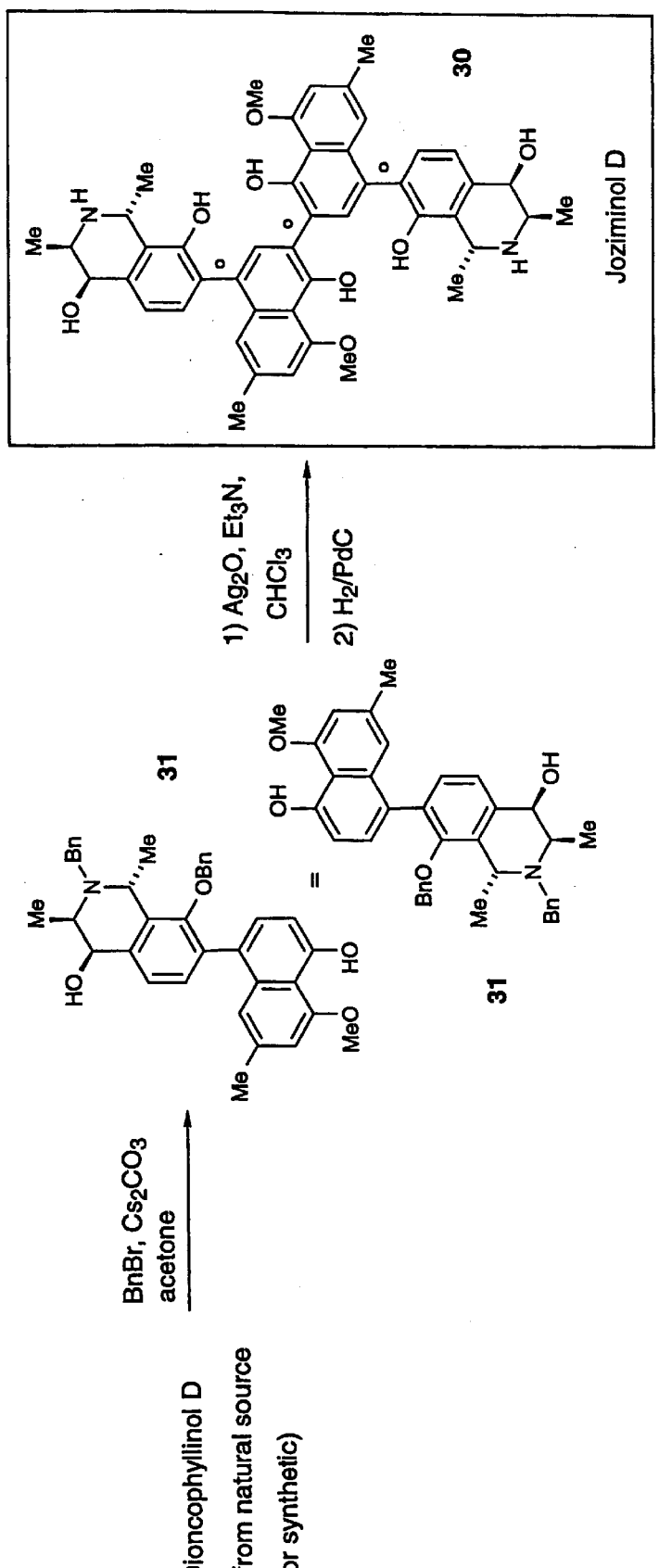
FIG. 18 illustrates a method of preparing a homodimeric arylisoquinoline alkaloid.

FIGS. 17 and 18 illustrate methods of preparing joziminol D (homodimeric dioncophyllinol D) 30 by partial (or total) synthesis, starting from natural (or synthetic) dioncophyllinol D. In the first scheme (FIG. 17) dioncophyllinol D is N-formylated and then specifically O-acetylated to give N-formylated and O-acylated monomeric "halves" 29, followed by oxidative dimerization using silver oxide/triethylamine, and reduction of the central double bond using NaBH$_4$/iPrOH and deprotection by refluxing in MeOH/HCl to give 30 (analogous to: Bringmann et al., Liebigs Ann., 2045–2085 (1996); Bringmann et al., Tetrahedron, 50, 9643–9648 (1994)). In the second scheme (FIG. 18) dioncophyllinol D is subjected to N- and O-specific benzylation to give N- and O-benzylated monomeric "halves" 31, followed by oxidative dimerization using silver oxide/triethylamine and one-step reduction/deprotection by hydrogenation with H$_2$/Pd/C, to give 30 (analogous to: Bringmann et al., Liebigs Ann., 2045–2085 (1996)).

Figure 19:
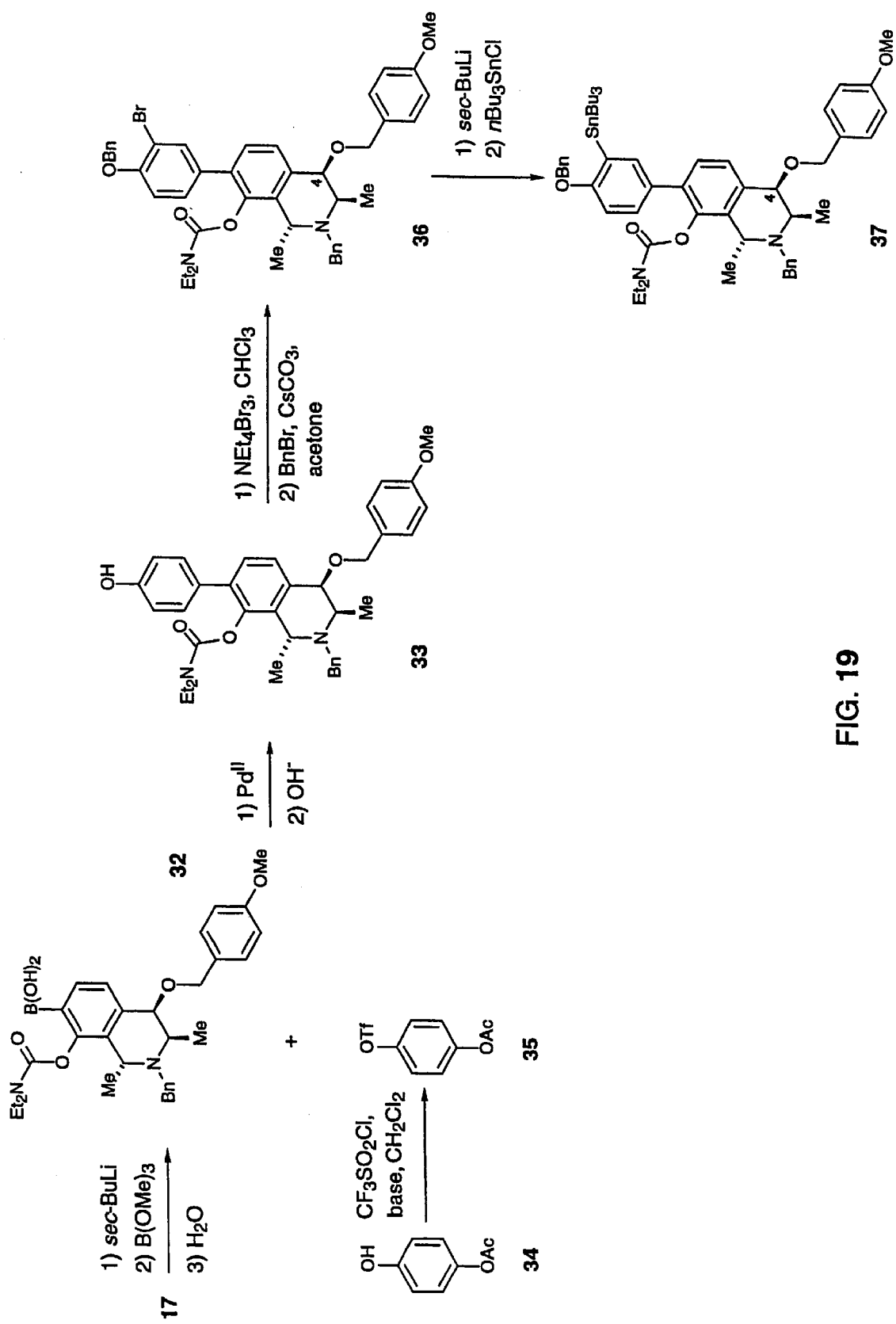
FIG. 19 illustrates a method of preparing a protected and activated monomeric phenylisoquinoline "half".
Figure 20:
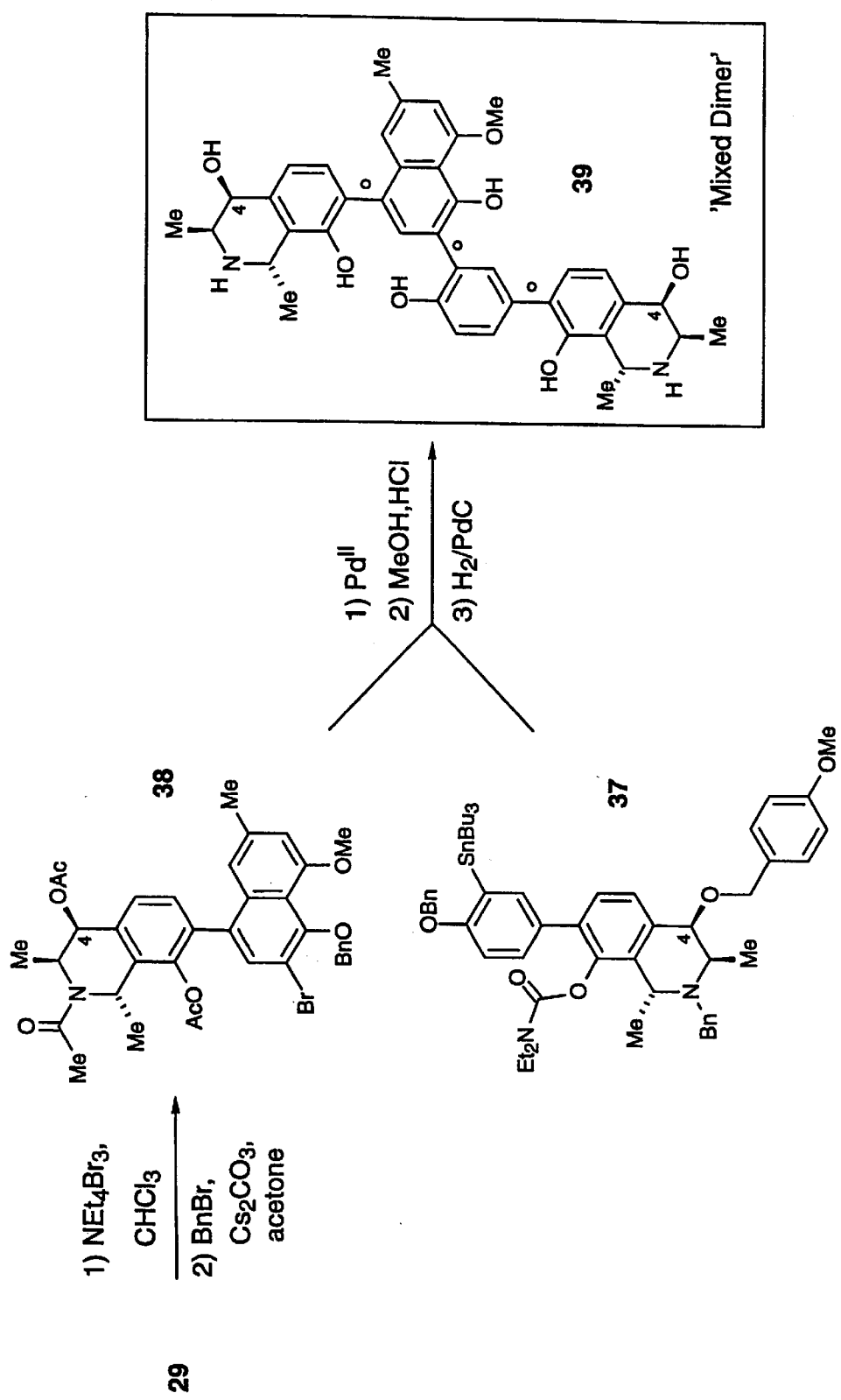
FIG. 20 illustrates a method of preparing a heterodimeric arylisoquinoline alkaloid comprising two different monomeric arylisoquinoline "halves".

FIGS. 19 and 20 illustrate a method for total synthesis of an exemplary heterodimeric arylisoquinoline alkaloid wherein one of the aryl groups is phenyl instead of naphthyl. In FIG. 19, synthesis of the boronic acid activated building block 32 starts from 17, by lithiation with sec-BuLi, treatment with trimethylborate and quenching with water (analogous to: Bringmann et al., Liebigs Ann., 2045–2085 (1996)), then synthesis of the protected monomeric building block 33 by transition metal catalyzed coupling of 32 with 35 (prepared from hydroquinone monoacetate 34 using trifluormethylsulfonyl chloride) to give 33 (Johnston, Chem. Ind., 24, 1000 (1982); and analogous to: Bringmann et al., Liebigs Ann., 2045–2085 (1996)). Synthesis of the activated building block 37 starts from 33, by selective bromination with tri-N-butyl ammonium tribromide and O-benzylation to give 36, and subsequent lithiation with sec-BuLi, and stannylation with tri-N-butylstannyl chloride (analogous to: Bringmann et al., Heterocycles, 39, 503–512 (1994)) to give activated monomeric molecular "half" 37.

FIG. 20 illustrates the preparation of the second appropriately protected and activated monomer "half" (38) and the coupling of the two different monomers to give an exemplary heterodimeric arylisoquinoline alkaloid (39) comprising an exemplary naphthylisoquinoline alkaloid monomer (dioncophyllinol D) coupled to a representative phenylisoquinoline alkaloid monomer (phenylisoquinolin-4-ol). In this scheme synthesis of the required building block 38 is accomplished by bromination of 29 with tri-N-butyl ammonium tribromide followed by O-protection with benzylbromide; then transition metal catalyzed cross-coupling of 37 with 38, followed by deprotection by refluxing with MeOH/HCl then hydrogenation with H$_2$/PdC to give 39 (analogous to: Bringmann et al., Heterocycles, 39, 503–512 (1994); Bringmann et al., U.S. Pat. No. 5,552,550; Bringmann et al., Liebigs Ann., 2045–2085 (1996)).

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A dimeric arylisoquinoline of coupled first and second arylisoquinoline monomers selected from the group consisting of derivatives of dioncophylline D, wherein: (a) the configuration at C-1 or C-3 is instead S; one or more phenolic hydroxyl group(s) is instead an ester, sulfonate ester, or ether group; a methyl ether group is instead a phenolic hydroxyl group; one or more phenolic hydroxyl group(s) is instead an aromatic hydrogen substituent; the secondary amine site is instead an amide, sulfonamide, tertiary amine, alkyl quaternary ammonium salt or corresponding Hoffmann elimination product thereof; at least one CH$_3$ is instead H; and/or the tetrahydroisoquinoline is instead a dihydroisoquinoline; and (b) a substituent at C-4 is azido, alkoxy, aryloxy, glycosyloxy or oxo; or any combination of the foregoing.

2. A dimeric arylisoquinoline of coupled first and second arylisoquinoline alkaloid monomers selected from the group consisting of derivatives of dioncophylline D, ancistrobrevine A, 6-O-demethyl-ancistrobrevine A, yaoundamine A, yaoundamine B, ancistroheynine A, dioncophylline B, dioncopeltine A, dioncophylline A, dioncophylline C, dioncolactone A, N-methyl-dioncophylline A, ancistrobrevine D, ancistrocladine, 5'-O-demethyl-8-O-methyl-7-epi-dioncophylline A, 5'-O-demethyl-7-epi-dioncophylline A, hamatine, ancistrobarterine A, 7-epi-dioncophylline A, N-formyl ancistrocladine, N-methyl-ancistrocladine, 6-deoxy-N-methyl-ancistrocladine, N-formyl-O,O-dimethyl-dioncophylline C, N-formyl-dioncophylline C, N-formyl-8-O-benzyl-dioncophylline C, N-formyl-8-O-methyl-dioncophylline C, N-formyl-8-O-pivaloyl-dioncophylline C, N-formyl-8-O-acetyl-dioncophylline C, N-formyl-8-O-benzoyl-dioncophylline C, and 8-O-methyl-dioncophylline C, wherein: (a) the configurations at C-1 and C-3 are the same or different, and each is R or S; the configuration about the naphthalene/isoquinoline axis is P or M, one or more phenolic hydroxyl group(s) may instead be an ester, sulfonate ester, or ether group; one or more methyl ether group(s) may instead be a phenolic hydroxyl group; one or more phenolic hydroxyl group(s) may instead be an aromatic hydrogen substituent; one or more secondary amine site(s) may instead be an amide, sulfonamide, tertiary amine, alkyl quaternary ammonium salt or corresponding Hoffmann elimination product thereof, one or more tertiary amine site(s) may instead be a secondary amine; one or more aromatic hydrogen substituent(s) may instead be C$_1$–C$_6$ alkyl, acyl, halo, nitro, amino, hydroxyl, acyloxy, alkoxy, aryloxy, glycosyloxy, thiol or cyano; at least one CH$_3$ may instead be H; the tetrahydroisoquinoline may instead be a dihydroisoquinoline; and (b) a substituent at C-4 is azido, alkoxy, aryloxy, glycosyloxy or oxo; or any combination of the foregoing.

3. A dimeric arylisoquinoline of coupled first and second arylisoquinoline alkaloid monomers selected from the group consisting of derivatives of dioncophylline D, ancistrobrevine A, 6-O-demethyl-ancistrobrevine A, yaoundamine A, yaoundamine B, ancistroheynine A, dioncophyllacine A, dioncophyllacine B, dioncophylline B, dioncopeltine A, dioncophylline A, dioncophylline C, dioncolactone A, N-methyl-dioncophylline A, ancistrobrevine D, ancistrocladine, 5'-O-demethyl-8-O-methyl-7-epidioncophylline A, 5'-O-demethyl-7-epi-dioncophylline A, dioncophylleine A, hamatine, ancistrobarterine A, 7-epi-dioncophylline A, N-formyl ancistrocladine, N-methyl-ancistrocladine, 6-deoxy-N-methyl-ancistrocladine, N-formyl-O,O-dimethyl-dioncophylline C, N-formyl-dioncophylline C, N-formyl-8-O-benzyl-dioncophylline C, N-formyl-8-O-methyl-dioncophylline C, N-formyl-8-O-pivaloyl-dioncophylline C, N-formyl-8-O-acetyl-dioncophylline C, N-formyl-8-O-benzoyl-dioncophylline C, and 8-O-methyl-dioncophylline C, wherein: (a) the configurations at C-1 and C-3 are the same or different, and each is R or S; the configuration about the naphthalene/isoquinoline axis is P or M, one or more phenolic hydroxyl group(s) may instead be an ester, sulfonate ester, or ether group; one or more methyl ether group(s) may instead be a phenolic hydroxyl group; one or more phenolic hydroxyl group(s) may instead be an aromatic hydrogen substituent; one or more secondary amine site(s) may instead be an amide, sulfonamide, tertiary amine, alkyl quaternary ammonium salt or corresponding Hoffmann elimination product thereof, one or more tertiary amine site(s) may instead be a secondary amine; one or more aromatic hydrogen substituent(s) may instead be $C_1$–$C_6$ alkyl, acyl, halo, nitro, amino, hydroxyl, acyloxy, alkoxy, aryloxy, glycosyloxy, thiol or cyano; (b) a dihydroisoquinoline or tetrahydroisoquinoline is instead a fully aromatic isoquinoline; and (c) a substituent at C-4 is alkoxy, aryloxy, glycosyloxy or oxo; or any combination of the foregoing.

4. A dimeric arylisoquinoline of coupled first and second arylisoquinoline alkaloid monomers selected from the group consisting of derivatives of korupensamine A, korupensamine B, korupensamine C, korupensamine D, and ancistrobrevine B, wherein: (a) the configurations at C-1 and C-3 are the same or different, and each is R or S; the configuration about the naphthalene/isoquinoline axis is P or M, one or more phenolic hydroxyl group(s) may instead be an ester, sulfonate ester, or ether group; one or more methyl ether group(s) may instead be a phenolic hydroxyl group; one or more phenolic hydroxyl group(s) may instead be an aromatic hydrogen substituent; one or more secondary amine site(s) may instead be an amide, sulfonamide, tertiary amine, alkyl quaternary ammonium salt or corresponding Hoffmann elimination product thereof, one or more tertiary amine site(s) may instead be a secondary amine; one or more aromatic hydrogen substituent(s) may instead be halo, nitro, amino, hydroxyl, acyloxy, alkoxy, aryloxy, glycosyloxy, thiol or cyano; and (b) a substituent at C-4 is alkoxy, aryloxy, glycosyloxy or oxo; or any combination of the foregoing.

5. A dimeric arylisoquinoline of coupled first and second arylisoquinoline alkaloid monomers selected from the group consisting of derivatives of korupensamine A, korupensamine B, korupensamine C, korupensamine D, and ancistrobrevine B, wherein: (a) the configurations at C-1 and C-3 are the same or different, and each is R or S; the configuration about the naphthalene/isoquinoline axis is P or M, one or more phenolic hydroxyl group may instead be an ester, sulfonate ester, or ether group; one or more methyl ether group may instead be a phenolic hydroxyl group; one or more phenolic hydroxyl group may instead be an aromatic hydrogen substituent; one or more secondary amine site may instead be an amide, sulfonamide, tertiary amine, alkyl quaternary ammonium salt or corresponding Hoffmann elimination product thereof, one or more tertiary amine site may instead be a secondary amine; one or more aromatic hydrogen substituent may instead be $C_1$–$C_6$ alkyl, acyl, halo, nitro, amino, hydroxyl, acyloxy, alkoxy, aryloxy, glycosyloxy, thiol or cyano; at least one $CH_3$ may instead be H; the tetrahydroisoquinoline may instead be a dihydroisoquinoline or a fully aromatic isoquinoline; (b) a substituent at C-4 is alkoxy, aryloxy, glycosyloxy or oxo; and (c) at least one aromatic hydrogen substituent is instead an acyl or $C_1$–$C_6$ alkyl, and/or a substituent at C-2' is not methyl when C-1 and C-3 are each substituted with a methyl; or any combination of the foregoing.

6. A compound of the formula:

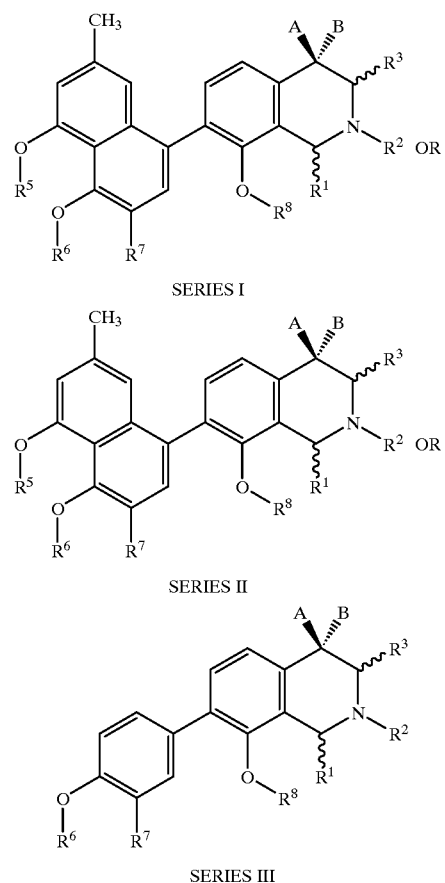

SERIES I

SERIES II

SERIES III wherein:

(a) A or B is azido, alkoxy, aryloxy, glycosyloxy; or A and B together are =O, =S, or —O(CH$_2$)$_n$O—, wherein n is an integer from 2–4;

(b) $R^2$ is H, $C_1$–$C_6$ alkyl, an amide, or sulfonamide;

(c) $R^1$ and $R^3$ are the same or different and each is ◀H, ⋯⋯H, ◀CH$_3$; or ⋯⋯CH$_3$;

(d) $R^5$, $R^6$, and $R^8$ are the same or different and is H or $C_1$–$C_6$ alkyl;

(e) one or more aromatic hydrogen substituent(s) may instead be $C_1$–$C_6$ alkyl, acyl, halo, nitro, amino, hydroxyl, acyloxy, alkoxy, aryloxy, glycosyloxy, thiol or cyano;

(f) the tetrahydroisoquinoline ring may instead be a dihydroisoquinoline ring or a fully aromatic isoquinoline ring; and (g) R⁷ is an arylisoquinoline of the formula:

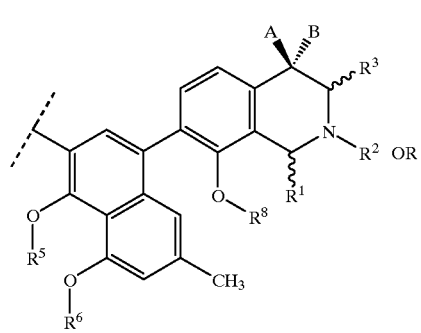

ARYLISOQUINOLINE I

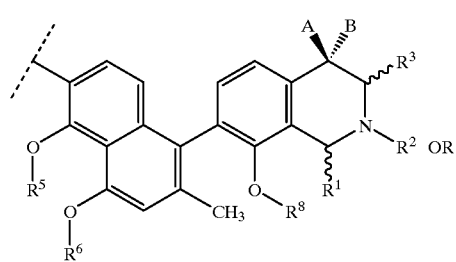

ARYLISOQUINOLINE II

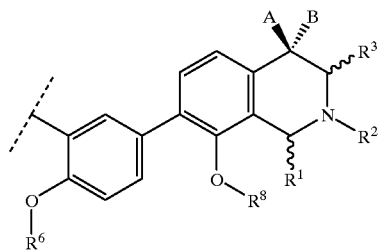

ARYLISOQUINOLINE III wherein:
(i) A or B is $C_1$–$C_6$ alkyl, acyl, aryl, halo, nitro, amino, azido, hydroxyl, acyloxy, alkoxy, aryloxy, glycosyloxy, thiol or cyano; or A and B together are H, =O, =S, or —O(CH$_2$)$_n$O—, wherein n is an integer from 2–4;
(ii) R² is H, $C_1$–$C_6$ alkyl, an amide, or sulfonamide;
(iii) R¹ and R³ are the same or different and each is ◂H, ⋯H, ◂CH$_3$; or ⋯CH$_3$;
(iv) R⁵, R⁶, and R⁸ are the same or different and each is H or $C_1$–$C_6$ alkyl;
(v) one or more aromatic hydrogen substituent(s) may instead be $C_1$–$C_6$ alkyl, acyl, halo, nitro, amino, hydroxyl, acyloxy, alkoxy, aryloxy, glycosyloxy, thiol or cyano; and
(vi) the tetrahydroisoquinoline ring may instead be a dihydroisoquinoline ring or a fully aromatic isoquinoline ring; or any combination of the foregoing.

7. A dimeric arylisoquinoline of the formula:

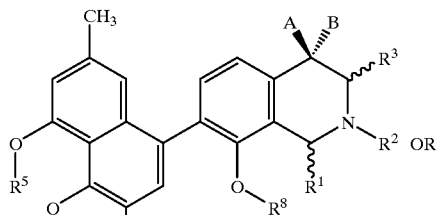

SERIES I

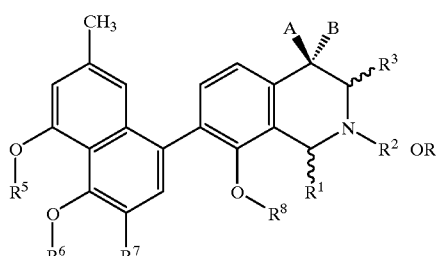

SERIES II

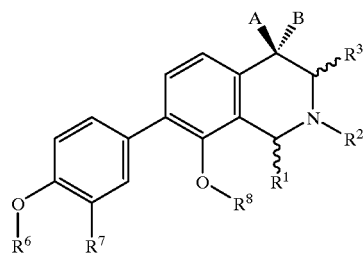

SERIES III wherein:
(a) A or B is azido, alkoxy, aryloxy, glycosyloxy; or A and B together are =O, =S, or —O(CH$_2$)$_n$O—, wherein n is an integer from 2–4;
(b) R² is H, $C_1$–$C_6$ alkyl, an amide, or sulfonamide;
(c) R¹ and R³ are the same or different and each is ◂H, ⋯H, ◂CH$_3$; or ⋯CH$_3$;
(d) R⁵, R⁶, and R⁸ are the same or different and each is H or $C_1$–$C_6$ alkyl;
(e) one or more aromatic hydrogen substituent(s) may instead be $C_1$–$C_6$ alkyl, acyl, halo, nitro, amino, hydroxyl, acyloxy, alkoxy, aryloxy, glycosyloxy, thiol or cyano;
(f) the tetrahydroisoquinoline ring may instead be a dihydroisoquinoline ring or a fully aromatic isoquinoline ring; or any combination of the foregoing, and
(g) R⁷ is an arylisoquinoline monomer selected from the group consisting of derivatives of dioncophylline D, wherein the configuration at C-1 or C-3 is instead S; one or more phenolic hydroxyl group(s) is instead an ester, sulfonate ester, or ether group; a methyl ether group is instead a phenolic hydroxyl group; one or more phenolic hydroxyl group(s) is instead an aromatic hydrogen substituent; the secondary amine site is instead an amide, sulfonamide, tertiary amine, alkyl quaternary ammonium salt or corresponding Hoffmann elimination product thereof; one or more aromatic hydrogen substituent(s) is instead halo, nitro, amino, hydroxyl, acyloxy, alkoxy, aryloxy, glycosyloxy, thiol or cyano; at least one $CH_3$ is instead H; and/or the tetrahydroisoquinoline is instead a dihydroisoquinoline; or any combination of the foregoing.

8. A dimeric arylisoquinoline of the formula:

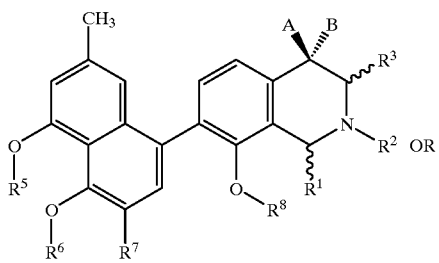

SERIES I

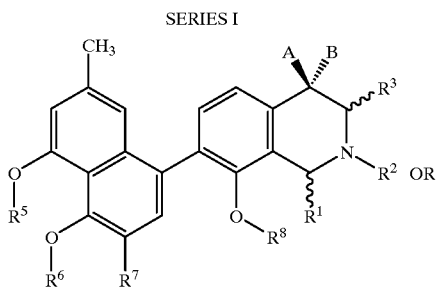

SERIES II

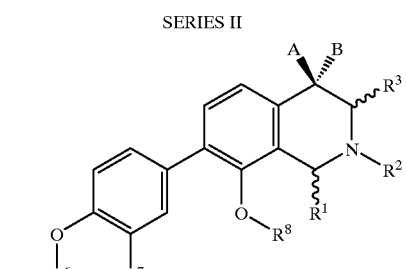

SERIES III wherein:
(a) A or B is azido, alkoxy, aryloxy, glycosyloxy; or A and B together are =O, =S, or —O(CH$_2$)$_n$O—, wherein n is an integer from 2–4;
(b) $R^2$ is H, $C_1$–$C_6$ alkyl, an amide, or sulfonamide;
(c) $R^1$ and $R^3$ are the same or different and each is ◀H, ⋯ıııH, ◀CH$_3$; or ⋯ıııCH$_3$;
(d) $R^5$, $R^6$, and $R^8$ are the same or different and each is H or $C_1$–$C_6$ alkyl;
(e) one or more aromatic hydrogen substituent(s) may instead be $C_1$–$C_6$ alkyl, acyl, halo, nitro, amino, hydroxyl, acyloxy, alkoxy, aryloxy, glycosyloxy, thiol or cyano;
(f) the tetrahydroisoquinoline ring may instead be a dihydroisoquinoline ring or a fully aromatic isoquinoline ring; or any combination of the foregoing, and
(g) $R^7$ is an arylisoquinoline monomer selected from the group consisting of derivatives of dioncophylline D, ancistrobrevine A, 6-O-demethyl-ancistrobrevine A, yaoundamine A, yaoundamine B, ancistroheynine A, dioncophylline B, dioncopeltine A, dioncophylline A, dioncophylline C, dioncolactone A, N-methyl-dioncophylline A, ancistrobrevine D, ancistrocladine, 5'-O-demethyl-8-O-methyl-7-epi-dioncophylline A, 5'-O-demethyl-7-epi-dioncophylline A, hamatine, ancistrobarterine A, 7-epi-dioncophylline A, N-formyl ancistrocladine, N-methyl-ancistrocladine, 6-deoxy-N-methyl-ancistrocladine, N-formyl-O,O-dimethyl-dioncophylline C, N-formyl-dioncophylline C, N-formyl-8-O-benzyl-dioncophylline C, N-formyl-8-O-methyl-dioncophylline C, N-formyl-8-O-pivaloyl-dioncophylline C, N-formyl-8-O-acetyl-dioncophylline C, N-formyl-8-O-benzoyl-dioncophylline C, and 8-O-methyl-dioncophylline C, wherein: (a) the configurations at C-1 and C-3 are the same or different, and each is R or S; the configuration about the naphthalene/isoquinoline axis is P or M, one or more phenolic hydroxyl group(s) may instead be an ester, sulfonate ester, or ether group; one or more methyl ether group(s) may instead be a phenolic hydroxyl group; one or more phenolic hydroxyl group (s) may instead be an aromatic hydrogen substituent; one or more secondary amine site(s) may instead be an amide, sulfonamide, tertiary amine, alkyl quaternary ammonium salt or corresponding Hoffmann elimination product thereof, one or more tertiary amine site(s) may instead be a secondary amine; one or more aromatic hydrogen substituent(s) may instead be $C_1$–$C_6$ alkyl, acyl, halo, nitro, amino, hydroxyl, acyloxy, alkoxy, aryloxy, glycosyloxy, thiol or cyano; at least one $CH_3$ may instead be H; the tetrahydroisoquinoline may instead be a dihydroisoquinoline; and (b) a substituent at C-4 is $C_1$–$C_6$ alkyl, halo, nitro, amino, azido, hydroxyl, acyloxy, alkoxy, aryloxy, glycosyloxy, thiol, cyano or oxo; or any combination of the foregoing.

9. A dimeric arylisoquinoline of the formula:

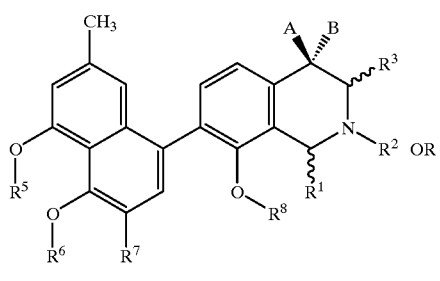

SERIES I

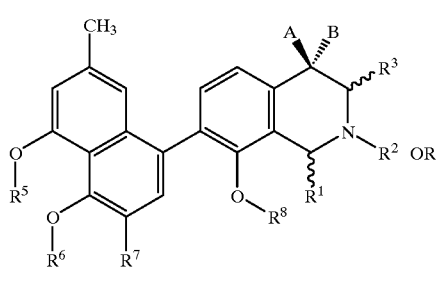

SERIES II

31

-continued

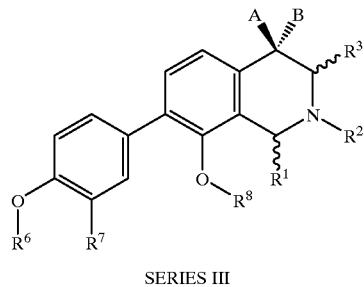

SERIES III wherein:
(a) A or B is azido, alkoxy, aryloxy, glycosyloxy; or A and B together are =O, =S, or —O(CH$_2$)$_n$O—, wherein n is an integer from 2–4;
(b) R$^2$ is H, C$_1$–C$_6$ alkyl, an amide, or sulfonamide;
(c) R$^1$ and R$^3$ are the same or different and each is ◂▬H, ⋯⋯H, ◂▬CH$_3$; or ⋯⋯CH$_3$;
(d) R$^5$, R$^6$, and R$^8$ are the same or different and each is H or C$_1$–C$_6$ alkyl;
(e) one or more aromatic hydrogen substituent(s) may instead be C$_1$–C$_6$ alkyl, acyl, halo, nitro, amino, hydroxyl, acyloxy, alkoxy, aryloxy, glycosyloxy, thiol or cyano;
(f) the tetrahydroisoquinoline ring may instead be a dihydroisoquinoline ring or a fully aromatic isoquinoline ring; or any combination of the foregoing, and
(g) R$^7$ is an arylisoquinoline monomer selected from the group consisting of derivatives of dioncophylline D, ancistrobrevine A, 6-O-demethyl-ancistrobrevine A, yaoundamine A, yaoundamine B, ancistroheynine A, dioncophyllacine A, dioncophyllacine B, dioncophylline B, dioncopeltine A, dioncophylline A, dioncophylline C, dioncolactone A, N-methyl-dioncophylline A, ancistrobrevine D, ancistrocladine, 5'-O-demethyl-8-O-methyl-7-epi-dioncophylline A, 5'-O-demethyl-7-epi-dioncophylline A, dioncophylleine A, hamatine, ancistrobarterine A, 7-epi-dioncophylline A, N-formyl ancistrocladine, N-methyl-ancistrocladine, 6-deoxy-N-methyl-ancistrocladine, N-formyl-O,O-dimethyl-dioncophylline C, N-formyl-dioncophylline C, N-formyl-8-O-benzyl-dioncophylline C, N-formyl-8-O-methyl-dioncophylline C, N-formyl-8-O-pivaloyl-dioncophylline C, N-formyl-8-O-acetyl-dioncophylline C, N-formyl-8-O-benzoyl-dioncophylline C, and 8-O-methyl-dioncophylline C, wherein: (a) the configurations at C-1 and C-3 are the same or different, and each is R or S; the configuration about the naphthalene/isoquinoline axis is P or M, one or more phenolic hydroxyl group(s) may instead be an ester, sulfonate ester, or ether group; one or more methyl ether group(s) may instead be a phenolic hydroxyl group; one or more phenolic hydroxyl group(s) may instead be an aromatic hydrogen substituent; one or more secondary amine site(s) may instead be an amide, sulfonamide, tertiary amine, alkyl quaternary ammonium salt or corresponding Hoffmann elimination product thereof, one or more tertiary amine site(s) may instead be a secondary amine; one or more aromatic hydrogen substituent(s) may instead be C$_1$–C$_6$ alkyl, acyl, halo, nitro, amino, hydroxyl, acyloxy, alkoxy, aryloxy, glycosyloxy, thiol or cyano; (b) the isoquinoline is instead a fully aromatic isoquinoline; and (c) a substituent at C-4 is acyloxy, alkoxy, aryloxy, glycosyloxy or oxo; or any combination of the foregoing.

32

10. A dimeric arylisoquinoline of the formula:

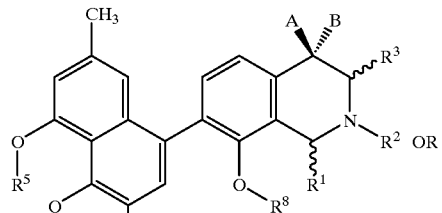

SERIES I

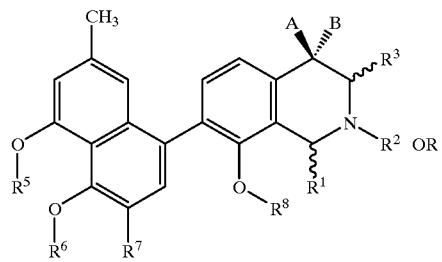

SERIES II

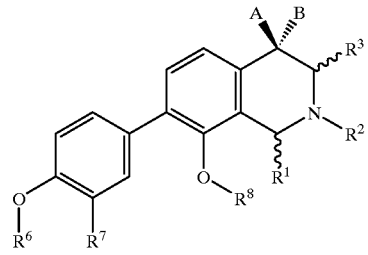

SERIES III wherein:
(a) A or B is azido, alkoxy, aryloxy, glycosyloxy; or A and B together are =O, =S, or —O(CH$_2$)$_n$O—, wherein n is an integer from 2–4;
(b) R$^2$ is H, C$_1$–C$_6$ alkyl, an amide, or sulfonamide;
(c) R$^1$ and R$^3$ are the same or different and each is ◂▬H, ⋯⋯H, ◂▬CH$_3$; or ⋯⋯CH$_3$;
(d) R$^5$, R$^6$, and R$^8$ are the same or different and each is H or C$_1$–C$_6$ alkyl;
(e) one or more aromatic hydrogen substituent(s) may instead be C$_1$–C$_6$ alkyl, acyl, halo, nitro, amino, hydroxyl, acyloxy, alkoxy, aryloxy, glycosyloxy, thiol or cyano;
(f) the tetrahydroisoquinoline ring may instead be a dihydroisoquinoline ring or a fully aromatic isoquinoline ring; or any combination of the foregoing, and
(g) R$^7$ is an arylisoquinoline monomer selected from the group consisting of derivatives of korupensamine A, korupensamine B, korupensamine C, korupensamine D, and ancistrobrevine B, wherein: (a) the configurations at C-1 and C-3 are the same or different, and each is R or S; the configuration about the naphthalene/isoquinoline axis is P or M, one or more phenolic hydroxyl group(s) may instead be an ester, sulfonate ester, or ether group; one or more methyl ether group(s) may instead be a phenolic hydroxyl group; one or more phenolic hydroxyl group(s) may instead be an aromatic hydrogen substituent; one or more secondary amine site(s) may instead be an amide, sulfonamide, tertiary amine, alkyl quaternary ammonium salt or corresponding Hoffmann elimination product thereof, one or more tertiary amine site(s) may instead be a secondary amine; one or more aromatic hydrogen substituent(s) may instead be halo, nitro, amino, hydroxyl, acyloxy, alkoxy, aryloxy, glycosyloxy, thiol or cyano; and (b) a substituent at C-4 is $C_1$–$C_6$ alkyl, halo, nitro, amino, hydroxyl, acyloxy, alkoxy, aryloxy, glycosyloxy, thiol, cyano or oxo; or any combination of the foregoing.

11. A dimeric arylisoquinoline of the formula:

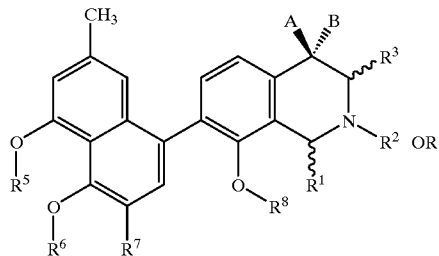

SERIES I

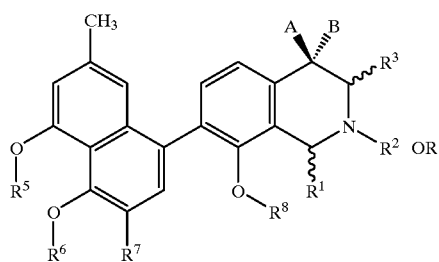

SERIES II

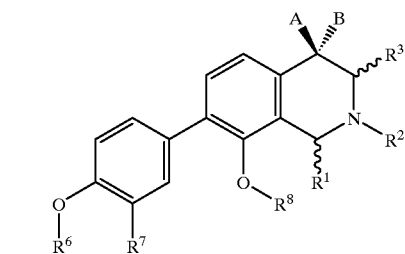

SERIES III wherein:
(a) A or B is azido, alkoxy, aryloxy, glycosyloxy; or A and B together are =O, =S, or —O($CH_2$)$_n$O—, wherein n is an integer from 2–4;

(b) $R^2$ is H, $C_1$–$C_6$ alkyl, an amide, or sulfonamide;

(c) $R^1$ and $R^3$ are the same or different and each is ◂H, ⋯‖H, ◂CH$_3$; or ⋯‖CH$_3$;

(d) $R^5$, $R^6$, and $R^8$ are the same or different and each is H or $C_1$–$C_6$ alkyl;

(e) one or more aromatic hydrogen substituent(s) may instead be $C_1$–$C_6$ alkyl, acyl, halo, nitro, amino, hydroxyl, acyloxy, alkoxy, aryloxy, glycosyloxy, thiol or cyano;

(f) the tetrahydroisoquinoline ring may instead be a dihydroisoquinoline ring or a fully aromatic isoquinoline ring; or any combination of the foregoing, and (g) $R^7$ is an arylisoquinoline monomer selected from the group consisting of derivatives of korupensamine A, korupensamine B, korupensamine C, korupensamine D, and ancistrobrevine B, wherein: (a) the configurations at C-1 and C-3 are the same or different, and each is R or S; the configuration about the naphthalene/isoquinoline axis is P or M, one or more phenolic hydroxyl group may instead be an ester, sulfonate ester, or ether group; one or more methyl ether group may instead be a phenolic hydroxyl group; one or more phenolic hydroxyl group may instead be an aromatic hydrogen substituent; one or more secondary amine site may instead be an amide, sulfonamide, tertiary amine, alkyl quaternary ammonium salt or corresponding Hoffmann elimination product thereof, one or more tertiary amine site may instead be a secondary amine; one or more aromatic hydrogen substituent may instead be $C_1$–$C_6$ alkyl, acyl, halo, nitro, amino, hydroxyl, acyloxy, alkoxy, aryloxy, glycosyloxy, thiol or cyano; at least one $CH_3$ may instead be H; the tetrahydroisoquinoline may instead be a dihydroisoquinoline or a fully aromatic isoquinoline; (b) a substituent at C-4 is acyloxy, alkoxy, aryloxy, glycosyloxy or oxo; and (c) at least one aromatic hydrogen substituent is instead an acyl or $C_1$–$C_6$ alkyl, and/or a substituent at C-2' is not methyl when C-1 and C-3 are each substituted with a methyl; or any combination of the foregoing.

* * * * *